United States Patent
Glunz et al.

(10) Patent No.: US 6,653,295 B2
(45) Date of Patent: Nov. 25, 2003

(54) INHIBITORS OF HEPATITIS C VIRUS NS3 PROTEASE

(75) Inventors: Peter William Glunz, Wilmington, DE (US); Brent Dale Douty, East Fallowfield, PA (US); Wei Han, Newark, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 22 days.

(21) Appl. No.: 10/015,304

(22) Filed: Dec. 12, 2001

(65) Prior Publication Data

US 2003/0064962 A1 Apr. 3, 2003

Related U.S. Application Data

(60) Provisional application No. 60/255,290, filed on Dec. 13, 2000.

(51) Int. Cl.[7] ............... A61K 31/69; A61K 31/33; A61K 31/515; C07D 239/70
(52) U.S. Cl. ............... 514/64; 514/183; 514/256; 514/258.1; 514/259.1; 514/259.5; 544/229; 544/253; 544/315; 544/322; 544/335
(58) Field of Search ............... 514/183, 64, 256, 514/258.1, 259.1, 259.5; 544/229, 253, 315, 322, 335

(56) References Cited

FOREIGN PATENT DOCUMENTS

| WO | WO 95/35308 | 12/1995 |
|----|-------------|---------|
| WO | 9535308 | * 12/1995 |
| WO | WO 98/17679 | 4/1998 |
| WO | WO 99/31122 | 6/1999 |
| WO | WO 99/64442 | 12/1999 |
| WO | WO 00/20400 | 4/2000 |
| WO | WO 01/02424 | 1/2001 |
| WO | WO 01/07407 | 2/2001 |

OTHER PUBLICATIONS

Chemical Abstract DN 124:290273 also cited as WO 9535308.*
"Antiviral Agents",Drug Therapy for viral infections, 6th Edition,pp. 1615–1627(1986).*

* cited by examiner

Primary Examiner—Mukund J. Shah
Assistant Examiner—Sudhaker B. Patel
(74) Attorney, Agent, or Firm—James Epperson; Scott K. Larsen

(57) ABSTRACT

The present invention relates generally to a novel class of pyrimidinones of Formula (I):

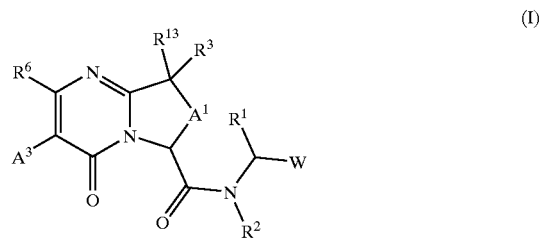

that are useful as serine protease inhibitors, and more particularly as Hepatitis C virus NS3 protease inhibitors. This invention also relates to pharmaceutical compositions comprising these compounds and methods of using the same.

7 Claims, No Drawings

INHIBITORS OF HEPATITIS C VIRUS NS3 PROTEASE

FIELD OF THE INVENTION

The present invention relates generally to a novel class of pyrimidinones that are useful as serine protease inhibitors, and more particularly as Hepatitis C virus NS3 protease inhibitors. This invention also relates to pharmaceutical compositions comprising these compounds and methods of using the same.

BACKGROUND OF THE INVENTION

Hepatitis C virus (HCV) is the major cause of transfusion and community-acquired non-A, non-B hepatitis worldwide. Approximately 2% of the world's population are infected with the virus. In the Unites States, hepatitis C represents approximately 20% of cases of acute hepatitis. Unfortunately, self-limited hepatitis is not the most common course of acute HCV infection. In the majority of patients, symptoms of acute hepatitis resolve, but alanine aminotransferase (a liver enzyme diagnostic for liver damage) levels often remain elevated and HCV RNA persists. Indeed, a propensity to chrininicity is the most distinguishing characteristic of hepatitis C, occurring in at least 85% of patients with acute HCV infection. The factors that lead to chronicity in hepatitis C are not well defined. Chronic HCV infection is associated with increased incidence of liver cirrhosis and liver cancer. No vaccines are available for this virus, and current treatment is restricted to the use of alpha interferon, which is effective in only 15–20% of patients. Recent clinical studies have shown that combination therapy of alpha interferon and ribavirin leads to sustained efficacy in 40% of patients (Poynard et al. *Lancet* 1998, 352, 1426–1432.). However, a majority of patients still either fail to respond or relapse after completion of therapy. Thus, there is a clear need to develop more effective therapeutics for treatment of HCV-associated hepatitis.

HCV is a positive-stranded RNA virus. Based on comparison of deduced amino acid sequence and the extensive similarity in the 5' untranslated region, HCV has been classified as a separate genus in the Flaviviridae family, which also includes flaviviruses such as yellow fever virus and animal pestiviruses like bovine viral diarrhea virus and swine fever virus. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The RNA genome is about 9.6 Kb in length, and encodes a single polypeptide of about 3000 amino acids. The 5' untranslated region contains an internal ribosome entry site (IRES), which directs cellular ribosomes to the correct AUG for initiation of translation. As was determined by transient expression of cloned HCV cDNAs, the precursor protein is cotranslationally and posttranslationally processed into at least 10 viral structural and nonstructural (NS) proteins by the action of a host signal peptidase and by two distinct viral proteinase activities. The translated product contains the following proteins: core-E1-E2-p7-NS2-NS3-NS4A-NS4B-NS5A-NS5B.

The N-terminal portion of NS3 functions as a proteolytic enzyme that is responsible for the cleavage of sites liberating the nonstructural proteins NS4A, NS4B, NS5A, and NS5B. NS3 has further been shown to be a serine protease. Although the functions of the NS proteins are not completely defined, it is known that NS4A is a protease cofactor and NS5B is an RNA polymerase involved in viral replication. Thus agents that inhibit NS3 proteolytic processing of the viral polyprotein are expected to have antiviral activity.

There are several patents that disclose HCV NS3 protease inhibitors. WO98/17679 describes peptide and peptidomimetic inhibitors with the following formula: $U—E^8—E^7—E^6—E^5—E^4—NH—CH(CH_2G^1)—W^1$, where W is one of a variety of electrophilic groups, including boronic acid or ester. E4 represents either an amino acid or one of a series of peptidomimetic groups, the sythesis of which are not exemplified. HCV protease inhibitors described in the present case are not covered.

Based on the large number of persons currently infected with HCV and the limited treatments available, it is desirable to discover new inhibitors of HCV NS3 protease.

SUMMARY OF THE INVENTION

One object of the present invention is to provide compounds, or pharmaceutically acceptable salt forms or prodrugs thereof, which are useful as inhibitors of hepatitis C virus protease, more specifically, the NS3 protease.

It is another object of the present invention to provide pharmaceutical compositions comprising a pharmaceutically acceptable carrier and a therapeutically effective amount of a compound of Formula (I), or pharmaceutically acceptable salt form or prodrug thereof.

It is another object of the present invention to provide a method for the treatment or prevention of HCV comprising administering to a host in need of such treatment a therapeutically effective amount of a compound of Formula (I), or a pharmaceutically acceptable salt form or prodrug thereof.

These and other objects of the invention, which will become apparent during the following detailed description, have been achieved by the discovery that compounds of Formula (I):

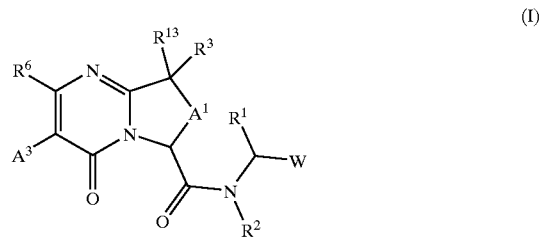

(I)

or pharmaceutically acceptable salt forms or prodrugs thereof, wherein $R^1$, $R^2$, $R^3$, $R^6$, $R^{13}$, W, $A^1$ and $A^3$ are defined below, are effective inhibitors of HCV NS3 protease.

It is another object of the present invention to provide a kit or container containing at least one of the compounds of the present invention in an amount effective for use as a standard or reagent in a test or assay for determining the ability of a potential pharmaceutical to inhibit HCV NS3 protease, HCV growth, or both.

It is another object of the present invention to provide novel compounds for use in therapy.

It is another object of the present invention to provide the use of novel compounds for the manufacture of a medicament for the treatment of HCV.

DETAILED DESCRIPTION OF THE INVENTION

[1] Thus, in one embodiment, the present invention provides a compound of Formula (I):

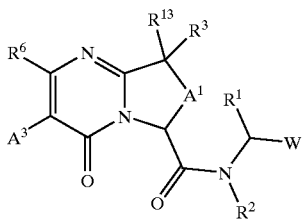

(I)

or a stereoisomer, pharmaceutically acceptable salt form or prodrug thereof, wherein:

$A^1$ is —$CH_2$—, —$CH_2CH_2$—, —$CH_2CH_2CH_2$—, —$CR^5R^{5a}$—, —$CH_2$—$CR^5R^{5a}$—, —$CH_2$—$CH_2$—$CR^5R^{5a}$—, —$A^2$—$CH_2$—, —$A^2$—$CH_2CH_2$—, or —$CH_2$—$A^2$—$CH_2$—;

$A^2$ is O, S, or $NR^7$;

$A^3$ is H, —$C(=O)R^{9a}$, —$OR^{9a}$, —$SR^{9a}$, —$S(=O)R^{9a}$, —$S(=O)_2R^{9a}$, —$NHCOR^{9a}$, —$CONHR^{9a}$, —$NHS(=O)_2R^{9a}$, —$S(=O)_2NHR^{9a}$, —$NHC(=O)OR^{9a}$, —$OC(=O)NHR^{9a}$, —$C(=O)OR^{9a}$, —O—$C(=O)R^{9a}$, —$NR^8R^{9a}$; —NH—$A^4$—$R^{9b}$; —NH—$A^4$—$A^5$—$R^{9b}$; or —NH—$A^4$—$A^5$—$A^6R^{9b}$;

W is selected from the group:
—$B(OR^{26})(OR^{27})$,
—$C(=O)C(=O)$—Q,
—$C(=O)C(=O)NH$—Q,
—$C(=O)C(=O)$—O—Q,
—$C(=O)CF_2C(=O)NH$—Q,
—$C(=O)Q^3$,
—$C(=O)CF_3$,
—$C(=O)CF_2CF_3$, and
—$C(=O)H$;

Q is selected from the group:
—$(CR^{10}R^{10c})_m$—$Q^1$,
—$(CR^{10}R^{10c})_m$—$Q^2$,
$C_1$-$C_4$ alkyl substituted with $Q^1$,
$C_2$-$C_4$ alkenyl substituted with $Q^1$,
$C_2$-$C_4$ alkynyl substituted with $Q^1$,
an amino acid residue,
—$A^7$—$A^8$, and
—$A^7$—$A^8$—$A^9$;

m is 1, 2, 3, or 4;

$Q^1$ is selected from the group:
—$CO_2R^{11}$, —$SO_2R^{11}$, —$SO_3R^{11}$, —$P(O)_2R^{11}$, —$P(O)_3R^{11}$;
aryl substituted with 0–4 $Q^{1a}$; and
5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–4 $Q^{1a}$;

$Q^{1a}$ is H, F, Cl, Br, I, —$NO_2$, —CN, —NCS, —$CF_3$, —$OCF_3$, —$CO_2R^{19}$, —$C(=O)NR^{19}R^{19a}$, —NHC(=O)$R^{19}$, —$SO_2R^{19}$, —$SO_2NR^{19}R^{19a}$, —$NR^{19}R^{19a}$, —$OR^{19}$, —$SR^{19}$, $C_1$-$C_4$ alkyl, $C_1$-$C_4$ alkoxy, $C_1$-$C_4$ haloalkyl, or $C_1$-$C_4$ haloalkoxy;

$Q^2$ is —X—$NR^{12}$—Z, —$NR^{12}$—Y—Z, or —X—$NR^{12}$—Y—Z;

$Q^3$ is aryl substituted with 0–3 $Z^c$; or
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $Z^c$;

X is —$C(=O)$—, —S—, —$S(=O)$—, —$S(=O)_2$—, —P(O)—, —$P(O)_2$—, or —$P(O)_3$—;

Y is —$C(=O)$—, —S—, —$S(=O)$—, —$S(=O)_2$—, —P(O)—, —$P(O)_2$—, or —$P(O)_3$—;

Z is selected from the group:
$C_1$-$C_4$ haloalkyl;
$C_1$-$C_4$ alkyl substituted with 0–3 $Z^a$;
$C_2$-$C_4$ alkenyl substituted with 0–3 $Z^a$;
$C_2$-$C_4$ alkynyl substituted with 0–3 $Z^a$;
$C_3$-$C_{10}$ cycloalkyl substituted with 0–5 $Z^b$;
aryl substituted with 0–5 $Z^b$;
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $Z^b$;
an amino acid residue;
—$A^7$—$A^8$; and
—$A^7$—$A^8$—$A^9$;

$Z^a$ is selected from the group:
H, F, Cl, Br, I, —$NO_2$, —CN, —NCS, —$CF_3$, —$OCF_3$, —$CO_2R^{20}$, —$C(=O)NR^{20}R^{20a}$, —NHC(=O)$R^{20}$, —$NR^{20}R^{20a}$, —$OR^{20}$, —$SR^{20}$, —$S(=O)R^{20}$, —$SO_2R^{20}$, —$SO_2NR^{20}R^{20a}$, $C_1$-$C_4$ alkyl, $C_1$-$C_4$ haloalkyl, $C_1$-$C_4$ haloalkoxy;
$C_3$-$C_{10}$ cycloalkyl substituted with 0–5 $Z^b$;
$C_3$-$C_{10}$ carbocyle substituted with 0–5 $Z^b$;
aryl substituted with 0–5 $Z^b$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $Z^b$;

$Z^b$ is selected from the group:
H, F, Cl, Br, I, —$NO_2$, —CN, —NCS, —$CF_3$, —$OCF_3$, —$CO_2R^{20}$, —$C(=O)NR^{20}R^{20a}$, —NHC(=O)$R^{20}$, —$NR^{20}R^{20a}$, —$OR^{20}$, —$SR^{20}$, —$S(=O)R^{20}$, —$SO_2R^{20}$, —$SO_2NR^{20}R^{20a}$, $C_1$-$C_4$ alkyl, $C_1$-$C_4$ haloalkyl, $C_1$-$C_4$ haloalkoxy;
$C_3$-$C_{10}$ cycloalkyl substituted with 0–5 $Z^c$;
$C_3$-$C_{10}$ carbocyle substituted with 0–5 $Z^c$;
aryl substituted with 0–5 $Z^c$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $Z^c$;

$Z^c$ is H, F, Cl, Br, I, —$NO_2$, —CN, —NCS, —$CF_3$, —$OCF_3$, —$CO_2R^{20}$, —$C(=O)NR^{20}R^{20a}$, —NHC(=O)$R^{20}$, —$NR^{20}R^{20a}$, —$OR^{20}$, —$SR^{20}$, —$S(=O)R^{20}$, —$SO_2R^{20}$, —$SO_2NR^{20}R^{20a}$, $C_1$-$C_4$ alkyl, $C_1$-$C_4$ haloalkyl, or $C_1$-$C_4$ haloalkoxy;

$R^1$ is selected from the group: H, F;
$C_1$-$C_6$ alkyl substituted with 0–3 $R^{1a}$;
$C_2$-$C_6$ alkenyl substituted with 0–3 $R^{1a}$;

$C_2$–$C_6$ alkynyl substituted with 0–3 $R^{1a}$; and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH, —$CO_2R^{1b}$, —$SO_2R^{1b}$, —$SO_3R^{1b}$, —$P(O)_2R^{1b}$, —$P(O)_3R^{1b}$, —C(=O)$NHR^{1b}$, —NHC(=O)$R^{1b}$, —$SO_2NHR^{1b}$, —$OR^{1b}$, —$SR^{1b}$, $C_3$–$C_6$ cycloalkyl, $C_1$–$C_6$ alkoxy, —S—($C_1$–$C_6$ alkyl);
$C_1$–$C_4$ alkyl substituted with 0–3 $R^{1c}$;
aryl substituted with 0–5 $R^{1c}$;
—O—$(CH_2)_n$-aryl substituted with 0–5 $R^{1c}$;
—S—$(CH_2)_n$-aryl substituted with 0–5 $R^{1c}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{1c}$;

n is 0, 1 or 2;

$R^{1b}$ is H;
$C_1$–$C_4$ alkyl substituted with 0–3 $R^{1c}$;
$C_2$–$C_4$ alkenyl substituted with 0–3 $R^{1c}$;
$C_2$–$C_4$ alkynyl substituted with 0–3 $R^{1c}$;
$C_3$–$C_6$ cycloalkyl substituted with 0–5 $R^{1c}$;
aryl substituted with 0–5 $R^{1c}$;
aryl-$C_1$–$C_4$ alkyl substituted with 0–4 $R^{1c}$; or
5–6 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{1c}$;

$R^{1c}$ is selected at each occurrence from the group:
$C_1$–$C_4$ alkyl, Cl, F, Br, I, OH, SH, —CN, —$NO_2$, —$OR^{1d}$, —C(=O)$OR^{1d}$, —$NR^{1d}R^{1d}$, —$SO_2R^{1d}$, —$SO_3R^{1d}$, —C(=O)$NHR^{1d}$, —NHC(=O)$R^{1d}$, $SO_2NHR^{1d}$, —$CF_3$, —$OCF_3$, $C_3$–$C_6$ cycloalkyl, phenyl, and benzyl;

$R^{1d}$ is selected at each occurrence from the group: H, $C_1$–$C_4$ alkyl, phenyl and benzyl;

$R^2$ is H or $C_1$–$C_4$ alkyl;

$R^3$ is selected from the group: $R^4$,
—$(CH_2)_p$—NH—$R^4$,
—$(CH_2)_p$—NHC(=O)—$R^4$,
—$(CH_2)_p$—C(=O)NH—$R^4$,
—$(CH_2)_p$—C(=O)O—$R^4$,
—$(CH_2)_p$—C(=O)C(=O)—$R^4$,
—$(CH_2)_p$—C(=O)C(=O)NH—$R^4$,
—$(CH_2)_p$—NHC(=O)NH—$R^4$,
—$(CH_2)_p$—NHC(=O)NHC(=O)—$R^4$,
—$(CH_2)_p$—NHS(=O)$_2$—$R^4$,
—$(CH_2)_p$—S(=O)$_2$NH—$R^4$,
—$(CH_2)_p$—C(=O)—$R^4$,
—$(CH_2)_p$—O—$R^4$, and
—$(CH_2)_p$—S—$R^4$;

p is 0, 1, or 2;

$R^4$ is selected from the group:
$C_1$–$C_6$ alkyl substituted with 0–3 $R^{4a}$;
$C_2$–$C_6$ alkenyl substituted with 0–3 $R^{4a}$;
$C_2$–$C_6$ alkynyl substituted with 0–3 $R^{4a}$;
$C_3$–$C_{10}$ cycloalkyl substituted with 0–4 $R^{4b}$;
aryl substituted with 0–5 $R^{4b}$;
aryl—$C_1$–$C_4$ alkyl substituted with 0–5 $R^{4b}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{4b}$;

$R^{4a}$ is, at each occurrence, independently selected from:
H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, OC(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}$C(=O)$OR^{11a}$, —$NR^{11}$C(=O)$NR^{11}R^{11a}$, —$NR^{11}SO_2NR^{11}R^{11a}$, —$NR^{11}SO_2R^{11a}$, —OP(O)($OR^{11}$)$_2$;
$C_1$–$C_4$ alkyl substituted with 0–3 $R^{4b}$;
$C_2$–$C_4$ alkenyl substituted with 0–3 $R^{4b}$;
$C_2$–$C_4$ alkynyl substituted with 0–3 $R^{4b}$;
$C_3$–$C_7$ cycloalkyl substituted with 0–4 $R^{4c}$;
aryl substituted with 0–5 $R^{4c}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{4c}$;

$R^{4b}$ is, at each occurrence, independently selected from:
H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}$C(=O)$OR^{11a}$, —OC(=O)$NR^{11}R^{11a}$, —$NR^{11}$C(=O)$NR^{11}R^{11a}$, —$NR^{11}SO_2NR^{11}R^{11a}$, —$NR^{11}SO_2R^{11a}$, —OP(O)($OR^{11}$)$_2$;
$C_1$–$C_4$ alkyl substituted with 0–3 $R^{4c}$;
$C_2$–$C_4$ alkenyl substituted with 0–3 $R^{4c}$;
$C_2$–$C_4$ alkynyl substituted with 0–3 $R^{4c}$;
$C_3$–$C_6$ cycloalkyl substituted with 0–4 $R^{4d}$;
aryl substituted with 0–5 $R^{4d}$; and
5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4c}$ is, at each occurrence, independently selected from:
H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, $C_1$–$C_4$ haloalkyl, $C_1$–$C_4$ haloalkoxy;
$C_1$–$C_4$ alkyl substituted with 0–3 $R^{4d}$;
$C_2$–$C_4$ alkenyl substituted with 0–3 $R^{4d}$;
$C_2$–$C_4$ alkynyl substituted with 0–3 $R^{4d}$;
$C_3$–$C_6$ cycloalkyl substituted with 0–4 $R^{4d}$;
aryl substituted with 0–5 $R^{4d}$; and
5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4d}$ is, at each occurrence, independently selected from:
H, F, Cl, Br, I, —$NO_2$, —CN, —NCS, —$CF_3$, —$OCF_3$, =O, OH, —$CO_2H$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, $C_1$–$C_4$ alkyl, $C_1$–$C_4$ alkoxy, $C_1$–$C_4$ haloalkyl, $C_1$–$C_4$ haloalkoxy, phenyl, and benzyl;

$R^5$ and $R^{5a}$ are, at each occurrence, independently selected from the group: H, $C_1$–$C_4$ alkyl, phenyl and benzyl;

$R^6$ is selected from the group: H, $C_1$–$C_6$ alkyl, $C_2$–$C_6$ alkenyl, $C_2$–$C_6$ alkynyl, $C_3$–$C_6$ cycloalkyl, aryl, and 5–6 membered heterocyclic group consisting of carbon atoms and 1–4 heteroatoms selected from the group: O, S, and N; optionally saturated, partially unsaturated or unsaturated;

$R^{6a}$ is selected from the group: H, F, Cl, Br, I, —$CF_3$, —$NR^{11}R^{11a}$, —$OR^{11}$, —$SR^{11}$, —$C(=NH)NH_2$, $C_1$–$C_4$ alkyl, $C_1$–$C_4$ haloalkyl, $C_3$–$C_6$ cycloalkyl;

aryl substituted with 0–3 $R^{6b}$; and

5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–3 $R^{6b}$;

$R^6b$ is selected from the group: H, F, Cl, Br, I, —$CO_2R^{11}$, $NR^{11}R^{11a}$, —$OR^{11}$, —$SR^{11}$, —$C(=NH)NH_2$, $C_1$–$C_4$ alkyl, and $C_1$–$C_4$ haloalkyl;

$R^7$ is H or $C_1$–$C_4$ alkyl;

$R^8$ is H, $C_1$–$C_4$ alkyl, $C_2$–$C_4$ alkenyl, $C_2$–$C_4$ alkynyl, $C_3$–$C_4$ cycloalkyl, aryl or aryl-$C_1$–$C_4$ alkyl;

$R^{9a}$ is selected from the group: H;

$C_1$–$C_6$ alkyl substituted with 0–3 $R^{9c}$;
$C_2$–$C_6$ alkenyl substituted with 0–3 $R^{9c}$;
$C_2$–$C_6$ alkynyl substituted with 0–3 $R^{9c}$;
$C_3$–$C_6$ cycloalkyl substituted with 0–3 $R^{9d}$;
aryl substituted with 0–5 $R^{9d}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^{9b}$ is selected from the group: H, —$S(=O)R^{11}$, —$S(=O)_2R^{11}$, —$S(=O)_2NHR^{11}$, —$C(=O)R^{11}$, —$C(=O)OR^{11}$, —$C(=O)NHR^{11}$; —$C(=O)NHC(=O)R^{11}$;

$C_1$–$C_6$ alkyl substituted with 0–3 $R^{9c}$;
$C_2$–$C_6$ alkenyl substituted with 0–3 $R^{9c}$;
$C_2$–$C_6$ alkynyl substituted with 0–3 $R^{9c}$;
$C_3$–$C^{10}$ cycloalkyl substituted with 0–4 $R^{9d}$;
aryl substituted with 0–5 $R^{9d}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^9c$ is selected from the group: $CF_3$, $OCF_3$, Cl, F, Br, I, =O, OH, $C(O)OR^{11}$, $NH_2$, $NH(CH_3)$, $N(CH_3)_2$, —CN, $NO_2$;

phenyl substituted with 0–5 $R^{9d}$;
naphthyl substituted with 0–5 $R^{9d}$;
benzyl substituted with 0–5 $R^{9d}$; and
5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^{9d}$ is selected at each occurrence from the group:
$CF_3$, $OCF_3$, Cl, F, Br, I, =O, OH, $C(O)OR^{11}$, $NH_2$, $NH(CH_3)$, $N(CH_3)_2$, —CN, $NO_2$;
$C_1$–$C_4$ alkyl substituted with 0–3 $R^{9e}$;
$C_1$–$C_4$ alkoxy substituted with 0–3 $R^{9e}$;
$C_3$–$C_6$ cycloalkyl substituted with 0–3 $R^{9e}$;
aryl substituted with 0–5 $R^{9e}$; and
5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–4 $R^{9e}$;

$R^{9e}$ is selected at each occurrence from the group:
$C_1$–$C_4$ alkyl, $C_1$–$C_4$ alkoxy, $CF_3$, $OCF_3$, Cl, F, Br, I, =O, OH, phenyl, $C(O)OR^{11}$, $NH_2$, $NH(CH_3)$, $N(CH_3)_2$, —CN, and $NO_2$;

$R^{10}$ is selected from the group: —$CO_2R^{11}$, —$NR^{11}R^{11a}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, $NR^{11}R^{11a}$, —$OR^{11}$, —$SR^{11}$, —$C(=NH)NH_2$, and aryl substituted with 0–1 $R^{10b}$;

$R^{10b}$ is selected from the group: —$CO_2H$, —$NH_2$, —OH, —SH, and —$C(=NH)NH_2$;

$R^{10c}$ is H or $C_1$–$C_4$ alkyl; alternatively, $R^{10}$ and $R^{10c}$ can be combined to form a $C_3$–$C_6$ cycloalkyl group substituted with 0–1 $R^{10a}$;

$R^{11}$ and $R^{11a}$ are, at each occurrence, independently selected from the group: H;
$C_1$–$C_6$ alkyl substituted with 0–3 $R^{11b}$;
$C_2$–$C_6$ alkenyl substituted with 0–3 $R^{11b}$;
$C_2$–$C_6$ alkynyl substituted with 0–3 $R^{11b}$;
$C_3$–$C_7$ cycloalkyl substituted with 0–3 $R^{11b}$;
aryl substituted with 0–3 $R^{11b}$; and
aryl($C_1$–$C_4$ alkyl)-substituted with 0–3 $R^{11b}$;

$R^{11b}$ is OH, $C_1$–$C_4$ alkoxy, F, Cl, Br, I, $NH_2$, or —NH($C_1$–$C_4$ alkyl);

$R^{12}$ is H or $C_1$–$C_4$ alkyl;

$R^{13}$ is selected from the group: H, $C_1$–$C_4$ alkyl, $C_2$–$C_4$ alkenyl, $C_2$–$C_4$ alkynyl, $C_3$–$C_6$ cycloalkyl, $C_3$–$C_6$ cycloalkyl($C_1$–$C_4$ alkyl), aryl and aryl-$C_1$–$C_4$ alkyl;

alternatively, $R^3$ and $R^{13}$ can be combined to form a 4–7 membered cyclic group consisting of carbon atoms, optionally substituted with $C_1$–$C_4$ alkyl; or $R^3$+$R^{13}$ is =$CR^4$;

$R^{19}$ and $R^{19a}$ are independently selected from the group: H, $C_1$–$C_4$ alkyl, $C_1$–$C_4$ haloalkyl, aryl, aryl($C_1$–$C_4$ alkyl), $C_3$–$C_6$ cycloalkyl, and $C_3$–$C_6$ cycloalkyl($C_1$–$C_4$ alkyl);

alternatively, $NR^{19}R^{19a}$ may form a 5–6 membered heterocyclic group consisting of carbon atoms, a nitrogen atom, and optionally a second heteroatom selected from the group: O, S, and N;

$R^{20}$ and $R^{20a}$ are independently selected from the group: H, $C_1$–$C_4$ alkyl, $C_1$–$C_4$ haloalkyl, aryl, aryl($C_1$–$C_4$ alkyl)—, $C_3$–$C_6$ cycloalkyl, and $C_3$–$C_6$ cycloalkyl($C_1$–$C_4$ alkyl)-;

alternatively, $NR^{20}R^{20a}$ may form a 5–6 membered heterocyclic group consisting of carbon atoms, a nitrogen atom, and optionally a second heteroatom selected from the group: O, S, and N;

$OR^{26}$ and $OR^{27}$ are independently selected from:
a) —OH,
b) —F,
c) —$NR^{28}R^{29}$,
d) $C_1$–$C_8$ alkoxy, and when taken together, $OR^{26}$ and $OR^{27}$ form:
e) a cyclic boronic ester where said cyclic boronic ester contains from 2 to 20 carbon atoms and, optionally, 1, 2, or 3 heteroatoms which can be N, S, or O;
f) a cyclic boronic amide where said boronic amide contains from 2 to 20 carbon atoms and, optionally, 1, 2, or 3 heteroatoms which can be N, S, or O; or
g) a cyclic boronic amide-ester where said boronic amide-ester contains from 2 to 20 carbon atoms and, optionally, 1, 2, or 3 heteroatoms which can be N, S, or O;

$R^{28}$ and $R^{29}$, are independently selected from: H, $C_1$–$C_4$ alkyl, aryl($C_1$–$C_4$ alkyl)-, and $C_3$–$C_7$ cycloalkyl;

$A^4$, $A^5$, $A^6$, $A^7$, $A^8$, and $A^9$ are independently selected from an amino acid residue; and an amino acid residue, at each occurence, independently comprises a natural amino acid, a modified amino acid or an unnatural amino acid wherein said natural, modified or unnatural amino acid is of either D or L configuration.

[2] In another embodiment, the present invention provides a compound of Formula (I) or a pharmaceutically acceptable salt or prodrug thereof, wherein:

$A^1$ is —$CH_2$—, —$CH_2CH_2$—, or —$CH_2CH_2CH_2$—;

$A^3$ is H, —C(=O)$R^{9a}$, —O$R^{9a}$, —S$R^{9a}$, —S(=O)$R^{9a}$, —S(=O)$_2R^{9a}$, —NHCO$R^{9a}$, —CONH$R^{9a}$, —NHS(=O)$_2R^{9a}$, —S(=O)$_2$NH$R^{9a}$, —NHC(=O)O$R^{9a}$, —OC(=O)NH$R^{9a}$, —C(=O)O$R^{9a}$, —O—C(=O)$R^{9a}$, —N$R^8R^{9a}$;

—NH—$A^4$—$R^{9b}$;

—NH—$A^4$—$A^5$—$R^{9b}$; or

—NH—$A^4$—$A^5$—$A^6$—$R^{9b}$;

W is selected from the group:
—B(O$R^{26}$)(O$R^{27}$),
—C(=O)C(=O)—Q,
—C(=O)C(=O)NH—Q,
—C(=O)C(=O)—O—Q,
—C(=O)CF$_2$C(=O)NH—Q,
—C(=O)Q$^3$,
—C(=O)CF$_3$,
—C(=O)CF$_2$CF$_3$, and
—C(=O)H;

Q is selected from the group:
—(C$R^{10}R^{10c}$)$_m$—Q$^1$,
—(C$R^{10}R^{10c}$)$_m$—Q$^2$,
$C_1$–$C_4$ alkyl substituted with Q$^1$,
$C_2$–$C_4$ alkenyl substituted with Q$^1$,
$C_2$–$C_4$ alkynyl substituted with Q$^1$,
an amino acid residue,
—$A^7$—$A^8$, and
—$A^7$—$A^8$—$A^9$;

m is 1, 2, or 3;

Q$^1$ is selected from the group:
—CO$_2R^{11}$, —SO$_2R^{11}$, —SO$_3R^{11}$, —P(O)$_2R^{11}$, —P(O)$_3R^{11}$; aryl substituted with 0–4 Q$^{1a}$; and 5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–4 Q$^{1a}$;

Q$^{1a}$ is H, F, Cl, Br, I, —NO$_2$, —CN, —NCS, —CF$_3$, —OCF$_3$, —CO$_2R^{19}$, —C(=O)N$R^{19}R^{9a}$, —NHC(=O)$R^{19}$, —SO$_2R^{19}$, —SO$_2$N$R^{19}R^{19a}$, —N$R^{19}R^{19a}$, —O$R^{19}$, —S$R^{19}$, $C_1$–$C_4$ alkyl, $C_1$–$C_4$ alkoxy, $C_1$–$C_4$ haloalkyl, or $C_1$–$C_4$ haloalkoxy;

Q$^2$ is —X—N$R^{12}$—Z, —N$R^{12}$—Y—Z, or —X—N$R^{12}$—Y—Z;

Q$^3$ is aryl substituted with 0–3 Z$^c$; or

5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 Z$^c$;

X is —C(=O)—, —S—, —S(=O)—, —S(=O)$_2$—, —P(O)—, —P(O)$_2$—, or —P(O)$_3$—;

Y is —C(=O)—, —S—, —S(=O)—, —S(=O)$_2$—, —P(O)—, —P(O)$_2$—, or —P(O)$_3$—;

Z is selected from the group:
$C_1$–$C_4$ haloalkyl;
$C_1$–$C_4$ alkyl substituted with 0–3 Z$^a$;
$C_2$–$C_4$ alkenyl substituted with 0–3 Z$^a$;
$C_2$–$C_4$ alkynyl substituted with 0–3 Z$^a$;
$C_3$–$C_{10}$ cycloalkyl substituted with 0–5 Z$^b$;
aryl substituted with 0–5 Z$^b$; and 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 Z$^b$;

Z$^a$ is selected from the group:
H, F, Cl, Br, I, —NO$_2$, —CN, —NCS, —CF$_3$, —OCF$_3$, —CO$_2R^{20}$, C(=O)N$R^{20}R^{20a}$, —NHC(=O)$R^{20}$, —N$R^{20}R^{20a}$, —O$R^{20}$, —S$R^{20}$, —S(=O)$R^{20}$, —SO$_2R^{20}$, —SO$_2$N$R^{20}R^{20a}$, $C_1$–$C_4$ alkyl, $C_1$–$C_4$ haloalkyl, $C_1$–$C_4$ haloalkoxy;
$C_3$–$C_{10}$ cycloalkyl substituted with 0–5 Z$^b$;
$C_3$–$C_{10}$ carbocyle substituted with 0–5 Z$^b$;
aryl substituted with 0–5 Z$^b$; and 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 Z$^b$;

Z$^b$ is selected from the group:
H, F, Cl, Br, I, —NO$_2$, —CN, —NCS, —CF$_3$, —OCF$_3$, —CO$_2R^{20}$, —C(=O)N$R^{20}R^{20a}$, —NHC(=O)$R^{20}$, —N$R^{20}R^{20a}$, —O$R^{20}$, —S$R^{20}$, —S(=O)$R^{20}$, —SO$_2R^{20}$, —SO$_2$N$R^{20}R^{20a}$, $C_1$–$C_4$ alkyl, $C_1$–$C_4$ haloalkyl, $C_1$–$C_4$ haloalkoxy;
$C_3$–$C_{10}$ cycloalkyl substituted with 0–5 Z$^c$;
$C_3$–$C_{10}$ carbocyle substituted with 0–5 Z$^c$;
aryl substituted with 0–5 Z$^c$; and 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 Z$^c$;

Z$^c$ is H, F, Cl, Br, I, —NO$_2$, —CN, —NCS, —CF$_3$, —OCF$_3$, —CO$_2R^{20}$, —C(=O)N$R^{20}R^{20a}$, —NHC(=O)$R^{20}$, —N$R^{20}R^{20a}$, —O$R^{20}$, —S$R^{20}$, —S(=O)$R^{20}$, —SO$_2R^{20}$, —SO$_2$N$R^{20}R^{20a}$, $C_1$–$C_4$ alkyl, $C_1$–$C_4$ haloalkyl, or $C_1$–$C_4$ haloalkoxy;

$R^1$ is selected from the group: H, F;
$C_1$–$C_6$ alkyl substituted with 0–3 $R^{1a}$;
$C_2$–$C_6$ alkenyl substituted with 0–3 $R^{1a}$;
$C_2$–$C_6$ alkynyl substituted with 0–3 $R^{1a}$; and
$C_3$–$C_6$ cycloalkyl substituted with 0–3 $R^{1a}$;

$R^{1a}$ is selected at each occurrence from the group:
Cl, F, Br, I, CF$_3$, CHF$_2$, OH, =O, SH, —CO$_2R^{1b}$, —SO$_2R^{1b}$, —SO$_3R^{1b}$, —P(O)$_2R^{1b}$, —P(O)$_3R^{1b}$, —C(=O)NH$R^{1b}$, —NHC(=O)$R^{1b}$, —SO$_2$NH$R^{1b}$, —O$R^{1b}$, —S$R^{1b}$, $C_3$–$C_6$ cycloalkyl, $C_1$–$C_6$ alkoxy, —S—($C_1$–$C_6$ alkyl);
$C_1$–$C_4$ alkyl substituted with 0–3 $R^{1c}$;
aryl substituted with 0–5 $R^{1c}$;
—O—(CH$_2$)$_n$-aryl substituted with 0–5 $R^{1c}$;
—S—(CH$_2$)$_n$-aryl substituted with 0–5 $R^{1c}$; and 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{1c}$;

n is 0, 1 or 2;

$R^{1b}$ is H;
  $C_1$–$C_4$ alkyl substituted with 0–3 $R^{1c}$;
  $C_2$–$C_4$ alkenyl substituted with 0–3 $R^{1c}$;
  $C_2$–$C_4$ alkynyl substituted with 0–3 $R^{1c}$;
  $C_3$–$C_6$ cycloalkyl substituted with 0–5 $R^{1c}$;
  aryl substituted with 0–5 $R^{1c}$;
  aryl-$C_1$–$C_4$ alkyl substituted with 0–4 $R^{1c}$; or
  5–6 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{1c}$;

$R^{1c}$ is selected at each occurrence from the group: $C_1$–$C_4$ alkyl, Cl, F, Br, I, OH, SH, —CN, —NO$_2$, —OR$^{1d}$, —C(=O)OR$^{1d}$, —NR$^{1d}$R$^{1d}$, —SO$_2$R$^{1d}$, —SO$_3$R$^{1d}$, —C(=O)NHR$^{1d}$, —NHC(=O)R$^{1d}$, —SO$_2$NHR$^{1d}$, —CF$_3$, —OCF$_3$, $C_3$–$C_6$ cycloalkyl, phenyl, and benzyl;

$R^{1d}$ is selected at each occurrence from the group: H, $C_1$–$C_4$ alkyl, phenyl and benzyl;

$R^2$ is H, methyl or ethyl;

$R^3$ is selected from the group: $R^4$,
  —(CH$_2$)$_p$—NH—R$^4$,
  —(CH$_2$)$_p$—NHC(=O)—R$^4$,
  —(CH$_2$)$_p$—C(=O)NH—R$^4$,
  —(CH$_2$)$_p$—C(=O)O—R$^4$,
  —(CH$_2$)$_p$—C(=O)C(=O)—R$^4$,
  —(CH$_2$)$_p$—C(=O)C(=O)NH—R$^4$,
  —(CH$_2$)$_p$—NHC(=O)NH—R$^4$,
  —(CH$_2$)$_p$—NHC(=O)NHC(=O)—R$^4$,
  —(CH$_2$)$_p$—NHS(=O)$_2$—R$^4$,
  —(CH$_2$)$_p$—S(=O)$_2$NH—R$^4$,
  —(CH$_2$)$_p$—C(=O)—R$^4$,
  —(CH$_2$)$_p$—O—R$^4$, and
  —(CH$_2$)$_p$—S—R$^4$;

p is 0, 1, or 2;

$R^4$ is selected from the group:
  $C_1$–$C_6$ alkyl substituted with 0–3 $R^{4a}$;
  $C_2$–$C_6$ alkenyl substituted with 0–3 $R^{4a}$;
  $C_2$–$C_6$ alkynyl substituted with 0–3 $R^{4a}$;
  $C_3$–$C_{10}$ cycloalkyl substituted with 0–4 $R^{4b}$;
  aryl substituted with 0–5 $R^{4b}$; aryl-$C_1$–$C_4$ alkyl substituted with 0–5 $R^{4b}$; and
  5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{4b}$;

$R^{4a}$ is, at each occurrence, independently selected from: H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, NR$^{11}$R$^{11a}$, OR$^{11a}$, —SR$^{11a}$, —C(=O)R$^{11a}$, —S(=O)R$^{11a}$, —SO$_2$R$^{11}$, —SO$_2$NR$^{11}$R$^{11a}$, —NHC(=NH)NHR$^{11}$, —C(=NH)NHR$^{11}$, =NOR$^{11}$, —NR$^{11}$C(=O)OR$^{11a}$, —NR$^{11}$C(=O)NR$^{11}$R$^{11a}$, —NR$^{11}$SO$_2$NR$^{11}$R$^{11a}$, —NR$^{11}$SO$_2$R$^{11a}$, —OP(O)(OR$^{11}$)$_2$;
  $C_1$–$C_4$ alkyl substituted with 0–2 $R^{4b}$;
  $C_2$–$C_4$ alkenyl substituted with 0–2 $R^{4b}$;
  $C_2$–$C_4$ alkynyl substituted with 0–2 $R^{4b}$;
  $C_3$–$C_7$ cycloalkyl substituted with 0–3 $R^{4c}$;
  aryl substituted with 0–5 $R^{4c}$; and
  5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{4c}$;

$R^{4b}$ is, at each occurrence, independently selected from: H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O)R$^{11a}$, —SO$_2$R$^{11}$, SO$_2$NR$^{11}$R$^{11a}$, —NHC(=NH)NHR$^{11}$, —C(=NH)NHR$^{11}$, =NOR$^{11}$, —NR$^{11}$C(=O)OR$^{11a}$, —OC(=O)NR$^{11}$R$^{11a}$, —NR$^{11}$C(=O)NR$^{11}$R$^{11a}$, —NR$^{11}$SO$_2$NR$^{11}$R$^{11a}$, —NR$^{11}$SO$_2$R$^{11a}$, —OP(O)(OR$^{11}$)$_2$;
  $C_1$–$C_4$ alkyl substituted with 0–3 $R^{4c}$;
  $C_2$–$C_4$ alkenyl substituted with 0–3 $R^{4c}$;
  $C_2$–$C_4$ alkynyl substituted with 0–3 $R^{4c}$;
  $C_3$–$C_6$ cycloalkyl substituted with 0–4 $R^{4d}$;
  aryl substituted with 0–5 $R^{4d}$; and
  5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4c}$ is, at each occurrence, independently selected from: H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O) R$^{11a}$, —SO$_2$R$^{11}$, —SO$_2$NR$^{11}$R$^{11a}$, $C_1$–$C_4$ haloalkyl, $C_1$–$C_4$ haloalkoxy;
  $C_1$–$C_4$ alkyl substituted with 0–3 $R^{4d}$;
  $C_2$–$C_4$ alkenyl substituted with 0–3 $R^{4d}$;
  $C_2$–$C_4$ alkynyl substituted with 0–3 $R^{4d}$;
  $C_3$–$C_6$ cycloalkyl substituted with 0–4 $R^{4d}$;
  aryl substituted with 0–5 $R^{4d}$; and
  5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4d}$ is, at each occurrence, independently selected from: H, F, Cl, Br, I, —NO$_2$, —CN, —NCS, —CF$_3$, —OCF$_3$, =O, OH, —CO$_2$H, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11a}$, $C_1$–$C_4$ alkyl, $C_1$–$C_4$ alkoxy, $C_1$–$C_4$ haloalkyl, $C_1$–$C_4$ haloalkoxy, phenyl, and benzyl;

$R^6$ is selected from the group: H, $C_1$–$C_6$ alkyl, $C_2$–$C_6$ alkenyl, $C_2$–$C_6$ alkynyl, $C_3$–$C_6$ cycloalkyl, aryl, and 5–6 membered heterocyclic group consisting of carbon atoms and 1–4 heteroatoms selected from the group: O, S, and N; optionally saturated, partially unsaturated or unsaturated;

$R^{6a}$ is selected from the group: H, F, Cl, Br, I, —CO$_2$R$^{11}$, NR$^{11}$R$^{11a}$, —OR$^{11}$, —SR$^{11}$, —C(=NH)NH$_2$, $C_1$–$C_4$ alkyl, $C_1$–$C_4$ haloalkyl, $C_3$–$C_6$ cycloalkyl;
  aryl substituted with 0–3 $R^{6b}$; and
  5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–3 $R^{6b}$;

$R^6$b is selected from the group: H, F, Cl, Br, I, —CO$_2$R$^{11}$, NR$^{11}$R$^{11a}$, —OR$^{11}$, —SR$^{11}$, —C(=NH)NH$_2$, $C_1$–$C_4$ alkyl, and $C_1$–$C_4$ haloalkyl;

$R^8$ is H, $C_1$–$C_4$ alkyl, $C_2$–$C_4$ alkenyl, $C_2$–$C_4$ alkynyl, $C_3$–$C_4$ cycloalkyl, phenyl or benzyl;

$R^{9a}$ is selected from the group: H;
- $C_1$–$C_6$ alkyl substituted with 0–3 $R^{9c}$;
- $C_2$–$C_6$ alkenyl substituted with 0–3 $R^{9c}$;
- $C_2$–$C_6$ alkynyl substituted with 0–3 $R^{9c}$;
- $C_3$–$C_6$ cycloalkyl substituted with 0–3 $R^{9d}$;
- aryl substituted with 0–5 $R^{9d}$; and
- 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^{9b}$ is selected from the group: H, —S(=O)$R^{11}$, —S(=O)$_2R^{11}$, —S(=O)$_2$NH$R^{11}$, —C(=O)$R^{11}$, —C(=O)O$R^{11}$, —C(=O)NH$R^{11}$; —C(=O)NHC(=O)$R^{11}$;
- $C_1$–$C_6$ alkyl substituted with 0–3 $R^{9c}$;
- $C_2$–$C_6$ alkenyl substituted with 0–3 $R^{9c}$;
- $C_2$–$C_6$ alkynyl substituted with 0–3 $R^{9c}$;
- $C_3$–$C_{10}$ cycloalkyl substituted with 0–4 $R^{9d}$;
- aryl substituted with 0–5 $R^{9d}$; and
- 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^{9c}$ is selected from the group: $CF_3$, $OCF_3$, Cl, F, Br, I, =O, OH, C(O)O$R^{11}$, $NH_2$, NH($CH_3$), N($CH_3$)$_2$, —CN, $NO_2$;
- phenyl substituted with 0–5 $R^{9d}$;
- naphthyl substituted with 0–5 $R^{9d}$;
- benzyl substituted with 0–5 $R^{9d}$; and
- 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{9d}$;

$R^{9d}$ is selected at each occurrence from the group: $CF_3$, $OCF_3$, Cl, F, Br, I, =O, OH, C(O)O$R^{11}$, $NH_2$, NH($CH_3$), N($CH_3$)$_2$, —CN, $NO_2$;
- $C_1$–$C_4$ alkyl substituted with 0–3 $R^{9e}$,
- $C_1$–$C_4$ alkoxy substituted with 0–3 $R^{9e}$,
- $C_3$–$C_6$ cycloalkyl substituted with 0–3 $R^{9e}$,
- aryl substituted with 0–5 $R^{9e}$, and
- 5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–4 $R^{9e}$;

$R^{9e}$ is selected at each occurrence from the group: $C_1$–$C_4$ alkyl, $C_1$–$C_4$ alkoxy, $CF_3$, $OCF_3$, Cl, F, Br, I, =O, OH, phenyl, C(O)O$R^{11}$, $NH_2$, NH($CH_3$), N($CH_3$)$_2$, —CN, and $NO_2$;

$R^{10}$ is selected from the group: —$CO_2R^{11}$, —$NR^{11}R^{11a}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, $NR^{11}R^{11a}$, —$OR^{11}$, —$SR^{11}$, —C(=NH)$NH_2$, and aryl substituted with 0–1 $R^{10b}$;

$R^{10b}$ is selected from the group: —$CO_2$H, —$NH_2$, —OH, —SH, and —C(=NH)$NH_2$;

$R^{10c}$ is H or $C_1$–$C_4$ alkyl;

alternatively, $R^{10}$ and $R^{10c}$ can be combined to form a $C_3$–$C_6$ cycloalkyl group substituted with 0–1 $R^{10a}$;

$R^{11}$ and $R^{11a}$ are, at each occurrence, independently selected from the group: H,
- $C_1$–$C_6$ alkyl substituted with 0–3 $R^{11b}$,
- $C_2$–$C_6$ alkenyl substituted with 0–3 $R^{11b}$;
- $C_2$–$C_6$ alkynyl substituted with 0–3 $R^{11b}$;
- $C_3$–$C_7$ cycloalkyl substituted with 0–3 $R^{11b}$;
- aryl substituted with 0–3 $R^{11b}$; and
- aryl($C_1$–$C_4$ alkyl)-substituted with 0–3 $R^{11b}$;

$R^{11b}$ is OH, $C_1$–$C_4$ alkoxy, F, Cl, Br, I, $NH_2$, or —NH($C_1$–$C_4$ alkyl);

$R^{12}$ is H or $C_1$–$C_4$ alkyl;

$R^{13}$ is selected from the group: H, $C_1$–$C_4$ alkyl, $C_2$–$C_4$ alkenyl, $C_2$–$C_4$ alkynyl, $C_3$–$C_6$ cycloalkyl, $C_3$–$C_6$ cycloalkyl($C_1$–$C_4$ alkyl), aryl and aryl-$C_1$–$C_4$ alkyl;

alternatively, $R^3$ and $R^{13}$ can be combined to form a 4–7 membered cyclic group consisting of carbon atoms, optionally substituted with $C_1$–$C_4$ alkyl; or $R^3+R^{13}$ is =$CR^4$;

$R^{19}$ and $R^{19a}$ are independently selected from the group: H, $C_1$–$C_4$ alkyl, $C_1$–$C_4$ haloalkyl, aryl, aryl($C_1$–$C_4$ alkyl), $C_3$–$C_6$ cycloalkyl, and $C_3$–$C_6$ cycloalkyl($C_1$–$C_4$ alkyl);

alternatively, $NR^{19}R^{19a}$ may form a 5–6 membered heterocyclic group consisting of carbon atoms, a nitrogen atom, and optionally a second heteroatom selected from the group: O, S, and N;

$R^{20}$ and $R^{20a}$ are independently selected from the group: H, $C_1$–$C_4$ alkyl, $C_1$–$C_4$ haloalkyl, aryl, aryl($C_1$–$C_4$ alkyl)-, $C_3$–$C_6$ cycloalkyl, and $C_3$–$C_6$ cycloalkyl($C_1$–$C_4$ alkyl)-;

alternatively, $NR^{20}R^{20a}$ may form a 5–6 membered heterocyclic group consisting of carbon atoms, a nitrogen atom, and optionally a second heteroatom selected from the group: O, S, and N;

$OR^{26}$ and $OR^{27}$ are independently selected from:
a) —OH,
b) —F,
c) —$NR^{28}R^{29}$,
d) $C_1$–$C_8$ alkoxy, and
when taken together, $OR^{26}$ and $OR^{27}$ form:
e) a cyclic boronic ester where said cyclic boronic ester contains from 2 to 20 carbon atoms, and, optionally, 1, 2, or 3 heteroatoms which can be N, S, or O;

$R^{28}$ and $R^{29}$, are independently selected from: H, $C_1$–$C_4$ alkyl, aryl($C_1$–$C_4$ alkyl)-, and $C_3$–$C_7$ cycloalkyl;

$A^4$, $A^5$, $A^6$, $A^7$, $A^8$, and $A^9$ are independently selected from an amino acid residue; and an amino acid residue, at each occurence, independently comprises a natural amino acid, a modified amino acid or an unnatural amino acid wherein said natural, modified or unnatural amino acid is of either D or L configuration.

[3] In an alternative embodiment, the present invention provides a compound of Formula (I) or a pharmaceutically acceptable salt or prodrug thereof, wherein:

$A^1$ is —$CH_2$— or —$CH_2CH_2$—;

$A^3$ is H, —C(=O)$R^{9a}$, —O$R^{9a}$, —S$R^{9a}$, —S(=O)$R^{9a}$, —S(=O)$_2R^{9a}$, —NHCO$R^{9a}$, —CONH$R^{9a}$, —NHS(=O)$_2R^{9a}$, —S(=O)$_2$NH$R^{9a}$, —NHC(=O)O$R^{9a}$, —OC(=O)NH$R^{9a}$, —C(=O)O$R^{9a}$, —O—C(=O)$R^{9a}$, —N$R^8R^{9a}$;
—NH—$A^4$—$R^{9b}$; or
—NH—$A^4$—$A^5$—$R^{9b}$;

W is —B($OR^{26}$)($OR^{27}$);

$R^1$ is selected from the group: H;
- $C_1$–$C_4$ alkyl substituted with 0–2 $R^{1a}$;
- $C_2$–$C_4$ alkenyl substituted with 0–2 $R^{1a}$; and
- $C_2$–$C_4$ alkynyl substituted with 0–2 $R^{1a}$;

$R^{1a}$ is selected at each occurrence from the group:
  Cl, F, Br, $CF_3$, $CHF_2$, OH, $C_3$–$C_6$ cycloalkyl, $C_1$–$C_6$ alkoxy, —S—($C_1$–$C_6$ alkyl);
  $C_1$–$C_4$ alkyl substituted with 0–2 $R^{1c}$;
  aryl substituted with 0–3 $R^{1c}$; and
  5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{1c}$;

$R^{1c}$ is selected at each occurrence from the group: $C_1$–$C_4$ alkyl, Cl, F, Br, I, OH, SH, —CN, —$NO_2$, —$OR^{1d}$, —C(=O)$OR^{1d}$, —$NR^{1d}R^{1d}$, —$SO_2R^{1d}$, —$SO_3R^{1d}$, —C(=O)$NHR^{1d}$, —NHC(=O)$R^{1d}$, —$SO_2NHR^{1d}$, —$CF_3$, —$OCF_3$, $C_3$–$C_6$ cycloalkyl, phenyl, and benzyl;

$R^{1d}$ is selected at each occurrence from the group: H, $C_1$–$C_4$ alkyl, phenyl and benzyl;

$R^2$ is H;

$R^3$ is selected from the group: $R^4$,
  —$(CH_2)_p$—NH—$R^4$,
  —$(CH_2)_p$—NHC(=O)—$R^4$,
  —$(CH_2)_p$—C(=O)NH—$R^4$,
  —$(CH_2)_p$—C(=O)O—$R^4$,
  —$(CH_2)_p$—NHC(=O)NH—$R^4$,
  —$(CH_2)_p$—NHC(=O)NHC(=O)—$R^4$,
  —$(CH_2)_p$—C(=O)—$R^4$,
  —$(CH_2)_p$—O—$R^4$, and
  —$(CH_2)_p$—S—$R^4$;

p is 0, 1, or 2;

$R^4$ is selected from the group:
  $C_1$–$C_4$ alkyl substituted with 0–3 $R^{4a}$;
  $C_2$–$C_4$ alkenyl substituted with 0–3 $R^{4a}$;
  $C_2$–$C_4$ alkynyl substituted with 0–3 $R^{4a}$;
  $C_3$–$C_6$ cycloalkyl substituted with 0–2 $R^{4b}$;
  aryl substituted with 0–5 $R^{4b}$; and
  5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 $R^{4b}$;

$R^{4a}$ is, at each occurrence, independently selected from:
  H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, $OR^{11a}$, —$SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}$C(=O)$OR^{11a}$, —$NR^{11}$C(=O)$NR^{11}R^{11a}$, —$NR^{11}SO_2NR^{11}R^{11a}$, —$NR^{11}SO_2R^{11a}$;
  $C_1$–$C_4$ alkyl substituted with 0–2 $R^{4b}$;
  $C_2$–$C_4$ alkenyl substituted with 0–2 $R^{4b}$;
  $C_2$–$C_4$ alkynyl substituted with 0–2 $R^{4b}$;
  $C_3$–$C_7$ cycloalkyl substituted with 0–3 $R^{4c}$;
  aryl substituted with 0–5 $R^{4c}$; and
  5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{4c}$;

$R^{4b}$ is, at each occurrence, independently selected from:
  H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}$C(=O)$OR^{11a}$, —OC(=O)$NR^{11}R^{11a}$, —$NR^{11}$C(=O)$NR^{11}R^{11a}$, —$NR^{11}SO_2NR^{11}R^{11a}$, —$NR^{11}SO_2R^{11a}$, —OP(O)($OR^{11})_2$;
  $C_1$–$C_4$ alkyl substituted with 0–3 $R^{4c}$;
  $C_2$–$C_4$ alkenyl substituted with 0–3 $R^{4c}$;
  $C_2$–$C_4$ alkynyl substituted with 0–3 $R^{4c}$;
  $C_3$–$C_6$ cycloalkyl substituted with 0–4 $R^{4d}$;
  aryl substituted with 0–5 $R^{4d}$; and
  5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4c}$ is, at each occurrence, independently selected from:
  H, F, Cl, Br, I, —$NO_2$, —CN, —NCS, —$CF_3$, —CO $CF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O) $R^{11a}$, —$SO_2R^{11}$, —$SO_2NR^{11}R^{11a}$, $C_1$–$C_4$ haloalkyl, $C_1$–$C_4$ haloalkoxy;
  $C_1$–$C_4$ alkyl substituted with 0–3 $R^{4d}$;
  $C_2$–$C_4$ alkenyl substituted with 0–3 $R^{4d}$;
  $C_2$–$C_4$ alkynyl substituted with 0–3 $R^{4d}$;
  $C_3$–$C_6$ cycloalkyl substituted with 0–4 $R^{4d}$;
  aryl substituted with 0–5 $R^{4d}$; and
  5–10 membered heterocyclic group consisting of carbon atoms and 1–4 heteroatoms selected from the group: O, S, and N; optionally saturated or unsaturated; and said 5–10 membered heterocyclic group is substituted with 0–3 $R^{4d}$;

$R^{4d}$ is, at each occurrence, independently selected from:
  H, F, Cl, Br, I, —$NO_2$, —CN, —NCS, —$CF_3$, —$OCF_3$, =O, OH, —$CO_2H$, —$CO_2R^{11}$, —C(=O)$NR^{11}R^{11a}$, —NHC(=O) $R^{11}$, —$NR^{11}R^{11a}$, —$OR^{11a}$, $SR^{11a}$, —C(=O)$R^{11a}$, —S(=O)$R^{11a}$, —$SO_2R^{11}$, —$SO_2NR^{11}R^{11a}$, $C_1$–$C_4$ alkyl, $C_1$–$C_4$ alkoxy, $C_1$–$C_4$ haloalkyl, $C_1$–$C_4$ haloalkoxy, phenyl, and benzyl;

$R^6$ is H or $C_1$–$C_6$ alkyl;

$R^8$ is H, methyl, ethyl, propyl, or butyl;

$R^{9a}$ is selected from the group: H;
  $C_1$–$C_4$ alkyl substituted with 0–2 $R^{9c}$;
  $C_2$–$C_4$ alkenyl substituted with 0–2 $R^{9c}$;
  $C_2$–$C_4$ alkynyl substituted with 0–2 $R^{9c}$;
  $C_3$–$C_6$ cycloalkyl substituted with 0–2 $R^{9d}$;
  phenyl substituted with 0–3 $R^{9d}$; and
  5–6 membered heterocyclic group consisting of carbon atoms and 1–4 heteroatoms selected from the group: O, S, and N; optionally saturated, partially unsaturated or unsaturated; and said heterocyclic group is substituted with 0–3 $R^{9d}$;

$R^{9b}$ is selected from the group: H, —S(=O)$R^{11}$, —S(=O)$_2R^{11}$, —S(=O)$_2NHR^{11}$, —C(=O)$R^{11}$, —C(=O)$OR^{11}$, —C(=O)$NHR^{11}$; —C(=O)NHC(=O)$R^{11}$;
  $C_1$–$C_4$ alkyl substituted with 0–2 $R^{9c}$;
  $C_2$–$C_4$ alkenyl substituted with 0–2 $R^{9c}$;
  $C_2$–$C_4$ alkynyl substituted with 0–2 $R^{9c}$;
  $C_3$–$C_6$ cycloalkyl substituted with 0–2 $R^{9d}$;
  aryl substituted with 0–5 $R^{9d}$; and
  5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 $R^{9d}$;

$R^{9c}$ is selected from the group: $CF_3$, $OCF_3$, Cl, F, Br, OH, $C(O)OR^{11}$, $NH_2$, $NH(CH_3)$, $N(CH_3)_2$, —CN, $NO_2$, phenyl and benzyl;

$R^{9d}$ is selected at each occurrence from the group:
$CF_3$, $OCF_3$, Cl, F, Br, OH, $C(O)OR^{11}$, $NH_2$, $NH(CH_3)$, $N(CH_3)_2$, —CN, $NO_2$;
$C_1$–$C_4$ alkyl substituted with 0–1 $R^{9e}$,
$C_1$–$C_4$ alkoxy substituted with 0–1 $R^{9e}$,
$C_3$–$C_6$ cycloalkyl substituted with 0–1 $R^{9e}$,
phenyl substituted with 0–3 $R^{9e}$, and
5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–3 $R^{9e}$;

$R^{9e}$ is selected at each occurrence from the group:
$C_1$–$C_4$ alkyl, $C_1$–$C_4$ alkoxy, $CF_3$, $OCF_3$, Cl, F, Br, OH, phenyl, $C(O)OR^{11}$, $NH_2$, $NH(CH_3)$, $N(CH_3)_2$, —CN, and $NO_2$;

$R^{11}$ and $R^{11a}$ are, at each occurrence, independently selected from the group: H,
$C_1$–$C_4$ alkyl substituted with 0–1 $R^{11b}$,
phenyl substituted with 0–2 $R^{11b}$; and
benzyl substituted with 0–2 $R^{11b}$;

$R^{11b}$ is OH, $C_1$–$C_4$ alkoxy, F, Cl, Br, I, $NH_2$, or —NH($C_1$–$C_4$ alkyl);

$R^{13}$ is selected from the group: H, $C_1$–$C_4$ alkyl, $C_2$–$C_4$ alkenyl, $C_2$–$C_4$ alkynyl, $C_3$–$C_6$ cycloalkyl, $C_3$–$C_6$ cycloalkyl($C_1$–$C_4$ alkyl), aryl and aryl-$C_1$–$C_4$ alkyl;

$OR^{26}$ and $OR^{27}$ are independently selected from:
a) —OH,
d) $C_1$–$C_8$ alkoxy, and when taken together, $OR^{26}$ and $OR^{27}$ form:
e) a cyclic boronic ester where said cyclic boronic ester contains from 2 to 16 carbon atoms;

$A^4$ and $A^5$ are independently selected from an amino acid residue wherein said amino acid residue, at each occurence, is independently selected from the group:
Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O'Bu), Glu(O'Bu), Hyp(O'Bu), Thr(O'Bu), Asp(OBzl), Glu(OBzl), Hyp(OBzl), Pro(OBzl), Thr(OBzl), cyclohexylglycine, cyclohexylalanine, cyclopropylglycine, t-butylglycine, phenylglycine, and 3,3-diphenylalanine.

[4] In another alternative embodiment, the present invention provides a compound of Formula (I) or a pharmaceutically acceptable salt or prodrug thereof, wherein:

$A^1$ is —$CH_2$—;
$A^3$ is H, —$NHCOR^{9a}$, —$CONHR^{9a}$, —$NHC(=O)OR^{9a}$, —$NR^8R^{9a}$; or —NH—$A^4$—$R^{9b}$;
W is —$B(OR^{26})(OR^{27})$;
$R^1$ is selected from the group: H;
$C_1$–$C_4$ alkyl substituted with 0–2 $R^{1a}$;
$C_2$–$C_4$ alkenyl substituted with 0–2 $R^{1a}$; and
$C_2$–$C_4$ alkynyl substituted with 0–2 $R^{1a}$;
$R^{1a}$ is selected at each occurrence from the group: Cl, F, Br, $CF_3$, and $CHF_2$;
$R^2$ is H;
$R^3$ is selected from the group: $R^4$,
—$(CH_2)_p$—NN—$R^4$,
—$(CH_2)_p$—NHC(=O)—$R^4$,
—$(CH_2)_p$—C(=O)NH—$R^4$,
—$(CH_2)_p$—C(=O)O—$R^4$,
—$(CH_2)_p$—NHC(=O)NH—$R^4$,
—$(CH_2)_p$—NHC(=O)NHC(=O)—$R^4$,
—$(CH_2)_p$—C(=O)—$R^4$,
—$(CH_2)_p$—O—$R^4$, and
—$(CH_2)_p$—S—$R^4$;

p is 0 or 1;
$R^4$ is selected from the group:
$C_1$–$C_4$ alkyl substituted with 0–3 $R^{4a}$;
$C_2$–$C_4$ alkenyl substituted with 0–3 $R^{4a}$;
$C_2$–$C_4$ alkynyl substituted with 0–3 $R^{4a}$;
$C_3$–$C_6$ cycloalkyl substituted with 0–2 $R^{4b}$;
phenyl substituted with 0–3 $R^{4b}$;
naphthyl substituted with 0–3 $R^{4b}$; and
5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4b}$;

$R^{4a}$ is, at each occurrence, independently selected from:
H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}C(=O)OR^{11a}$, —$NR^{11}C(=O)NR^{11}R^{11a}$, —$NR^{11}SO_2NR^{11}R^{11a}$, —$NR^{11}SO_2R^{11a}$;
$C_1$–$C_4$ alkyl substituted with 0–1 $R^{4b}$;
$C_2$–$C_4$ alkenyl substituted with 0–1 $R^{4b}$;
$C_2$–$C_4$ alkynyl substituted with 0–1 $R^{4b}$;
$C_3$–$C_7$ cycloalkyl substituted with 0–2 $R^{4c}$;
phenyl substituted with 0–3 $R^{4c}$;
naphthyl substituted with 0–3 $R^{4c}$; and
5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4c}$;

$R^{4b}$ is, at each occurrence, independently selected from:
H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}C(=O)OR^{11a}$, —OC(=O)$NR^{11}R^{11a}$, —$NR^{11}C(=O)NR^{11}R^{11a}$, —$NR^{11}SO_2NR^{11}R^{11a}$, —$NR^{11}SO_2R^{11a}$, —OP(O)($OR^{11})_2$;

$C_1$–$C_4$ alkyl substituted with 0–2 $R^{4c}$;
$C_2$–$C_4$ alkenyl substituted with 0–2 $R^{4c}$;
$C_2$–$C_4$ alkynyl substituted with 0–2 $R^{4c}$;
$C_3$–$C_6$ cycloalkyl substituted with 0–3 $R^{4d}$;
phenyl substituted with 0–3 $R^{4d}$;
naphthyl substituted with 0–3 $R^{4d}$; and
5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4d}$;

$R^{4c}$ is, at each occurrence, independently selected from: H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, $OR^{11a}$, $SR^{11a}$, —C(=O)$R^{11a}$, —S(=O)$R^{11a}$, —$SO_2R^{11}$, —$SO_2NR^{11}R^{11a}$, $C_1$–$C_4$ haloalkyl, $C_1$–$C_4$ haloalkoxy;
$C_1$–$C_4$ alkyl substituted with 0–1 $R^{4d}$;
$C_2$–$C_4$ alkenyl substituted with 0–1 $R^{4d}$;
$C_2$–$C_4$ alkynyl substituted with 0–1 $R^{4d}$;
$C_3$–$C_6$ cycloalkyl substituted with 0–2 $R^{4d}$;
phenyl substituted with 0–3 $R^{4d}$;
naphthyl substituted with 0–3 $R^{4d}$; and
5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4d}$;

$R^{4d}$ is, at each occurrence, independently selected from: H, F, Cl, Br, I, —$NO_2$, —CN, —NCS, —$CF_3$, —$OCF_3$, =O, OH, —$CO_2H$, —$CO_2R^{11}$, —C(=O)$NR^{11}R^{11a}$, —NHC(=O)$R^{11}$, —$NR^{11}R^{11a}$, —$OR^{11a}$, $SR^{11a}$, —C(=O)$R^{11a}$, —S(=O)$R^{11a}$, —$SO_2R^{11}$, —$SO_2NR^{11}R^{11a}$, $C_1$–$C_4$ alkyl, $C_1$–$C_4$ alkoxy, $C_1$–$C_4$ haloalkyl, $C_1$–$C_4$ haloalkoxy, phenyl, and benzyl;

$R^6$ is H, methyl, ethyl, propyl, or butyl;

$R^8$ is H or methyl;

$R^{9a}$ is selected from the group: H;
$C_1$–$C_4$ alkyl substituted with 0–1 $R^{9c}$;
$C_2$–$C_4$ alkenyl substituted with 0–1 $R^{9c}$;
$C_2$–$C_4$ alkynyl substituted with 0–1 $R^{9c}$;
phenyl substituted with 0–3 $R^{9d}$; and
5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–3 $R^{9d}$;

$R^{9b}$ is selected from the group: H, —C(=O)$R^{9c}$, —C(=O)$OR^{9c}$, —C(=O)$NHR^{9c}$, $C_1$–$C_4$ alkyl, and phenyl;

$R^{9c}$ is selected from the group: $CF_3$, $OCF_3$, Cl, F, Br, OH, C(O)$OR^{11}$, $NH_2$, NH($CH_3$), N($CH_3$)$_2$, —CN, $NO_2$, and phenyl;

$R^{9d}$ is selected at each occurrence from the group: $CF_3$, $OCF_3$, Cl, F, Br, OH, C(O)$OR^{11}$, $NH_2$, NH($CH_3$), N($CH_3$)$_2$, —CN, $NO_2$, $C_1$–$C_4$ alkyl, $C_1$–$C_4$ alkoxy, and phenyl;

$R^{11}$ and $R^{11a}$ are, at each occurrence, independently selected from the group: H, methyl, ethyl, propyl, butyl, phenyl and benzyl;

$R^{13}$ is selected from the group: H, $C_1$–$C_4$ alkyl, phenyl and phenyl-$C_1$–$C_4$ alkyl;

$OR^{26}$ and $OR^{27}$ are independently selected from:
a) —OH,
d) $C_1$–$C_8$ alkoxy, and
when taken together, $OR^{26}$ and $OR^{27}$ form:
e) a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethanedio, 5,6-decanediol, 1,2-dicyclohexylethanediol, diethanolamine, and 1,2-diphenyl-1,2-ethanediol; and $A^4$ is selected from the group: Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O'Bu), Glu(O'Bu), Hyp(O'Bu), Thr(O'Bu), Asp(OBzl), Glu(OBzl), Hyp(OBzl), Pro(OBzl), Thr(OBzl), cyclohexylglycine, cyclohexylalanine, cyclopropylglycine, t-butylglycine, phenylglycine, and 3,3-diphenylalanine.

[5] In another alternative embodiment, the present invention provides a compound of Formula (I) or a pharmaceutically acceptable salt or prodrug thereof, wherein:

$A^1$ is —$CH_2$—;

$A^3$ is H, —$NHCOR^{9a}$, —$CONHR^{9a}$, —NHC(=O)$OR^{9a}$, —$NR^8R^{9a}$; or —NH—$A^4$—$R^{9b}$;

W is pinanediol boronic ester;

$R^1$ is selected from the group: H;
$C_1$–$C_4$ alkyl substituted with 0–2 $R^{1a}$;
$C_2$–$C_4$ alkenyl substituted with 0–2 $R^{1a}$; and
$C_2$–$C_4$ alkynyl substituted with 0–2 $R^{1a}$;

$R^{1a}$ is selected at each occurrence from the group: Cl, F, Br, $CF_3$, and $CHF_2$;

$R^2$ is H;

$R^3$ is selected from the group: $R^4$,
—($CH_2$)$_p$—NN—$R^4$,
—($CH_2$)$_p$—NHC(=O)—$R^4$,
—($CH_2$)$_p$—C(=O)NH—$R^4$,
—($CH_2$)$_p$—C(=O)O—$R^4$,
—($CH_2$)$_p$—NHC(=O)NH—$R^4$,
—($CH_2$)$_p$—NHC(=O)NHC(=O)—$R^4$,
—($CH_2$)$_p$—C(=O)—$R^4$,
—($CH_2$)$_p$—O—$R^4$, and
—($CH_2$)$_p$—S—$R^4$;

p is 0 or 1;

$R^4$ is selected from the group:
$C_1$–$C_4$ alkyl substituted with 0–3 $R^{4a}$;
$C_2$–$C_4$ alkenyl substituted with 0–3 $R^{4a}$;

$C_2$–$C_4$ alkynyl substituted with 0–3 $R^{4a}$;
$C_3$–$C_6$ cycloalkyl substituted with 0–2 $R^{4b}$;
phenyl substituted with 0–3 $R^{4b}$;
naphthyl substituted with 0–3 $R^{4b}$; and
5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4b}$;

$R^{4a}$ is, at each occurrence, independently selected from:
H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, $SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}C(=O)OR^{11a}$, —$NR^{11}C(=O)NR^{11}R^{11a}$, —$NR^{11}SO_2NR^{11}R^{11a}$, —$NR^{11}SO_2R^{11a}$;
$C_1$–$C_4$ alkyl substituted with 0–1 $R^{4b}$;
$C_2$–$C_4$ alkenyl substituted with 0–1 $R^{4b}$;
$C_2$–$C_4$ alkynyl substituted with 0–1 $R^{4b}$;
$C_3$–$C_7$ cycloalkyl substituted with 0–2 $R^{4c}$;
phenyl substituted with 0–3 $R^{4c}$;
naphthyl substituted with 0–3 $R^{4c}$; and
5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4c}$;

$R^{4b}$ is, at each occurrence, independently selected from:
H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}C(=O)OR^{11a}$, —OC(=O)$NR^{11}R^{11a}$, —$NR^{11}C(=O)NR^{11}R^{11a}$, —$NR^{11}SO_2NR^{11}R^{11a}$, —$NR^{11}SO_2R^{11a}$, —OP(O)$(OR^{11})_2$;
$C_1$–$C_4$ alkyl substituted with 0–2 $R^{4c}$;
$C_2$–$C_4$ alkenyl substituted with 0–2 $R^{4c}$;
$C_2$–$C_4$ alkynyl substituted with 0–2 $R^{4c}$;
$C_3$–$C_6$ cycloalkyl substituted with 0–3 $R^{4d}$;
phenyl substituted with 0–3 $R^{4d}$;
naphthyl substituted with 0–3 $R^{4d}$; and
5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4d}$;

$R^{4c}$ is, at each occurrence, independently selected from:
H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, $SO_2NR^{11}R^{11a}$, $C_1$–$C_4$ haloalkyl, $C_1$–$C_4$ haloalkoxy;
$C_1$–$C_4$ alkyl substituted with 0–1 $R^{4d}$;
$C_2$–$C_4$ alkenyl substituted with 0–1 $R^{4d}$;
$C_2$–$C_4$ alkynyl substituted with 0–1 $R^{4d}$;
$C_3$–$C_6$ cycloalkyl substituted with 0–2 $R^{4d}$;
phenyl substituted with 0–3 $R^{4d}$;
naphthyl substituted with 0–3 $R^{4d}$; and
5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4d}$;

$R^{4d}$ is, at each occurrence, independently selected from:
H, F, Cl, Br, I, —$NO_2$, —CN, —NCS, —$CF_3$, —$OCF_3$, =O, OH, —$CO_2H$, —$CO_2R^{11}$, —C(=O)$NR^{11}R^{11a}$, —NHC(=O)$R^{11}$, —$NR^{11}R^{11a}$, —$OR^{11a}$, $SR^{11a}$, —C(=O)$R^{11a}$, —S(=O)$R^{11a}$, —$SO_2R^{11}$, —$SO_2NR^{11}R^{11a}$, $C_1$–$C_4$ alkyl, $C_1$–$C_4$ alkoxy, $C_1$–$C_4$ haloalkyl, $C_1$–$C_4$ haloalkoxy, phenyl, and benzyl;

$R^6$ is H, methyl, ethyl, propyl, or butyl;
$R^8$ is H or methyl;
$R^{9a}$ is selected from the group: H;
$C_1$–$C_4$ alkyl substituted with 0–1 $R^{9c}$;
$C_2$–$C_4$ alkenyl substituted with 0–1 $R^{9c}$;
$C_2$–$C_4$ alkynyl substituted with 0–1 $R^{9c}$;
phenyl substituted with 0–3 $R^{9d}$; and
5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–3 $R^{9d}$;

$R^{9b}$ is selected from the group: H, —C(=O)$R^{9c}$, —C(=O)$OR^{9c}$, —C(=O)$NHR^{9c}$, $C_1$–$C_4$ alkyl, and phenyl;

$R^{9c}$ is selected from the group: $CF_3$, $OCF_3$, Cl, F, Br, OH, C(O)$OR^{11}$, $NH_2$, NH($CH_3$), N($CH_3$)$_2$, —CN, $NO_2$, and phenyl;

$R^{9d}$ is selected at each occurrence from the group: $CF_3$, $OCF_3$, Cl, F, Br, OH, C(O)$OR^{11}$, $NH_2$, NH($CH_3$), N($CH_3$)$_2$, —CN, $NO_2$, $C_1$–$C_4$ alkyl, $C_1$–$C_4$ alkoxy, and phenyl;

$R^{11}$ and $R^{11a}$ are, at each occurrence, independently selected from the group: H, methyl, ethyl, propyl, butyl, phenyl and benzyl;

$R^{13}$ is selected from the group: H, $C_1$–$C_4$ alkyl, phenyl and phenyl-$C_1$–$C_4$ alkyl; and $A^4$ is selected from the group: Val, Ile, Leu, cyclohexylglycine, cyclopropylglycine, t-butylglycine, phenylglycine, and 3,3-diphenylalanine.

[6] In another alternative embodiment, the present invention provides a compound of Formula (I) or a pharmaceutically acceptable salt or prodrug thereof, wherein:

$A^1$ is —$CH_2$—;
$A^3$ is H, —$NHCOR^{9a}$, —$NHC(=O)OR^{9a}$, or —$NR^8R^{9a}$;
W is pinanediol boronic ester;
$R^1$ is H, ethyl, allyl, or 2,2-difluoro-ethyl;
$R^2$ is H;
$R^3$ is selected from the group: $R^4$,
—$(CH_2)_p$—NN—$R^4$,
—$(CH_2)_p$—NHC(=O)—$R^4$,
—$(CH_2)_p$—C(=O)NH—$R^4$,
—$(CH_2)_p$—C(=O)O—$R^4$,
—$(CH_2)_p$—NHC(=O)NH—$R^4$,
—$(CH_2)_p$—NHC(=O)NHC(=O)—$R^4$,
—$(CH_2)_p$—C(=O)—$R^4$,
—$(CH_2)_p$—O—$R^4$, and
—$(CH_2)_p$—S—$R^4$;

p is 0 or 1;

$R^4$ is selected from the group: methyl, isopropyl, t-butyl, phenyl, benzyl, phenethyl, Ph-propyl, phenyl, 2-benzoic acid, 5-isophthalate dimethyl ester, triphenylmethyl, 1-(1-naphthyl)ethyl, 2-methylphenyl, 4-methylphenyl, 4-ethylphenyl, 2-isopropylphenyl, 4-isopropylphenyl, 4-tert-butylphenyl, 2-methoxyphenyl, 3-methoxyphenyl, 4-methoxyphenyl, 2-ethoxyphenyl, 4-ethoxyphenyl, 2-F-phenyl, 3-F-phenyl, 4-F-phenyl, 2-Cl-phenyl, 4-1-phenyl, 2-$CF_3$-phenyl, 3-$CF_3$-phenyl, 4-$F_3$-phenyl, 4-(trifluoromethoxy)phenyl, 2-(hydroxymethyl) phenyl, 4-(hydroxymethyl)phenyl, 3-cyanophenyl, 3-(acetyl)phenyl, 2-phenoxyphenyl, 3-phenoxyphenyl, 4-(acetyl)phenyl, 2-(methoxycarbonyl)-phenyl, 3-(methoxycarbonyl)-phenyl, 4-(methoxycarbonyl)-phenyl, 2-(ethoxycarbonyl)-phenyl, 3-(ethoxycarbonyl)-phenyl, 4-(ethoxycarbonyl)phenyl, 2-(butoxycarbonyl)phenyl, 2-(tert-butoxycarbonyl) phenyl, 4-(dimethylamino)phenyl, 2-((dimethylamino) carbonyl)phenyl, 2-(methylamino)carbonylphenyl, 2-(aminocarbonyl)phenyl, 2-(methylthio)phenyl, 3-(methylthio)phenyl, 4-(methylthio)phenyl, 2-(methylsulfonyl)phenyl, 3-$CF_3$S-phenyl, 2-nitrophenyl, 4-nitrophenyl, 2-aminophenyl, 4-(benzyloxy)phenyl, 2-biphenyl, 4-biphenyl, 2,6-diisopropylphenyl, 2,4-diF-phenyl, 2,5-diF-phenyl, 2,6-diF-phenyl, 3,4-dichlorophenyl, 2,4-dimethoxyphenyl, 2,5-dimethoxyphenyl, 5-Cl-2-methoxyphenyl, 4-F-2-nitrophenyl, 3,4,5,-trimethoxyphenyl, 5-Cl-2,4-dimethoxyphenyl, 5-F-2,4-dimethoxyphenyl, Trans-2-phenylcyclopropyl, 1-naphthyl, 2-naphthyl, 2-pyridinyl, 3-pyridinyl, 2-quinolinyl, 5-quinolinyl, 1-isoquinolinyl, 2-phenyl-4-quinolinyl, 2-methyl-6-quinolinyl, 2-methyl-4-quinolinyl, 2-3-methylbutyric acid methyl ester, 4-benzyl-1-piperidinyl, 4-(2-oxo-2,3-dihydro-1H-benzimidazol-1-yl)-1-piperidinyl, 3-methyl-3-phenyl-piperidinyl, 4-benzyl-4-hydroxy-1-piperidinyl, 4-benzyl-1-piperazinyl, 4-phenyl-1-piperazinyl, 1-Benzyloxycarbonyl-piperazinyl, 4-(4-acetylphenyl)-1-piperazinyl, and 3,4-dihydro-2(1H)-isoquinolinyl;

$R^6$ is H;
$R^8$ is H;
$R^{9a}$ is selected from the group: H;
  $C_1$–$C_4$ alkyl substituted with 0–1 $R^{9c}$;
  phenyl substituted with 0–3 $R^{9d}$; and
  5–6 membered heterocyclic group consisting of carbon atoms and 1–3 heteroatoms selected from the group: O, S, and N; optionally saturated, partially unsaturated or unsaturated; and said 5–6 membered heterocyclic group is substituted with 0–2 $R^{9d}$;

$R^{9c}$ is selected from the group: $CF_3$, $OCF_3$, Cl, F, Br, OH, $C(O)OR^{11}$, $NH_2$, $NH(CH_3)$, $N(CH_3)_2$, —CN, $NO_2$, and phenyl;

$R^{9d}$ is selected from the group: $CF_3$, $OCF_3$, Cl, F, Br, OH, $C(O)OR^{11}$, $NH_2$, $NH(CH_3)$, $N(CH_3)_2$, —CN, $NO_2$, $C_1$–$C_4$ alkyl, $C_1$–$C_4$ alkoxy, and phenyl;

$R^{11}$ is selected from the group: H, methyl, ethyl, propyl, butyl and benzyl; and $R^{13}$ is selected from the group: H, methyl and Ph-propyl.

It is understood that any and all embodiments of the present invention may be taken in conjunction with any other embodiment to descibe additional even more preferred embodiments of the present invention.

[7] In another alternative embodiment, the present invention provides a compound, or a stereoisomer or a pharmaceutically acceptable salt form or prodrug thereof, selected from:

benzyl (6S)-6-[{(1R)-1-[(3aS,4S,6S,7aR)-hexahydro-3a,5,5-trimethyl-4,6-methano-1,3,2-benzodioxaborol-2-yl] amino}carbonyl]-4-oxo-4,6,7,8-tetrahydropyrrolo[1,2-a] pyrimidin-3-ylcarbamate;

benzyl (6S)-6-[({(1R)-1-[(3aS,4S,6S,7aR)-hexahydro-3a,5,5-trimethyl-4,6-methano-1,3,2-benzodioxaborol-2-yl}amino)carbonyl]-4-oxo-4,6,7,8-tetrahydropyrrolo[1,2-a]pyrimidin-3-ylcarbamate;

(6S)-N-{(1R)-1-[(3aS,4S,6S,7aR)-hexahydro-3a,5,5-trimethyl-4,6-methano-1,3,2-benzodioxaborol-2-yl] propyl}-3-amino-4-oxo-4,6,7,8-tetrahydropyrrolo[1,2-a] pyrimidine-6-carboxamide hydrochloride;

(6S)-N-{(1R)-1-[(3aS,4S,6S,7aR)-hexahydro-3a,5,5-trimethyl-4,6-methano-1,3,2-benzodioxaborol-2-yl] propyl}-3-(benzylamino)-4-oxo-4,6,7,8-tetrahydropyrrolo[1,2-a]pyrimidine-6-carboxamide;

(6S)-N-{(1R)-1-[(3aS,4S,6S,7aR)-hexahydro-3a,5,5-trimethyl-4,6-methano-1,3,2-benzodioxaborol-2-yl] propyl}-4-oxo-3-{[3-(trifluoromethyl)benzyl]amino}-4,6,7,8-tetrahydropyrrolo[1,2-a]pyrimidine-6-carboxamide;

(6S)-N-{(1R)-1-[(3aS,4S,6S,7aR)-hexahydro-3a,5,5-trimethyl-4,6-methano-1,3,2-benzodioxaborol-2-yl] propyl}-3-(benzoylamino)-4-oxo-4,6,7,8-tetrahydropyrrolo[1,2-a]pyrimidine-6-carboxamide;

(6S)-N-{(1R)-1-[(3aS,4S,6S,7aR)-hexahydro-3a,5,5-trimethyl-4,6-methano-1,3,2-benzodioxaborol-2-yl] propyl}-3-(acetylamino)-4-oxo-4,6,7,8-tetrahydropyrrolo [1,2-a]pyrimidine-6-carboxamide;

benzyl (6S,8RS)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-4-oxo-8-(3-phenylpropyl)-4,6,7,8-tetrahydropyrrolo[1,2-a]pyrimidin-3-ylcarbamate;

benzyl (6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-4-oxo-8-(3-phenylpropyl)-4,6,7,8-tetrahydropyrrolo[1,2-a]pyrimidin-3-ylcarbamate;

(6S,8R)-N-{(1R)-1-[(3aS,4S,6S,7aR)-hexahydro-3a,5,5-trimethyl-4,6-methano-1,3,2-benzodioxaborol-2-yl]propyl}-4-oxo-8-(3-phenylpropyl)-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-4-oxo-8-(3-phenylpropyl)-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-ylpropyl]}-8-amino-8-methyl-4-oxo-8-[(phenylacetyl)amino]-3-{[3-(trifluoromethyl)benzyl]amino}-4,6,7,8-tetrahydropyrrolo[1,2-a]pyrimidine-6-carboxamide;

phenyl (6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-ylcarbamate;

N-((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)-2-phenyl-4-quinolinecarboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(anilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(benzoylamino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(4-methoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2-fluoroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(3-methoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-8-{[(1-naphthylamino)carbonyl]amino}-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(3-cyanoanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(3-acetylanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-{[(4-phenoxyanilino)carbonyl]amino}3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(4-acetylanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-8-{[(2-naphthylamino)carbonyl]amino}-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-{[((trans-2-phenylcyclopropyl)amino)carbonyl]amino}-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2,4-difluoroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2,5-difluoroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2-methoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-{[(2-(trifluoromethyl)anilino)carbonyl]amino}-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(3-fluoroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(R)-1-[(3aS,4S,6S,7aR)-hexahydro-3a,5,5-trimethyl-4, 6-methano-1,3,2-benzodioxaborol-2-yl]propyl}-8-methyl-4-oxo-8-{[(3-(trifluoromethyl)anilino)carbonyl]amino}-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(4-fluoroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-{[(4-(trifluoromethyl)anilino)carbonyl]amino}-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]

propyl}-8-methyl-8-{[(4-methylanilino)carbonyl]
amino}-4-oxo-3-{[3-(trifluoromethyl)benzyl]amino}-4,
6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(2,6-diisopropylanilino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

methyl 2-({[((6S,8R)-6-[({(1R)-1-[(3aS,4S,6S,7aR)-
hexahydro-3a,5,5-trimethyl-4,6-methano-1,3,2-
benzodioxaborol-2-yl]propyl}amino)carbonyl]-8-
methyl-4-oxo-3-{[3-(trifluoromethyl)benzyl]amino}-4,6,
7,8-tetrahydropyrrolo[1,2-a]pyrimidin-8-yl)amino]
carbonyl}amino)benzoate;

ethyl 2-({[((6S,8R)-6-[({(1R)-1-[(3aS,4S,6S,7aR)-
hexahydro-3a,5,5-trimethyl-4,6-methano-1,3,2-
benzodioxaborol-2-yl]propyl}amino)carbonyl]-8-
methyl-4-oxo-3-{[3-(trifluoromethyl)benzyl]amino}-4,6,
7,8-tetrahydropyrrolo[1,2-a]pyrimidin-8-yl)amino]
carbonyl}amino)benzoate;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(2-isopropylanilino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-3-{[3-(trifluoromethyl)benzyl]
amino}-8-{[(3,4,5-trimethoxyanilino)carbonyl]amino}-
4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-8-{[(3-(methylthio)anilino)carbonyl]
amino}-4-oxo-3-{[3-(trifluoromethyl)benzyl]amino}-4,
6,7,8-tetrahydropyrrolo[1,2-a]pyrimidine-6-
carboxamide;

ethyl 3-({[((6S,8R)-6-[({(1R)-1-[(3aS,4S,6S,7aR)-
hexahydro-3a,5,5-trimethyl-4,6-methano-1,3,2-
benzodioxaborol-2-yl]propyl}amino)carbonyl]-8-
methyl-4-oxo-3-{[3-(trifluoromethyl)benzyl]amino}-4,6,
7,8-tetrahydropyrrolo[1,2-a]pyrimidin-8-yl)amino]
carbonyl}amino)benzoate;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(4-ethoxyanilino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-8-{[(4-(methylthio)anilino)carbonyl]
amino}-4-oxo-3-{[3-(trifluoromethyl)benzyl]amino}-4,
6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(4-isopropylanilino)carbonyl]amino}-8-
methyl-4-oxo-3-{[3-(trifluoromethyl)benzyl]amino)-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(4-ethylanilino)carbonyl]amino}-8-methyl-
4-oxo-3-{[3-(trifluoromethyl)benzyl]amino}-4,6,7,8-
tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-{[(4-(trifluoromethoxy)
anilino)carbonyl]amino}-3-{[3-(trifluoromethyl)benzyl]
amino}-4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-({[(2-phenylethyl)amino]
carbonyl}amino)-3-{[3-(trifluoromethyl)benzyl]amino}-
4,6,7,8-tetrahydropyrrolo[1,2-a]pyrimidine-6-
carboxamide;

methyl 3-(({[((6S,8R)-6-[({(1R)-1-[(3aS,4S,6S,7aR)-
hexahydro-3a,5,5-trimethyl-4,6-methano-1,3,2-
benzodioxaborol-2-yl]propyl}amino)carbonyl]-8-
methyl-4-oxo-3-{[3-(trifluoromethyl)benzyl]amino}-4,6,
7,8-tetrahydropyrrolo[1,2-a]pyrimidin-8-yl)amino]
carbonyl}amino)benzoate;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[([1,1'-biphenyl]-2-ylamino)carbonyl]
amino}-8-methyl-4-oxo-3-{[3-(trifluoromethyl)benzyl]
amino}-4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-3-{[3-(trifluoromethyl)benzyl]
amino}-8-{[(tritylamino)carbonyl]amino}-4,6,7,8-
tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-8-[({[(1R)-1-(1-naphthyl)ethyl]
amino}carbonyl)amino]-4-oxo-3-{[3-(trifluoromethyl)
benzyl]amino}-4,6,7,8-tetrahydropyrrolo[1,2-a]
pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-[({[(1S)-1-(1-phenyl)ethyl]
amino}carbonyl)amino]-3-{[3-(trifluoromethyl)benzyl]
amino}-4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(isopropylamino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-{[(2-phenoxyanilino)
carbonyl]amino}-3-{[3-(trifluoromethyl)benzyl]amino}-
4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(2,6-difluoroanilino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-[({[(1R)-1-(1-phenyl)ethyl]
amino}carbonyl)amino]-3-{[3-(trifluoromethyl)benzyl]
amino}-4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(4-isopropylanilino)carbonyl]amino}-8-
methyl-4-oxo-3-([3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]

propyl}-8-({[4-(dimethylamino)anilino]carbonyl}amino)-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(3,4-dichloroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide (6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(4-tert-butylanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide methyl 2-({[((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)-3-methylbutanoate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(benzylamino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-[({(4-chlorobenzoyl)amino]carbonyl}amino)-8-methyl-4-oxo-3-{[3-(trifluoromethyl)benzyl]amino}-4,6,7,8-tetrahydropyrrolo[1,2-a]pyrimidine-6-carboxamide;

tert-butyl 2-({[((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate;

2-({[((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoic acid;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2-chloroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2,5-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-[(2-toluidinocarbonyl)amino]-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(5-chloro-2,4-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl]-8-{[(2,4-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2-ethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(5-chloro-2-methoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

butyl 2-({[((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-8-({[(2-methylthio)anilino]carbonyl}amino)-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(4-chloroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-8-{[(4-fluoro-2nitroanilino)carbonyl]amino}-4-oxo-3-{[3-(trifluoromethyl)benzyl]amino}-4,6,7,8-tetrahydropyrrolo[1,2-a]pyrimidine-6-carboxamide;

dimethyl 5-({[((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)isophthalate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-3-{[3-(trifluoromethyl)benzyl]amino}-8-[({3-[(trifluoromethyl)sulfanyl]anilino}carbonyl)amino]-4,6,7,8-tetrahydropyrrolo[1,2-a]pyrimidine-6-carboxamide;

ethyl 4-({[((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-8-{[(2-nitroanilino)carbonyl]amino}-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2-aminoanilino)carbonyl]amino}-8-methyl-4-oxo-3-([3-(trifluoromethyl)benzyl]amino}-4,6,7,8-tetrahydropyrrolo[1,2-a]pyrimidine-6-carboxamide;

N-((6S,8R)-6-[({(1RS)-1-[(3aS,4S,6S,7aR)-hexahydro-3a,5,5-trimethyl-4,6-methano-1,3,2-benzodioxaborol-2-yl]-3,3-difluropropyl}amino)carbonyl]-8-methyl-4-oxo-3-{[3-(trifluoromethyl)benzyl]amino}-4,6,7,8-tetrahydropyrrolo[1,2-a]pyrimidin-8-yl)-2-phenyl-4-quinolinecarboxamide;

(6S,8R)-N-{(1RS)-1-[(3aS,4S,6S,7aR)-hexahydro-3a,5,5-trimethyl-4,6-methano-1,3,2-benzodioxaborol-2-yl]-3,3-difluropropyl}-8-{[(2,5-dimethoxyanilino)carbonyl]

amino}-8-methyl-4-oxo-3-{[3-(trifluoromethyl)benzyl]
amino}-4,6,7,8-tetrahydropyrrolo[1,2-a]pyrimidine-6-
carboxamide;

(6S,8R)-N-{(1RS)-1-[(3aS,4S,6S,7aR)-hexahydro-3a,5,5-
trimethyl-4,6-methano-1,3,2-benzodioxaborol-2-yl]-3,3-
difluoropropyl}-8-{[(5-chloro-2,4-dimethoxyanilino)
carbonyl]amino}-8-methyl-4-oxo-3-{[3-
(trifluoromethyl)benzyl]amino}-4,6,7,8-
tetrahydropyrrolo[1,2-a]pyrimidine-6-carboxamide;

methyl 2-({[((6S,8R)-6-[({(1RS)-1-[(3aS,4S,6S,7aR)-
hexahydro-3a,5,5-trimethyl-4,6-methano-1,3,2-
benzodioxaborol-2-yl]-3,3-difluoropropyl}amino)
carbonyl]-8-methyl-4-oxo-3-{[3-(trifluoromethyl)
benzyl]amino}-4,6,7,8-tetrahydropyrrolo[1,2-a]
pyrimidin-8-yl)amino]carbonyl}amino)benzoate;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-8-({[2-(methylthionyl)anilino]
carbonyl}amino)-4-oxo-3-{[3-(trifluoromethyl)benzyl]
amino}-4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(2-ethoxyanilino)carbonyl]amino}-8-
methyl-4-oxo-3-{[3-(trifluoromethyl)benzyllamino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(5-chloro-2-methoxyanilino)carbonyl]}
amino}-8-methyl-4-oxo-3-{[3-(trifluoromethyl)benzyl]
amino}-4,6,7,8-tetrahydropyrrolo[1,2-a]pyrimidine-6-
carboxamide;

ethyl 2-({[(((6S,8R)-6-[({(1RS)-1-[(3aS,4S,6S,7aR)-
hexahydro-3a,5,5-trimethyl-4, 6-methano-1,3,2-
benzodioxaborol-2-yl]-3,3-difluoropropyl}amino)
carbonyl]-8-methyl-4-oxo-3-{[3-(trifluoromethyl)
benzyl]amino}-4,6,7,8-tetrahydropyrrolo[1,2-a]
pyrimidin-8-yl)amino]carbonyl}amino)benzoate;

tert-butyl ((6S,8R)-6-[({(1R)-1-[(3aS,4S,6S,7aR)-
hexahydro-3a,5,5-trimethyl-4,6-methano-1,3,2-
benzodioxaborol-2-yl]propyl}amino)carbonyl]-8-
methyl-4-oxo-3-{[3-(trifluoromethyl)benzyl]amino}-4,6,
7,8-tetrahydropyrrolo[1,2-a]pyrimidin-8-yl)acetate;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-(2-anilino-2-oxoethyl)-8-methyl-4-oxo-3-{[3-
(trifluoromethyl)benzyl]amino}-4,6,7,8-
tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-(4-nitroanilino)-2-oxoethyl]-8-methyl-4-
oxo-3-{[3-(trifluoromethyl)benzyl]amino}-4,6,7,8-
tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-[2-oxo-2-(2-pyridinylamino)
ethyl]-3-{[3-(trifluoromethyl)benzyl]amino}-4,6,7,8-
tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-(1-naphthylamino)-2-oxoethyl]-8-methyl-
4-oxo-3-{[3-(trifluoromethyl)benzyl]amino}-4,6,7,8-
tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-(3-methoxyanilino)-2-oxoethyl]-8-methyl-
4-oxo-3-{[3-(trifluoromethyl)benzyl]amino}-4,6,7,8-
tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-oxo-2-(5-quinolinylamino)ethyl]-8-methyl-
4-oxo-3-{[3-(trifluoromethyl)benzyl]amino}-4,6,7,
8-tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-{2-[(2-methyl-6-quinolinyl)amino]-2-
oxoethyl}-8-methyl-4-oxo-3-{[3-(trifluoromethyl)
benzyl]amino}-4,6,7,8-tetrahydropyrrolo[1,2-a]
pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-oxo-2-(3-pyridinylamino)ethyl]-8-methyl-
4-oxo-3-{[3-(trifluoromethyl)benzyl]amino}-4,6,7,8-
tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-(1-isoquinolinylamino)-2-oxoethyl]-8-
methyl-4-oxo-3-{[3-(trifluoromethyl)benzyl]amino}-4,6,
7,8-tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-2-oxoethyl}-8-methyl-4-oxo-8-[2-oxo-2-(2-
quinolinylamino)ethyl]-3-{[3-(trifluoromethyl)benzyl]
amino}-4,6,7,8-tetrahydropyrrolo[1,2-a]pyrimidine-6-
carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-(2-methoxyanilino)-2-oxoethyl]-8-methyl-
4-oxo-3-{[3-(trifluoromethyl)benzyl]amino}-4,6,7,8-
tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-([1,1'-biphenyl]-4-ylamino)-2-oxoethyl]-8-
methyl-4-oxo-3-{[3-(trifluoromethyl)benzyl]amino}-4,6,
7,8-tetrahydropyrrolo[1,2-a]pyrimidine-6-carboxamide;

methyl 4-{[(((6S,8S)-6-[({(1R)-1-[(3aS,4S,6S,7aR)-
Hexahydro-3a,5,5-trimethyl-4,6-methano-1,3,2-
benzodioxaborol-2-yl]propyl}amino)carbonyl]-8-
methyl-4-oxo-3-{[3-(trifluoromethyl)benzyl]amino}-4,6,
7,8-tetrahydropyrrolo[1,2-a]pyrimidin-8-yl)acetyl]
amino}benzoate;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-([benzylamino)-2-oxoethyl]-8-methyl-4-
oxo-3-{[3-(trifluoromethyl)benzyl]amino}-4,6,7,8-
tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-{2-[4-(hydroxymethyl)anilino]-2-oxoethyl}-8-
methyl-4-oxo-3-{[3-(trifluoromethyl)benzyl]amino}-4,6,
7,8-tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-[2-(4-tert-butylanilino)-2-oxoethyl]-8-methyl-
4-oxo-3-{[3-(trifluoromethyl)benzyl]amino}-4,6,7,8-
tetrahydropyrrolo[1,2-a]pyrimidine-6-carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-2-oxoethyl}-8-methyl-4-oxo-8-{2-[3-
(trifluoromethyl)anilino-3-{[3-(trifluoromethyl)benzyl]
amino}-4,6,7,8-tetrahydropyrrolo[1,2-a]pyrimidine-6-
carboxamide;

(6S,8S)-N-{(1R)-1-[(3aS,4S,6S,7aR)-hexahydro-3a,5,5-
trimethyl-4,6-methano-1,3,2-benzodioxaborol-2-yl]
propyl}-8-{2-[4-(benzyloxy)anilino]-2-oxoethyl}-8- methyl-4-oxo-3-{[3-(trifluoromethyl)benzyl]amino}-4,6,7,8-tetrahydropyrrolo[1,2-a]pyrimidine-6-carboxamide;

tert-butyl ((6S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-4-oxo-3-{[3-(trifluoromethyl)benzyl]amino}-4,6,7,8-tetrahydropyrrolo[1,2-a]pyrimidin-8-yl)acetate;

(6S)-N-{(1R)-1-[(3aS,4S,6S,7aR)-hexahydro-3a,5,5-trimethyl-4,6-methano-1,3,2-benzodioxaborol-2-yl]propyl}-8-(2-anilino-2-oxoethyl)-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-(3-phenylpropyl)-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-(2-anilino-2-oxoethyl)-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(benzylamino)-2-oxoethyl]-8-methyl-4-oxo-3-{[3-(trifluoromethyl)benzyl]amino}-4,6,7,8-tetrahydropyrrolol,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(1-isoquinolinylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(2-methoxyanilino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

methyl 2-{[(((6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetyl]amino}benzoate;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-[2-oxo-2-(3-pyridinylamino)ethyl]-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-{2-[2-(hydroxymethyl)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(4-benzyl-1-piperidinyl)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-{2-oxo-2-[4-(2-oxo-2,3-dihydro-1H-benzimidazol-1-yl)-1-piperidinyl]ethyl}-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-8-[2-(3-methyl-3-phenyl-1-piperidinyl)-2-oxoethyl]-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(4-benzyl-4-hydroxy-1-piperidinyl)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(4-benzyl-1-piperazinyl)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-[2-oxo-2-(4-phenyl-1-piperazinyl)ethyl]-3-{[3-(trifluoromethyl)benzyl]amino}-4,6,7,8-tetrahydropyrrolo[1,2-a]pyrimidine-6-carboxamide benzyl 4-[(((6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl) acetyl]-1-piperazinecarboxylate;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(3,4-dihydro-2(1H)-isoquinolinyl)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-{2-[4-(4-acetylphenyl)-1-piperazinyl]-2-oxoethyl}-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-8-{2-[3-(methylsulfanyl)anilino]-2-oxoethyl}-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-8-{2-[(2-methyl-4-quinolinyl)amino]-2-oxoethyl}-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-8-[2-(1-naphthylamino)-2-oxoethyl]-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-8-[2-(2-nitroanilino)-2-oxoethyl]-4-oxo-3-{[3-(trifluoromethyl)benzyl]amino})-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-{2-oxo-2-[(2-phenyl-4-quinolinyl)amino]ethyl}-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]

propyl}-8-(2-{2-[(dimethylamino)carbonyl]anilino}-2-oxoethyl)-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-(2-{2-[(methylamino)carbonyl]anilino}-2-oxoethyl)-8-methyl-4-oxo-3-{[3-(trifluoromethyl)benzyl]amino}-4,6,7,8-tetrahydropyrrolo[1,2-a]pyrimidine-6-carboxamide; and (6S,8S)-N-{(1R)-1-[(3aS,4S,6S,7aR)-hexahydro-3a,5,5-trimethyl-4,6-methano-1,3,2-benzodioxaborol-2-yl]propyl}-8-{2-[2-(aminocarbonyl)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide.

This invention also provides compositions comprising one or more of the foregoing compounds and methods of using such compositions in the treatment of hepatitis C virus, such as inhibition of hepatitis C virus protease, in mammals or as reagents used as inhibitors of hepatitis C virus protease in the processing of blood to plasma for diagnostic and other commercial purposes.

In another embodiment, the present invention provides a pharmaceutical composition comprising a compound of Formula (I) and a pharmaceutically acceptable carrier.

In another embodiment, the present invention provides a method of treating a viral infection which comprises administering to a host in need of such treatment a therapeutically effective amount of compounds of Formula (I) or pharmaceutically acceptable salt forms or prodrug thereof.

In another embodiment, the present invention provides A method of treating HCV which comprises administering to a host in need of such treatment a therapeutically effective amount of compounds of Formula (I) or pharmaceutically acceptable salt forms or prodrug thereof.

Definitions

As used throughout the specification, the following abbreviations for amino acid residues or amino acids apply:
Abu is L-aminobutyric acid;
Ala is L-alanine;
Alg is L-2-amino-4-pentenoic acid;
Ape is L-2-aminopentanoic acid;
Arg is L-arginine;
Asn is L-asparagine;
Asp is L-aspartic acid;
Aze is azedine-2-carboxlic acid;
Cha is L-2-amino-3-cyclohexylpropionic acid;
Cpa is L-2-amino-3-cyclopropylpropionic acid
Cpg is L-2-amino-2-cyclopropylacetic acid;
Cys is L-cysteine;
Dfb is L-4,4'-difluoro-1-amino-butyric acid;
Dpa is L-2-amino-3,3-diphenylpropionic acid;
Gla is gamma-carboxyglutamic acid;
Gln is L-glutamine;
Glu is L-glutamic acid;
Gly is glycine;
His is L-histidine;
HomoLys is L-homolysine;
Hyp is L-4-hydroxyproline;
Ile is L-isoleucine;
Irg is isothiouronium analog of L-Arg;
Leu is L-leucine;
Lys is L-lysine;
Met is L-methionine;
Orn is L-ornithine;
Phe is L-phenylalanine;
Phe(4-fluoro) is para-fluorophenylalanine;
Pro is L-proline;
Sar is L-sarcosine;
Ser is L-serine;
Thr is L-threonine;
Tpa is L-2-amino-5,5,5-trifluoropentanoic acid;
Trp is L-tryptophan;
Tyr is L-tyrosine; and
Val is L-valine.

The "D" prefix for the foregoing abbreviations indicates the amino acid is in the D-configuration. "D,L" indicates the amino is present in mixture of the D- and the L-configuration. The prefix "boro" indicates amino acid residues where the carboxyl is replaced by a boronic acid or a boronic ester. For example, if $R^1$ is isopropyl and $Y^1$ and $Y^2$ are OH, the C-terminal residue is abbreviated "boroVal-OH" where "—OH" indicates the boronic acid is in the form of the free acid. The pinanediol boronic ester and the pinacol boronic ester are abbreviated "—$C_{10}H_{16}$" and "—$C_6H_{12}$", respectively. Examples of other useful diols for esterification with the boronic acids are 1,2-ethanediol, 1,3-propanediol, 1,2-propanediol, 2,3-butanediol, 1,2-diisopropylethanediol, 5,6-decanediol, and 1,2-dicyclohexylethanediol. Analogs containing sidechain substituents are described by indicating the substituent in parenthesis following the name of the parent residue. For example the analog of borophenylalanine containing a meta cyano group is -boroPhe(mCN)—.

The following abbreviations may also be used herein and are defined as follows. The abbreviation "DIBAL" means diisobutylaluminum hydride. The abbreviation "RaNi" means Raney nickel. The abbreviation "LAH" means lithium aluminum hydride. The abbreviation "1,1'-CDI" means 1,1'-carbonyldiimidazole. The abbreviation "Bn" means benzyl. The abbreviation "BOC" means t-butyl carbamate. The abbreviation "CBZ" means benzyl carbamate. Other abbreviations are: "BSA", benzene sulfonic acid; "THF", tetrahydrofuran; "DMF", dimethylformamide; "EDCI", 1-dimethylaminopropyl-3-ethylcarbodiimide hydrochloride; "HOAt", 1-hydroxy-7-azabenzotriazole; "DIEA", N,N-diisopropylethylamine; "Boc-", t-butoxycarbonyl-; "Ac-", acetyl; "pNA", p-nitro-aniline; "DMAP", 4-N,N-dimethylaminopyridine; "Tris", Tris(hydroxymethyl)aminomethane; "PyAOP", 7-azabenzotriazol-1-yloxytris(pyrrolidino)phosphonium hexafluorophosphate; "MS", mass spectrometry; "FAB/MS", fast atom bombardment mass spectrometry. LRMS ($NH_3$—CI) and HRMS($NH_3$—CI) are low and high resolution mass spectrometry, respectively, using $NH_3$ as an ion source.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

The reactions of the synthetic methods claimed herein are carried out in suitable solvents which may be readily selected by one skilled in the art of organic synthesis, said suitable solvents generally being any solvent which is substantially nonreactive with the starting materials (reactants), the intermediates, or products at the temperatures at which the reactions are carried out. A given reaction may be carried out in one solvent or a mixture of more than one solvent. Depending on the particular reaction step, suitable solvents for a particular reaction step may be selected.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then two hydrogens on the atom are replaced.

When any variable (e.g., $R^{4a}$ or $R^{11}$) occurs more than one time in any constituent or formula for a compound, its definition at each occurrence is independent of its definition at every other occurrence. Thus, for example, if a group is shown to be substituted with 0–3 $R^{4a}$, then said group may optionally be substituted with up to three $R^{4a}$ groups and $R^{4a}$ at each occurrence is selected independently from the definition of $R^{4a}$. Also, combinations of substituents and/or variables are permissible only if such combinations result in stable compounds. By stable compound it is meant herein a compound that is sufficiently robust to survive isolation to a useful degree of purity from a reaction mixture.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

"Amino acid residue" as used herein, refers to natural, modified or unnatural amino acids of either D- or L-configuration and means an organic compound containing both a basic amino group and an acidic carboxyl group. Natural amino acids residues are Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, and Val. Roberts and Vellaccio, The Peptides, Vol 5; 341–449 (1983), Academic Press, New York, discloses numerous suitable unnatural amino acids and is incorporated herein by reference for that purpose. Additionally, said reference describes, but does not extensively list, acylic N-alkyl and acyclic α,α-disubstituted amino acids. Included in the scope of the present invention are N-alkyl, aryl, and alkylaryl analogs of both in chain and N-terminal amino acid residues. Similarly, alkyl, aryl, and alkylaryl maybe substituted for the alpha hydrogen. Illustrated below are examples of N-alkyl and alpha alkyl amino acid residues, respectively.

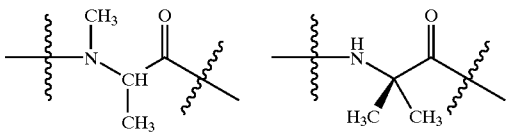

Modified amino acids which can be used to practice the invention include, but are not limited to, D-amino acids, hydroxylysine, 4-hydroxyproline, 3-hydroxyproline, an N-CBZ-protected amino acid, 2,4-diaminobutyric acid, homoarginine, norleucine, N-methylaminobutyric acid, 3,3-diphenylalanine, naphthylalanine, phenylglycine, β-phenylproline, tert-leucine, cyclohexylalanine, 4-aminocyclohexylalanine, N-methyl-norleucine, 3,4-dehydroproline, t-butylglycine, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, 2-benzyl-5-aminopentanoic acid.

A list of unnatural amino acids that fall within the scope of this invention is disclosed in a PCT application PCT/US00/18655. The disclosure of which is hereby incorporated by reference.

"Amino acid residue" also refers to various amino acids where sidechain functional groups are modified with appropriate protecting groups known to those skilled in the art. "The Peptides", Vol 3, 3–88 (1981) discloses numerous suitable protecting groups and is incorporated herein by reference for that purpose. Examples of amino acids where sidechain functional groups are modified with appropriate protecting groups include, but are not limited to, Asp(OMe), Glu(OMe), Hyp(OMe), Asp(O'Bu), Glu(O'Bu), Hyp(O'Bu), Thr(O'Bu), Asp(OBzl), Glu(OBzl), Hyp(OBzl), and Thr(OBzl); wherein OMe is methoxy, O'Bu is tert-butoxy, and OBzl is benzyloxy.

A preferred list of "amino acid residue" in the present invention includes, but is not limited to, Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O'Bu), Glu(O'Bu), Hyp(O'Bu), Thr(O'Bu), Asp(OBzl), Glu(OBzl), Hyp(OBzl), Thr(OBzl), cyclohexylglycine, cyclohexylalanine, cyclopropylglycine, t-butylglycine, phenylglycine, and 3,3-diphenylalanine.

A preferred scope of substituent $A^4$ is Val, Ile, Leu, cyclohexylglycine, cyclopropylglycine, t-butylglycine, phenylglycine, and 3,3-diphenylalanine.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

As used herein, "carbocycle", "carbocyclic ring", "carbocyclic group", or "carbocyclic ring system" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle", "heterocyclic group", "heterocyclic ring" "heterocyclic ring system" or "Het" is intended to mean a stable 5- to 7-membered monocyclic or bicyclic or 7- to 14-membered bicyclic heterocyclic ring which is saturated, partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, benzo[1,3]dioxol-yl, 2,3-dihydro-benzo[1,4]dioxin-yl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyrimidopyrimidin-yl, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred 5–10 membered heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and Spiro compounds containing, for example, the above heterocycles.

The term "Het-(lower alkyl)-" as used herein, means a heterocyclic ring as defined above linked through a chain or branched $C_1$–$C_6$ alkyl group.

As used herein, the term "aryl", or aromatic residue, is intended to mean an aromatic moiety containing the specified number of carbon atoms, such as phenyl and naphthyl.

"$NH_2$-blocking group" as used herein, refers to various acyl, thioacyl, alkyl, sulfonyl, phosphoryl, and phosphinyl groups comprised of 1 to 20 carbon atoms. Substitutes on these groups maybe either alkyl, aryl, alkylaryl which may contain the heteroatoms, O, S, and N as a substituent or in-chain component. A number of $NH_2$-blocking groups are recognized by those skilled in the art of organic synthesis. By definition, an $NH_2$-blocking group may be removable or may remain permanently bound to the $NH_2$. Examples of suitable groups include formyl, acetyl, benzoyl, trifluoroacetyl, and methoxysuccinyl; aromatic urethane protecting groups, such as, benzyloxycarbonyl; and aliphatic urethane protecting groups, such as t-butoxycarbonyl or adamantyloxycarbonyl. Gross and Meinhoffer, eds., The Peptides, Vol 3; 3–88 (1981), Academic Press, New York, and Greene and Wuts Protective Groups in Organic Synthesis, 315–405 (1991), J. Wiley and Sons, Inc., New York disclose numerous suitable amine protecting groups and they are incorporated herein by reference for that purpose. Amine protecting groups may include, but are not limited to the following: 2,7-di-t-butyl-[9-(10,10-dioxo-10,10,10,10-tetrahydrothio-xanthyl)]methylo xycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl) ethyloxycarbonyl; benzyloxycarbonyl; p-nitrobenzyloxycarbonyl; 2-(p-toluenesulfonyl) ethyloxycarbonyl; m-chloro-p-acyloxybenzyloxycarbonyl; 5-benzyisoxazolylmethyloxycarbonyl; p-(dihydroxyboryl) benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, "cyclic boronic ester" is intended to mean a stable cyclic boronic moiety of general formula —B(OR)(OR) wherein the two R substituents taken together contain from 2 to 20 carbon atoms, and optionally, 1, 2, or 3 heteroatoms which can be N, S, or O Cyclic boronic esters are well known in the art. Examples of cyclic boronic ester include, but are not limited to, pinanediol boronic ester, pinacol boronic ester, 1,2-ethanediol boronic ester, 1,3-propanediol boronic ester, 1,2-propanediol boronic ester, 2,3-butanediol boronic ester, 1,2-diisopropylethanediol boronic ester, 5,6-decanediol boronic ester, 1,2-dicyclohexylethanediol boronic ester, diethanolamine boronic ester, and 1,2-diphenyl-1,2-ethanediol boronic ester.

As used herein, "cyclic boronic amide" is intended to mean a stable cyclic boronic amide moiety of general formula —B(NR)(NR) wherein the two R substituents taken together contain from 2 to 20 carbon atoms, and optionally, 1, 2, or 3 heteroatoms which can be N, S, or O Examples of cyclic boronic amide include, but are not limited to, 1,3-diaminopropane boronic amide and ethylenediamine boronic amide.

As used herein, "cyclic boronic amide-ester" is intended to mean a stable cyclic boronic amide-ester moiety of general formula —B(OR)(NR) wherein the two R substituents taken together contain from 2 to 20 carbon atoms, and optionally, 1, 2, or 3 heteroatoms which can be N, S, or O. Examples of cyclic boronic amide include, but are not limited to, 3-amino-1-propanol boronic amide-ester and ethanolamine boronic amide-ester.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p.1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

The term "treating" refers to: (i) preventing a disease, disorder or condition from occurring in an animal which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

The compounds of this invention are intended to interact with the catalytic serine hydroxyl of Hepatitis C NS3 protease, and therefore incorporate an electrophilic moiety capable of such interaction. In the synthetic schemes below, this moiety, or its synthetic equivalent or precursor, is referred to as a "serine trap" and is defined by structure 1.11.

Synthesis of Inhibitors 1.13, 2.3, 2.6, 2.9, 2.12, 2.14

Schemes 1 and 2A–2D illustrate the synthesis of inhibitors of structure 1.13, 2.3, 2.6, 2.9, 2.12, and 2.14. In Schemes 1 and 2A–2D, W is as defined above, P is a nitrogen protecting group, and R is a standard leaving group for carboxylic acids, wherein such protecting and leaving groups are known to one skilled in the art.

The synthesis of inhibitor 1.13 is depicted in Scheme 1. An intermediate in this synthesis, Bicyclic pyrimidinone 1.9 (n=1), is prepared as previously described by Webber et al. (Webber, S. E.; Dragovich, P. S.; Littlefield, E. S.; Marakovits, J. T.; Babine, R. E. WO 99/31122) and is described in the scheme. Lactam 1.1 (n=0–3) is protected as ester 1.2, which is subsequently converted to thiolactam 1.3 by treatment with Lawesson's reagent. Thiolactam 1.3 is alkylated with MeI to afford 1.4, which is displaced with ammonium chloride providing amidine 1.5. Compound 1.5 is condensed with dimethyl methoxymethylenemalonate to afford bicyclic pyrimidinone 1.6. The methyl ester functionality of ester 1.6 is cleaved with aqueous base to afford acid 1.7, which is then subjected to a Curtius rearrangment using diphenylphosphoryl azide and a suitable alcohol to afford carbamate 1.8. At this point, an $R^1$ substituent may be introduced via NaH induced alkylation of the carbamate nitrogen and the R substituent of the ester may be modified or converted to the corresponding amide via standard (EDCI/HOAt) amide coupling of the corresponding acid. This compound then can be deprotonated with strong base, and the resultant anion reacted with electrophiles. In this way, one or two electrophiles (reaction with $R^3$-X" and $R^{13}$-X") may be introduced to give substituted bicyclic pyrimidinone 1.7. In addition, electrophiles such as aldehydes and epoxides may be employed and the resultant carbanols may optionally be eliminated to afford the alkene. At this point, substituents $R^3$ and $R^{13}$ of compound 1.8 may optionally be modified, followed by deprotection to reveal carboxylic acid 1.9. Peptide coulping of acid 1.10 with serine-trap 1.11 affords amide 1.12. At this point, the R-derived carbamate functionality is cleaved. Optionally, $R^1$, $R^3$, and $R^{13}$ functionality may be modified and $R^2$ may be introduced to afford inhibitor 1.13.

Inhibitor 2.3 is prepared by deprotonation of lactam 2.1 (n=0–3) and reaction with electrophile(s) to provide compound 2–2, either monosubstituted or disubstituted, followed by a reaction sequence similar to the preparation of inhibitor 1.13. Similarly, inhibitor 2.6 is prepared beginning with cyclic amine 2.4 (N=0–3), which is made according to the chemistry described by Sardina et al. (Blanco et al., *J. Org. Chem.* 1999, 64, 8786–8793). Cyclic amine 2.4 (n=0–3) is oxidized with ruthenium oxide in a two-phase system (Yoshifuji et al., *Chem. Pharma. Bull.* 1986, 34, 3873–3878.) to the corresponding lactam 2.5. Lactam 2.5 (n=1) may also be prepared according to chemistry developed by Hruby, V. J. et al. (Soloshonok et al. *J. Org. Lett.* 2000, 2, 747–750). Following chemistry described above, lactam 2.5 is converted into inhibitor 2.6.

Inhibitor 2.9 is prepared analogously to inhibitor 1.13 from piperazinone 2.8. Compound 2–8 is prepared via reductive amination of piperazinone 2–7, which is prepared according to the chemistry developed by Aebischer et al. (*Helv. Chim. Acta* 1989, 72, 1043–51). Inhibitor 2.12 is prepared from bicyclic pyrimidinone 2.11 via chemistry analogous to the preparation of inhibitor 1.13. Intermediate 2.11 in turn is prepared via a condensation amidine 1.5 and methylene malonate 2.10 followed by N-bromosuccinimide-promoted unsaturation. Compound 2.11 is prepared following chemistry described by Veale et al. (*J. Org. Chem.* 1993, 58, 4490–4493.). Inhibitor 2.14 is prepared from morpholinone 2.13 via chemistry analogous to the preparation of inhibitor 1.13. Intermediate 2.13 is prepared via a condensation of CbzSerOtBu and methyl bromoacetate.

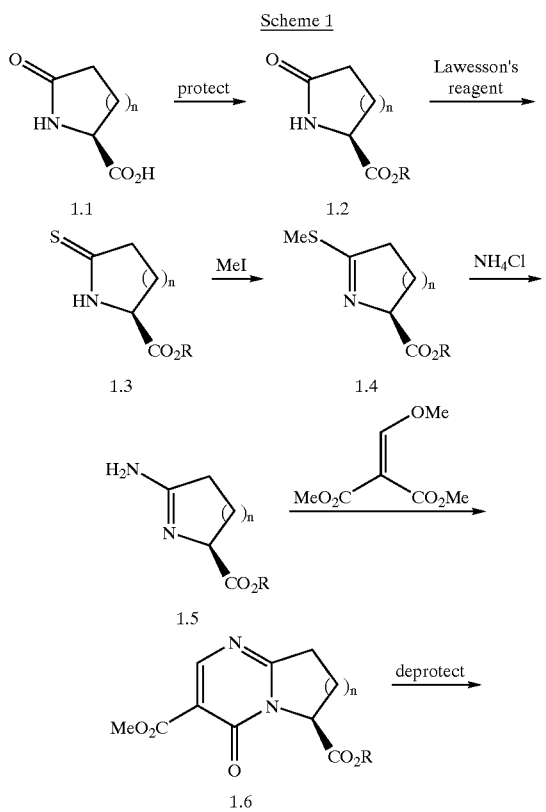

Scheme 1

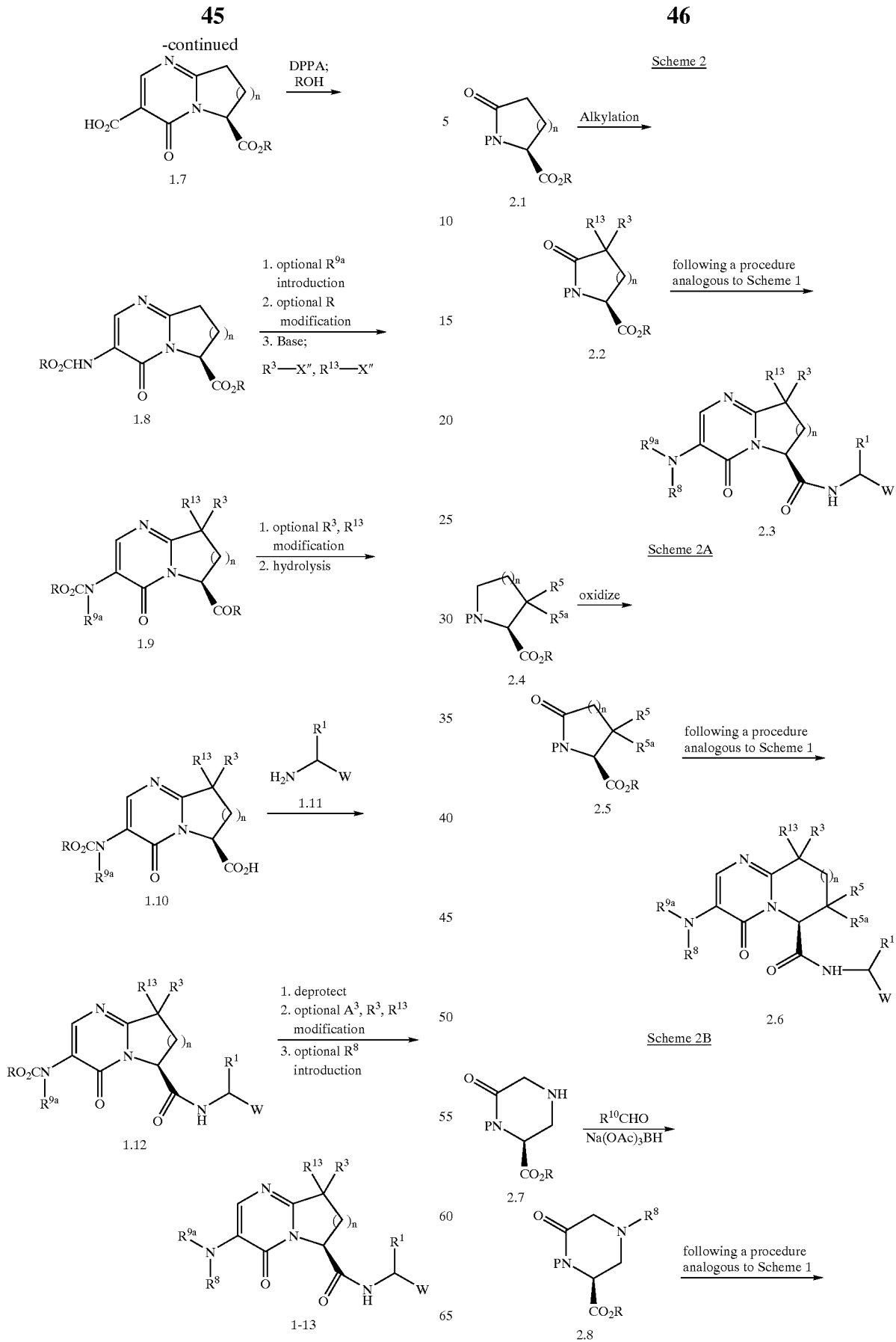

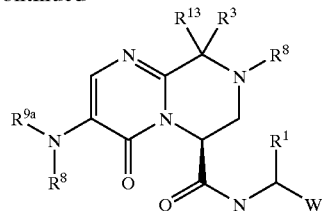

2.9

Scheme 2C

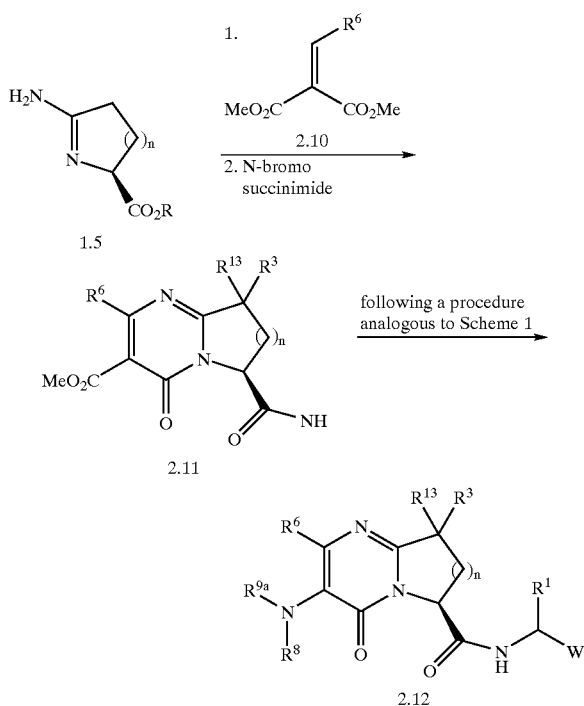

Scheme 2D

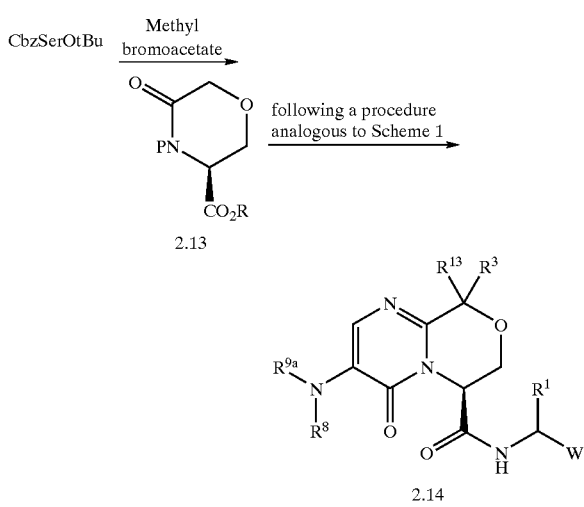

Compounds of the present invention containing peptide segments in A³ can be prepared from commercially available materials by methods known to one skilled in the art of peptide synthesis. More preferably, see techniques disclosed in copending commonly assigned U.S. Provisional Patent Application U.S. Ser. No. 60/242,557, filed Oct. 23, 2000; herein incorporated in its entirety by reference.

Synthesis of a Serine Trap of Structure 1.11 a) Synthesis of α-amino boronic ester

Scheme 3 outlines a route to mono-substituted amino boronic esters. In Scheme 3, a Grignard reagent is reacted with a borate ester 3.12a, which can be prepared by the reaction of pinanediol with trialkylborate, providing boronate 3.12b. Homologation of 3.12b with the anion of dichloromethane gives the α-chloro boronic ester 3.12c. (Matteson, D. S. & Majumdar, D., *Organometallics* 1983, 2, 1529–1535). Displacement of the chloride by lithium bis(trimethylsilyl)amide gives silyl amine 3.12d, which is converted to the amine hydrochloride salt 3.12e with anhydrous HCl. (Matteson, D. S. & Sadhu, K. M., *Organometallics* 1984, 3, 1284–1288). Notice that 3.12e is shown protected as the pinanediol ester. This is the preferred protecting group, but other diol protecting groups, for example but not to be limiting the scope of workable and known diol protecting groups, pinacol, 1,2-ethanediol, 1,2-propanediol, 1,3-propanediol, 2,3-butanediol, 1,2-diisopropylethanediol, 5,6-decanediol, 1,2-dicyclohexylethanediol, are known to those skilled in the art.

Peptide boronic esters can be prepared from commercially available materials by methods known to one skilled in the art of organic synthesis. Peptide boronic acids and esters are generally well known in the art; however, for a general reference to synthesis of peptide boronic esters, see: Kettner, C; Forsyth, T. Houben-Weyl *Methods of Organic Chemistry* 1999, in press; for a reference to synthesis of fluorinated peptide residues see Matassa et al., PCT Application WO 9964442. More preferably, see techniques disclosed in copending commonly assigned U.S. Provisional Patent Application U.S. Ser. No. 60/142,561, filed Jul. 7, 1999; herein incorporated in its entirety by reference; as well as copending commonly assigned U.S. Provisional Patent Application U.S. Ser. No. 60/145,631, filed Jul. 26, 1999; herein incorporated in its entirety by reference.

Scheme 3

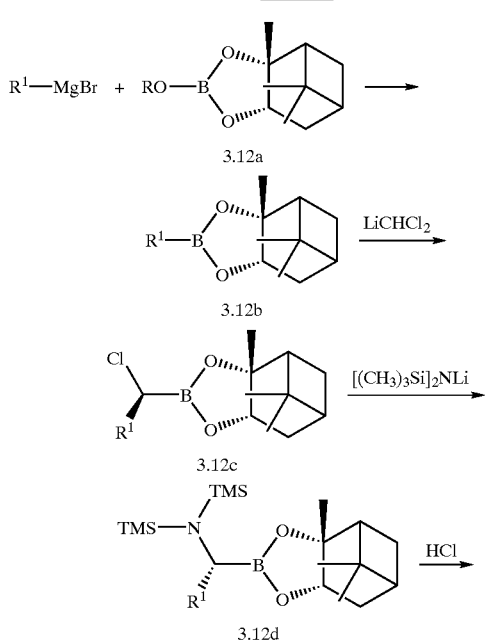

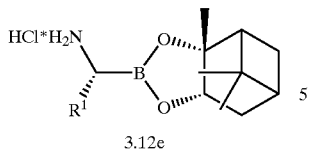

3.12e

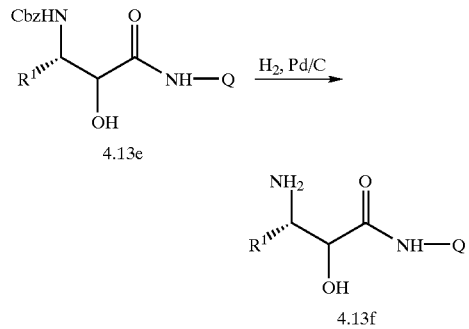

b) Synthesis of α-ketoamide, α-ketoester and α-diketone

α-Ketoamides and other α-keto derivatives are generally introduced in the hydroxy form and oxidized to the active ketone form in the final synthetic step after it is coupled to the pyrazinone carboxylic acid 1.9. Scheme 4 illustrates the synthesis of α-hydroxy esters and α-hydroxy amides. In Scheme 4, substituted acrylate ester 4.13a is aminohydroxylated using a Sharpless's procedure (Tao, B., Sharpless, K. B. et al. *Tetrahedron Lett.* 1998, 39, 2507–2510) to Cbz-protected amino alchol 4.13b. Catalytic hydrogenation of 4.13b gives α-hydroxy ketoester 4.13c. Alternatively, 4.13b is hydrolyzed to free acid 4.13d and coupled to amine $H_2N$—Q to give Cbz-protected amino α-hydroxy amide 4.13e. Catalytic hydrogenation of 4.13e gives α-hydroxy ketoamide 4.13f. For other methods to prepare α-keto esters, amides or other electrophilic carbonyl derivatives, see: Peet et al., *Tetrahedron Lett.* 1988, 3433–3436; Edwards, P. D. & Bernstein, P. R., *Medicinal Res. Reviews* 1994, 14, 127–194, and references cited therein; Sharpless et al., *Angew. Chem. Int. Ed. Engl.* 1996, 35, 451; and Sharpless et al., *Angew. Chem. Int. Ed. Engl.* 1996, 35, 2813. Many of the α,β-unsaturated esters, 4.13a, are commercially available or may be easily prepared from commercially available materials.

Amines of formula $H_2N$—Q can be prepared from commercially available materials by methods known to one skilled in the art of organic synthesis. More preferably, see techniques disclosed in copending commonly assigned U.S. Provisional Patent Application U.S. Ser. No. 60/168,998, filed Dec. 3, 1999; herein incorporated in its entirety by reference.

c) Synthesis of Amino Trifluoromethyl and Pentafluoroethyl Ketones

Similar to α-ketoamides and other α-keto derivatives, the trifluoromethyl or pentafluoroethyl ketone functionality is also introduced in the hydroxy form and oxidized to the active ketone form in the final step. Scheme 5 illustrates the synthesis of amino trifluoromethyl alcohol (Skiles et al., *J. Med. Chem.* 1992, 35, 641–662) and amino pentafluoroethyl alcohol (Ogilvie et al., *J. Med. Chem.* 1997, 40, 4113–4135). In Scheme 5, a Henry reaction between a nitroalkane $R^1NO_2$ and trifluoroacetaldehyde ethyl hemiacetal affords nitro alcohol 5.14a, which is hydrogenated over Ra—Ni and the resulting amino alcohol 5.14b is converted to the N-Boc derivative 5.14c. Treatment of the Boc-amine with anhydrous HCl affords the hydrochloride salt 5.14d. A solid-phase synthesis of peptidyl trifluoromethyl ketones is also known, see: Poupart et al., *J. Org. Chem.* 1999, 64, 1356–1361. Alternatively, condensation of the Weinreb amide 5.15a with $CF_3CF_2Li$ followed by reduction with $NaBH_4$ gives pentafluoroethyl substituted alcohol 5.15b. Deprotection of 5.15b gives the amino alcohol salt 5.15d.

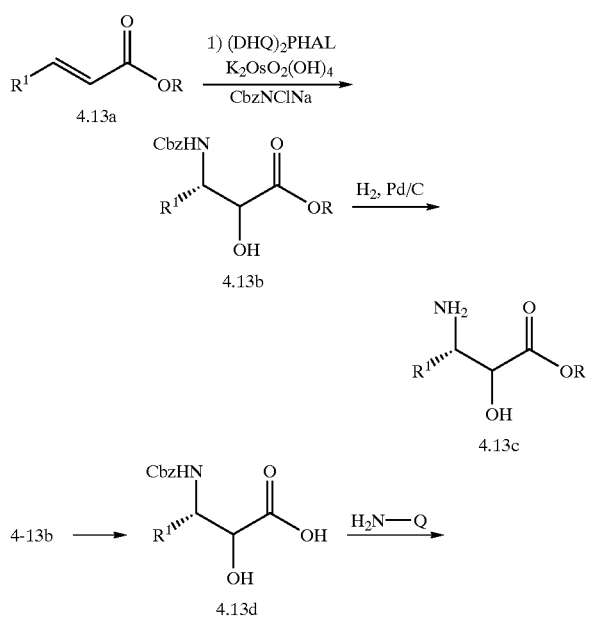

Scheme 4

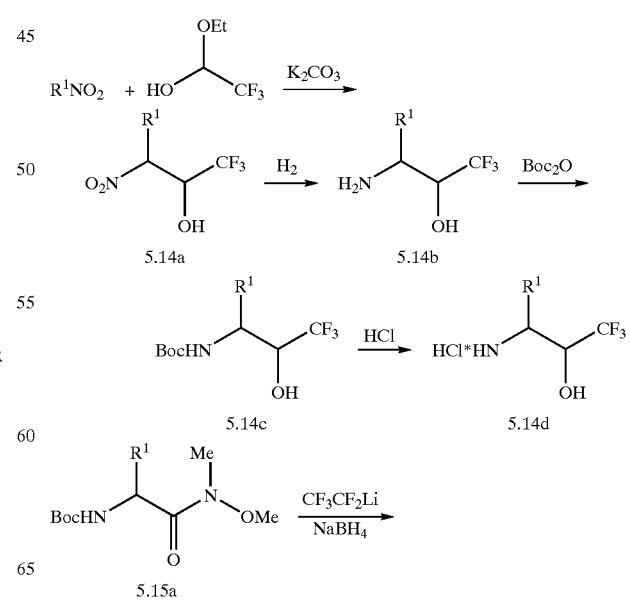

Scheme 5

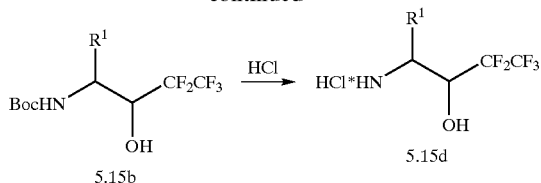

d) Synthesis of Difluoro α-ketoamide

Scheme 6 outlines the synthesis of hydroxy difluoro α-ketoamides (see: Veale et al., *J. Med. Chem.* 1997, 40, 3173–3181; Wolfe et al., *J. Med. Chem.* 1998, 41, 6–9). In Scheme 6, protected aminoaldehyde 6.16a (For preparation of α-aminoaldehyde, see: Fukuyama et al., *J. Am. Chem. Soc.* 10 1990, 112, 7050–7051 and Scheidt et al., *Bioorg. Med. Chem.* 1998, 6, 2477–2499) is reacted with 2-bromo-2,2-difluoroacetate to produce difluoro alcohol 6.16b. The alcohol 6.16b is hydrolyzed to the acid and coupled to an amine $H_2N$—Q to give 6.16c. The nitrogen protecting group Pg is removed according to procedures known to one skilled in the art (see Greene, T. W. in *Protective Groups in Organic Synthesis*, John Wiley & Sons, 2$^{nd}$ Ed, 1991), producing difluoro α-ketoamide 6.16d.

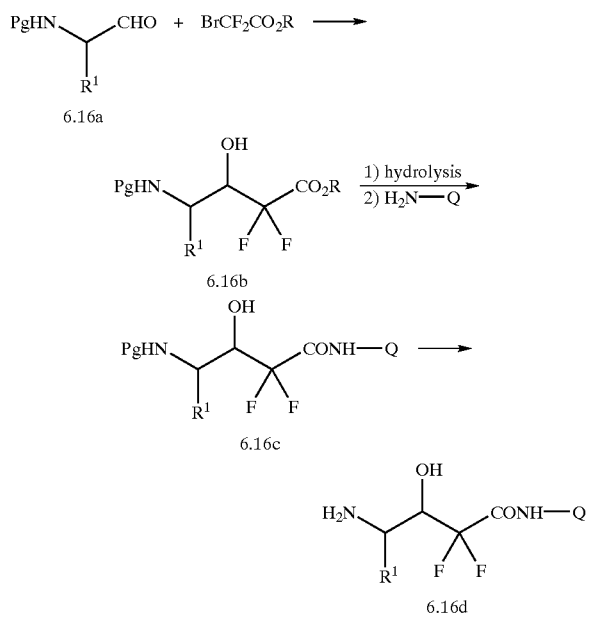

The serine traps described above are generally coupled to the free acid of the dihydropyrrolopyrazinone using known peptide coupling procedures, preferably by the phosphonium salt PyAOP (Carpino et al., *J. Chem. Soc., Chem. Commun.* 1994, 201–203). The alcohol functionality of the hydroxy serine trap is oxidized by procedures known to those skilled in the art, such as Dess-Martin periodinane method (Dess, D. B & Martin, J. C., *J. Org. Chem.* 1983, 48, 4155–4156) in the final step to give a compound of structure 1.11 and 1.12 wherein W contains an activated carbonyl.

When required, separation of the racemic material can be achieved by HPLC using a chiral column or by a resolution using a resolving agent such as camphonic chloride (Steven D. Young, et al, *Antimicrobial Agents and Chemotheraphy* 1995, 2602–2605). A chiral compound may also be directly synthesized using a chiral catalyst or a chiral ligand (Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Solution ratio express a volume relationship, unless stated otherwise. NMR chemical shifts (δ) are reported in parts per million. Flash chromatography was carried out on silica gel according to Still's method (Still et al., *J. Org. Chem.* 1978, 43, 2923). Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "HPLC" for high pressure liquid chromatography, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

As used throughout the specification, the following abbreviations for chemical reagents apply:

Boc is tert-butyloxycarbonyl,
Bz is benzoyl,
Cbz is benzyloxycarbonyl,
DCE is 1,2-dichloroethane,
DIEA is diethylpropyl amine,
DMAP is dimethylaminopyridine,
DMF is dimethylformamide,
DPPA is diphenylphosphoryl azide,
EDCI is 1-(3-dimethylaminopropyl)-3-ethylcarbodiimide hydrochloride,
HOAt is 1-hydroxy-7-azabenzotriazole,
LiHMDS is bis(trimethylsilyl)amide,
TBAI is tetrabutylammonium iodide,
TEA is triethylamine,
TFA is trifluoroacetic acid,
THF is tetrahydrofuran.

Example 1

Benzyl (6S)-6-[{(1R)-1-[(3aS,4S,6S,7aR)-hexahydro-3a,5,5-trimethyl-4,6-methano-1,3,2-benzodioxaborol-2-yl]amino}carbonyl]-4-oxo-4,6,7,8-tetrahydropyrrolo[1,2-a]pyrimidin-3-ylcarbamate

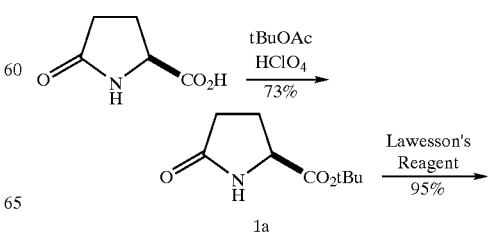

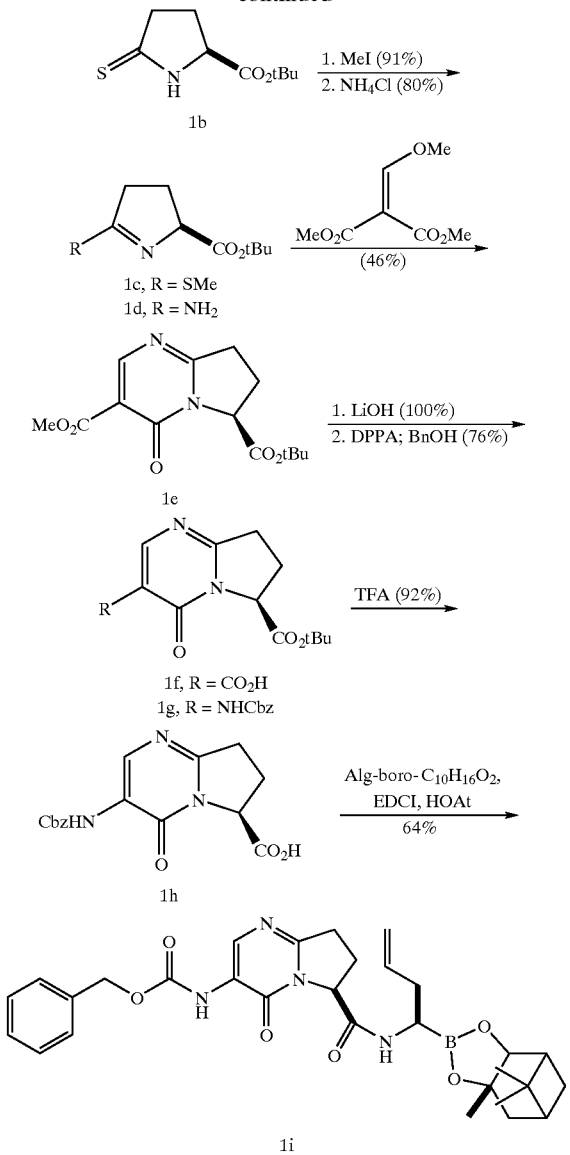

tert-Butyl (S)-5-(methylsulfanyl)-3,4-dihydro-2H-pyrrole-2-carboxylate (1c)

To a solution of thiolactam 1b (10.50 g, 52.2 mmol) in 200 mL THF at rt, was added MeI (13.0 mL, 208.7 mmol). The mixture was stirred for 3.5 h, then concentrated. The residue was partitioned between $CH_2Cl_2$ and sat. $NaHCO_3$ and the aqueous phase was extracted with $CH_2Cl_2$ (3×). The combined organic extract was dried ($Na_2SO_4$) and concentrated to afford 10.17 g (91%) of the title compound, 1c, as a brown oil. $^1$H NMR (300 MHz, $CDCl_3$) δ4.60 (dd, J=6.2, 7.3, 1H), 2.83–2.58 (m, 2H), 2.49 (s, 3H), 2.37–2.22 (m, 1H), 2.17–2.03 (m, 1H), 1.48 (s, 9H).

tert-Butyl (S)-5-amino-3,4-dihydro-2H-pyrrole-2-carboxylate hydrochloride (1d)

To a solution of 1c (10.17 g, 47.2 mmol) in 100 mL MeOH, was added $NH_4Cl$ (2.65 g, 49.6 mmol). The mixture was refluxed for 2 h, then concentrated. The residue was taken up in 200 mL $CHCl_3$ and stirred for 20 min until only a fine suspension persisted. The mixture was filtered and the filtrate concentrated. The solid was suspended in hexanes, sonicated, and then filtered and dried to afford 8.30 g (80%) of 1d as an off-white solid. $^1$H NMR (300 MHz, $CDCl_3$) δ4.44 (dd, J=8.8, 5.1, 1H), 3.11–3.05 (m, 2H), 2.58–2.45 (m, 1H), 2.28–2.15 (m,1H), 1.48 (s, 9H).

tert-Butyl (S)-5-amino-3,4-dihydro-2H-pyrrole-2-carboxylate (1e)

Amidine hydrochloride 1d (11.0 g, 49.8 mmol) was partitioned between $CHCl_3$ and sat. $K_2CO_3$. The layers were separated and the aqueous layer was extracted with $CHCl_3$ (2×). The combined organic phase was dried ($Na_2SO_4$) and concentrated to afford 8.50 g (93%) of free base 1e. $^1$H NMR (300 MHz, $CDCl_3$) δ4.44 (br s, 2H), 4.38 (dd, J=8.0, 5.5, 1H), 2.65–2.42 (m, 2H), 2.32–2.18 (m, 1H), 2.12–2.00 (m, 1H), 1.47 (s, 9H).

6-tert-Butyl 3-methyl (S)-4-oxo-4,6,7,8-tetrahydropyrrolo[1,2-a]pyrimidine-3,6-dicarboxylate (1f)

To a solution of dimethyl methoxymethylene malonate (8.68 g, 49.8 mmol) in 100 mL MeOH at −10° C., was added a solution of 1e (8.50 g, 46.1 mmol) in 100 mL MeOH over 1 h. The mixture was stirred at rt for 2 h, then was allowed to warm to rt overnight. The mixture was concentrated in vacuo and the resultant residue was purified by flash chromatography (50 to 100% EtOAc/hexanes) to afford 6.32 g (46%) of pyrimidinone 1f, as a colorless solid. $^1$H NMR (300 MHz, $CDCl_3$) δ8.69 (s, 1H), 5.03 (dd, J=9.7, 2.8, 1H), 3.90 (s, 3H), 3.38–3.09 (m, 2H), 2.64–2.49 (m, 1H), 2.34–2.23 (m, 1H), 1.49 (s, 9H).

(S)-6-(tert-Butoxycarbonyl)-4-oxo-4,6,7,8-tetrahydropyrrolo[1,2-a]pyrimidine-3-carboxylic acid (1g)

To a solution of 1f (14.15 g, 48.1 mmol) in 250 mL MeOH at 0° C. was slowly added aqueous LiOH (1M, 48 mL, 48 mmol) over 15 min. The reaction was allowed to warm to rt overnight with stirring. The organic solvent was removed in vacuo. The residual aqueous solution was partitioned with $Et_2O$, then the organic phase was extracted with $H_2O$ (2×). The combined aqueous extract was acidified to pH 2 with 1N HCl. The aqueous phase was extracted with $CHCl_3$ (3×). The combined organic extract was dried ($MgSO_4$) and concentrated to afford 11.4 g (85%) of the acid, 1g, as a tan crystalline solid.

tert-Butyl (S)-3-{[(benzyloxy)carbonyl]amino}-4-oxo-4,6,7,8-tetrahydropyrrolo[1,2-a]pyrimidine-6-carboxylate (1h)

A solution of carboxylic acid 1g (11.4 g, 40.7 mmol), triethylamine (5.67 mL, 40.7 mmol), and DPPA (8.86 mL, 40.7 mmol) in 180 mL 1,4-dioxane was heated at reflux for 2 h. Benzyl alcohol (4.67 mL, 45 mmol) was added and the mixture was heated at reflux for an additional 3 h. The mixture was concentrated in vacuo and the oil obtained was purified by flash chromatography (50 to 100% EtOAc/ tert-Butyl (S)-5-oxo-2-pyrrolidinecarboxylate (1a)

To a suspension of L-pyroglutamic acid (13.2 g, 102 mmol) in t-butyl acetate (200 mL), was added perchloric acid (70%, 9.7 mL, 113 mmol). The mixture was stirred at rt for 20 h, then poured into sat. $NaHCO_3$. $NaHCO_3$ (s) was added until neutral. The aqueous phase was extracted with EtOAc (6×). The combined organic extract was dried ($Na_2SO_4$) and concentrated to afford 13.68 g (72%) of the title compound, 1a. $^1$H NMR (300 MHz, $CDCl_3$) δ6.17 (br s, 1H), 4.13 (dd, J=7.4, 5.2, 1H), 2.44–2.31 (m, 3H), 2.22–2.15 (m, 1H), 1.47 (s, 9H).

tert-Butyl (S)-5-thioxo-2-pyrrolidinecarboxylate (1b)

To a solution of t-butyl pyroglutamate (1a) (10.12 g, 54.6 mmol) in benzene (250 mL), was added Lawesson's reagent (11.05 g, 27.3 mmol). The mixture was stirred at reflux for 15.5 h, then concentrated. The resultant residue was purified by flash chromatography (0 to 2 to 3 to 4% $MeOH/CHCl_3$) to afford 10.50 g (95%) of the title compound, 1b. $^1$H NMR (300 MHz, $CDCl_3$) δ7.27 (br s, 1H), 4.46–4.39 (m, 1H), 3.03–2.84 (m, 2H), 2.58–2.46 (m, 1H), 2.37–2.23 (m, 2H), 1.49 (s, 9H).

hexanes) to provide 11.13 g (73%) of the benzyl carbamate (1h) as a tan solid. $^1$H NMR (300 MHz, CDCl$_3$) δ8.67 (br s, 1H), 7.39–7.34 (m, 5H), 5.21 (s, 2H), 4.98 (dd, J=9.6, 3.0, 1H), 3.23–2.98 (m, 2H), 2.63–2.49 (m, 1H), 2.37–2.23 (m, 1H), 1.48 (s, 9H).

(6S)-3-{[(Benzyloxy)carbonyl]amino}-4-oxo-4,6,7,8-tetrahydropyrrolo[1,2-a]pyrimidine-6-carboxylic acid (1i)

tert-Butyl ester 1h (11.13 g, 28.9 mmol) was dissloved in 1:1 CH$_2$Cl$_2$/TFA. 1 mL H$_2$O was added and the mixture was stirred overnight at rt. The mixture was concentrated and the resultant residue was co-evaporated with CCl$_4$ (3×). The residual oil was triturated with 1:1 Et$_2$O/hexanes (100 mL) and the solid (9.0 g, 95%) was collected and dried, to provide 1i. $^1$H NMR (300 MHz, CDCl$_3$) δ8.69 (br s, 1H), MS (ESI) 330.3 (M+H$^+$); 328.3 (M–H$^+$).

To a solution of acid 1i (14.4 mg, 0.0438 mmol) and Alg-boro-C$_{10}$H$_{16}$O$_2$ (3-12e) (15 mg, 0.053 mmol) in 0.9 mL 5:1 CH$_2$Cl$_2$/DMF at 0° C., were added HOAt (6.6 mg, 0.048 mmol), NaHCO$_3$ (9.2 mg, 0.11 mmol), and EDCI (11.8 mg, 0.0613 mmol). The mixture was allowed to warm to rt over 19 h with stirring, then was concentrated. Purification by flash chromatography (EtOAc) afforded 15.7 mg (64%) of Example 1. $^1$H NMR (300 MHz, CDCl$_3$) δ8.67 (br s, 1H), 7.42–7.34 (m, 5H), 6.98 (d, J=5.5, 1H), 5.82–5.68 (m, 1H), 5.21 (s, 2H), 5.08 (d, J=8.8, 1H), 5.03 (d, J=5.5, 1H), 4.98 (s, 1H), 4.32 (dd, J=8.8, 1.9, 1H), 3.42–3.24 (m, 2H), 2.96 (dd, J=7.6, 17.5, 1H), 2.73 (dd, J=12.9, 6.8, 1H), 2.49–2.06 (m, 5H), 2.02 (t, J=5.5, 1H), 1.92–1.81 (m, 2H), 1.38 (s, 3H), 1.29–1.19 (m, 1H), 1.28 (s, 3H), 0.84 (s, 3H). MS (HR-ESI) calculated for C$_{30}$H$_{38}$BN$_4$O$_6$ (M+H$^+$), found 561.2905.

Example 2

Benzyl (6S)-6-[({(1R)-1-[(3aS,4S,6S,7aR)-hexahydro-3a,5,5-trimethyl-4,6-methano-1,3,2-benzodioxaborol-2-yl}amino)carbonyl]-4-oxo-4,6,7,8-tetrahydropyrrolo[1,2-a]pyrimidin-3-ylcarbamate According to the procedure for the preparation of Example 1, Acid 1i (42.5 mg, 0.129 mmol) and Etg-boro-C$_{10}$H$_{16}$O$_2$ (3-12e) (42.4 mg, 0.155 mmol) afforded 45.7 mg (65%) of Example 2. $^1$H NMR (300 MHz, CDCl$_3$) δ8.68 (br s, 1H), 7.41–7.34 (m, 5H), 6.93 (d, J=5.5, 1H), 5.21 (s, 2H), 5.07 (dd, J=8.8, 1.1, 1H), 4.32 (dd, J=8.8, 2.2, 1H), 3.43–3.28 (m, H), 3.17 (q, J=12.8, 6.6, 1H), 3.01–2.93 (m, 1H), 2.75–2.68 (m, 1H), 2.38–2.28 (m, 2H), 2.26–2.14 (m, 1H), 2.03 (t, J=5.0, 1H), 1.92–1.81 (m, 2H), 1.78–1.65 (m, 2H), 1.39 (s, 3H), 1.20 (d, J=11.0, 1H), 1.28 (s, 3H), 0.92 (t, J=7.4, 1H), 0.84 (s, 3H); MS (HR-ESI) calculated for C$_{29}$H$_{38}$BN$_4$O$_6$ (M+H$^+$), found 549.2867.

Example 3

(6S)-N-{(1R)-1-[(3aS,4S,6S,7aR)-Hexahydro-3a,5,5-trimethyl-4,6-methano-1,3,2-benzodioxaborol-2-yl]propyl}-3-amino-4-oxo-4,6,7,8-tetrahydropyrrolo[1,2-a]pyrimidine-6-carboxamide hydrochloride To Example 2 (44.0 mg, 0.0802 mmol) and 10% Pd-C (10 mg) in 3 mL MeOH, was added 1 drop of conc. HCl. The mixture was evacuated and flushed with H$_2$ (3×), then stirred under an atmosphere of H$_2$ for 1 h. The mixture was filtered and concentrated to afford 35.8 mg (99%) of Example 3 as the HCl salt. MS (HR-ESI) calculated for C$_{21}$H$_{32}$BN$_4$O$_4$ (M+H$^+$), found 415.2497.

Example 4

(6S)-N-{(1R)-1-[(3aS,4S,6S,7aR)-Hexahydro-3a,5,5-trimethyl-4,6-methano-1,3,2-benzodioxaborol-2-yl]propyl}-3-(benzylamino)-4-oxo-4,6,7,8-tetrahydropyrrolo[1,2-a]pyrimidine-6-carboxamide To Example 3 (5.0 mg, 0.011 mmol) in 0.5 mL DCE, were added TEA (1.5 µL, 0.011 mmol), AcOH (3.2 µL, 0.055 mmol), benzaldehyde (2.3 µL, 0.022 mmol), and Na(OAc)$_3$BH (4.7 mg, 0.022 mmol). The mixture was stirred at rt for 16 h. Additional benzaldehyde (11.3 µL, 0.111 mmol) and Na(OAc)$_3$BH (23.5 mg, 0.111 mmol) were added and stirring was continued for 4 h. The reaction was diluted with EtOAc, washed with sat. NaHCO$_3$ and brine, dried (Na$_2$SO$_4$), and concentrated. Purification by flash chromatography (5% MeOH/EtOAc) afforded 5.4 mg (97%) of Example 4. MS (HR-ESI) calculated for C$_{28}$H$_{38}$BN$_4$O$_4$ (M+H$^+$), found 505.3010.

Example 5

(6S)-N-{(1R)-1-[(3aS,4S,6S,7aR)-Hexahydro-3a,5,5-trimethyl-4,6-methano-1,3,2-benzodioxaborol-2-yl]propyl}-4-oxo-3-{[3-(trifluoromethyl)benzyl]amino}-4,6,7,8-tetrahydropyrrolo[1,2-a]pyrimidine-6-carboxamide According to the procedure for the preparation of Example 4, amine Example 3 (5.0 mg, 0.11 mmol) and 3-trifluoromethyl benzaldehyde (17.5 µL, 0.133 mmol) afforded 4.7 mg (74%) of Example 5. MS (HR-ESI) calculated for C$_{29}$H$_{37}$BF$_3$N$_4$O$_4$ (M +H$^+$), found 573.2884.

Example 6

(6S)-N-{(1R)-1-[(3aS,4S,6S,7aR)-Hexahydro-3a,5,5-trimethyl-4,6-methano-1,3,2-benzodioxaborol-2-yl]propyl}-3-(benzoylamino)-4-oxo-4,6,7,8-tetrahydropyrrolo[1,2-a]pyrimidine-6-carboxamide To a solution of amine HCl salt Example 3 (5.0 mg, 0.011 mmol) in 1 mL CH$_2$Cl$_2$, were added DMAP (catalytic), BzCl (1 drop), TEA (2 drops). The mixture was stirred at rt for 16.5 h, then concentrated. Purification by flash chromatography (5% MeOH/EtOAc) afforded 4.5 mg (78%) of Example 6. MS (HR-ESI) calculated for C$_{28}$H$_{36}$BN$_4$O$_5$ (M+H$^+$), found 519.2773.

Example 7

(6S)-N-{(1R)-1-[(3aS,4S,6S,7aR)-Hexahydro-3a,5,5-trimethyl-4,6-methano-1,3,2-benzodioxaborol-2-yl]propyl}-3-(acetylamino)-4-oxo-4,6,7,8-tetrahydropyrrolo[1,2-a]pyrimidine-6-carboxamide According to the procedure for the preparation of Example 6, amine HCl salt Example 3 (5.0 mg, 0.011 mmol) and AC$_2$O (1 drop) afforded 3.4 mg (67%) of Example 7. MS (HR-ESI) calculated for C$_{23}$H$_{34}$BN$_4$O$_5$ (M+H$^+$), found 457.2606.

Example 8

Benzyl (6S,8RS)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-4-oxo-8-(3-phenylpropyl)-4,6,7,8-tetrahydropyrrolo[1,2-a]pyrimidin-3-ylcarbamate

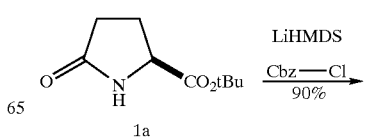

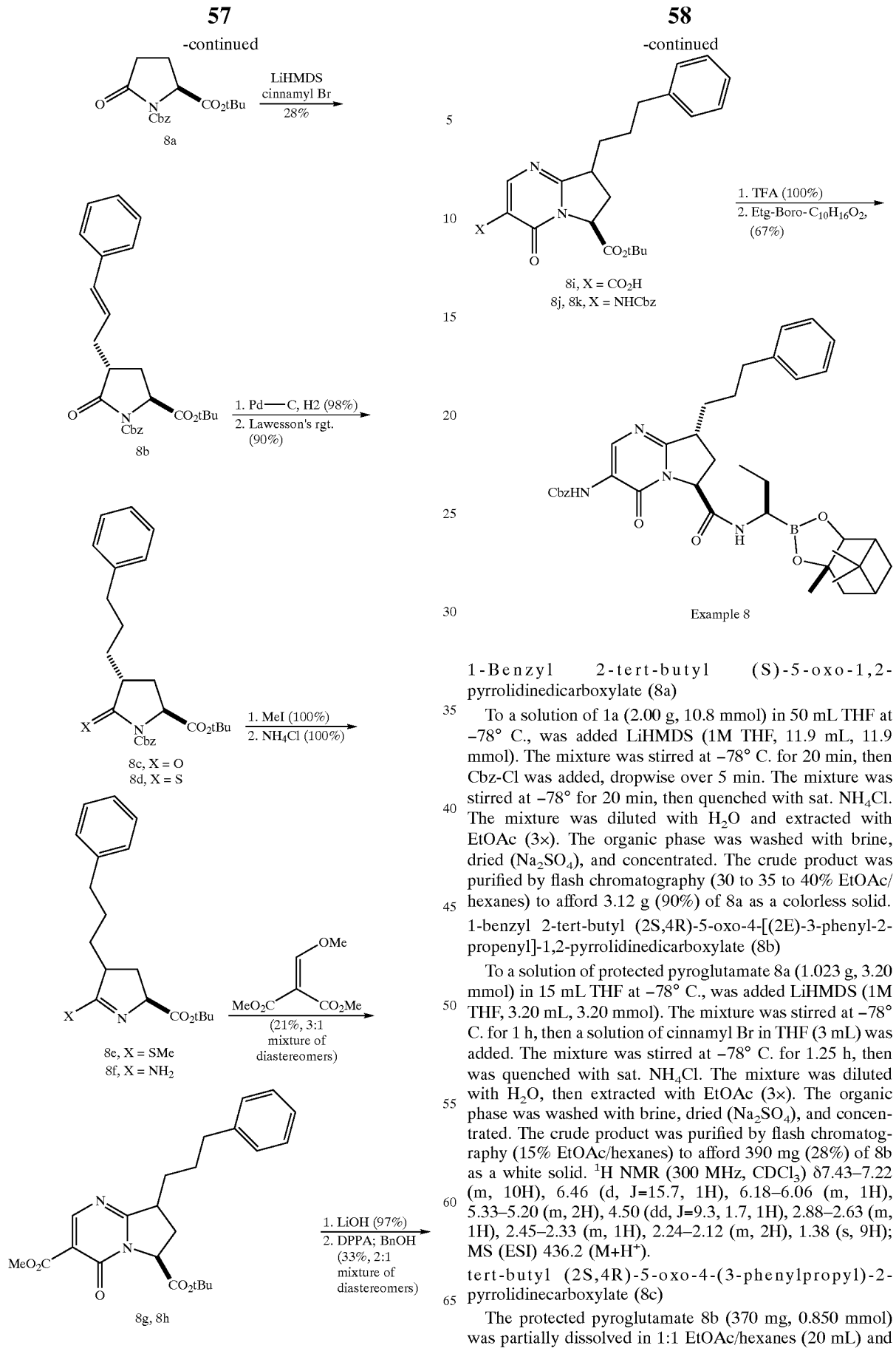

1-Benzyl 2-tert-butyl (S)-5-oxo-1,2-pyrrolidinedicarboxylate (8a)

To a solution of 1a (2.00 g, 10.8 mmol) in 50 mL THF at −78° C., was added LiHMDS (1M THF, 11.9 mL, 11.9 mmol). The mixture was stirred at −78° C. for 20 min, then Cbz-Cl was added, dropwise over 5 min. The mixture was stirred at −78° for 20 min, then quenched with sat. NH$_4$Cl. The mixture was diluted with H$_2$O and extracted with EtOAc (3×). The organic phase was washed with brine, dried (Na$_2$SO$_4$), and concentrated. The crude product was purified by flash chromatography (30 to 35 to 40% EtOAc/hexanes) to afford 3.12 g (90%) of 8a as a colorless solid.

1-benzyl 2-tert-butyl (2S,4R)-5-oxo-4-[(2E)-3-phenyl-2-propenyl]-1,2-pyrrolidinedicarboxylate (8b)

To a solution of protected pyroglutamate 8a (1.023 g, 3.20 mmol) in 15 mL THF at −78° C., was added LiHMDS (1M THF, 3.20 mL, 3.20 mmol). The mixture was stirred at −78° C. for 1 h, then a solution of cinnamyl Br in THF (3 mL) was added. The mixture was stirred at −78° C. for 1.25 h, then was quenched with sat. NH$_4$Cl. The mixture was diluted with H$_2$O, then extracted with EtOAc (3×). The organic phase was washed with brine, dried (Na$_2$SO$_4$), and concentrated. The crude product was purified by flash chromatography (15% EtOAc/hexanes) to afford 390 mg (28%) of 8b as a white solid. $^1$H NMR (300 MHz, CDCl$_3$) δ7.43–7.22 (m, 10H), 6.46 (d, J=15.7, 1H), 6.18–6.06 (m, 1H), 5.33–5.20 (m, 2H), 4.50 (dd, J=9.3, 1.7, 1H), 2.88–2.63 (m, 1H), 2.45–2.33 (m, 1H), 2.24–2.12 (m, 2H), 1.38 (s, 9H); MS (ESI) 436.2 (M+H$^+$).

tert-butyl (2S,4R)-5-oxo-4-(3-phenylpropyl)-2-pyrrolidinecarboxylate (8c)

The protected pyroglutamate 8b (370 mg, 0.850 mmol) was partially dissolved in 1:1 EtOAc/hexanes (20 mL) and 100 □L AcOH. To this mixture, was added 10% Pd-C (50 mg). The mixture was evacuated and flushed with $H_2$ (5×), then stirred under an atmosphere of $H_2$ for 45 min. The reaction mixture was filtered and concentrated to afford 251.4 mg (98%) of 8c.

tert-butyl (2S,4RS)-4-(3-phenylpropyl)-5-thioxo-2-pyrrolidinecarboxylate (8d)

A mixture of pyroglutamate 8c (245.4 mg, 0.809 mmol) and Lawesson's reagent (164 mg, 0.404 mmol) in 6 mL benzene was stirred at reflux for 17 h, then concentrated. The crude product was purified by flash chromatography (0.5 to 1 to 1.5 to 2% MeOH/CHCl$_3$) to afford 232 mg (90%) of the thiolactam 8d as a 2:1 mixture of diastereomers.

tert-butyl (2S,5RS)-5-(methylsulfanyl)-4-(3-phenylpropyl)-3,4-dihydro-2H-pyrrole-2-carboxylate (8e)

To a solution of thiolactam 8d (232 mg, 0.726 mmol) in 5 mL THF, was added MeI (181 μL, 2.90 mmol). The mixture was stirred at rt for 15 h, then was poured into sat. NaHCO$_3$. The mixture was extracted with CH$_2$Cl$_2$ (3×). The combined organic extract was washed (brine), dried (Na$_2$SO$_4$), and concentrated to afford 242 mg (quantitative) of 8e.

tert-butyl (2S,5RS)-5-amino-4-(3-phenylpropyl)-3,4-dihydro-2H-pyrrole-2-carboxylate (8f)

A solution of 8e (242 mg, 0.726 mmol) and NH$_4$Cl (40.8 mg, 0.726 mmol) in 4 mL MeOH was stirred at reflux for 2.75 h, then evaporated. The mixture was dissolved in CHCl$_3$ and poured in aq. K$_2$CO$_3$. The layers were separated and the aqueous was extracted with CHCl$_3$ (3×). The combined organic was washed with brine, dried (Na$_2$SO$_4$), and concentrated to afford 219 mg (quantitative) of 8f.

6-tert-butyl 3-methyl (6S)-4-oxo-8-(3-phenylpropyl)-4,6,7,8-tetrahydropyrrolo[1,2-a]pyrimidine-3,6-dicarboxylate (C8 diastereomers, 8 g and 8 h)

To a solution of dimethylmethoxymethylene malonate (126 mg, 0.726 mmol) in 3 mL MeOH at −15° C., amidine 8f (219 mg, 0.726 mmol) was added, dropwise. The mixture was stirred at 0° C., was allowed to warm to rt and stir 18 h, then was concentrated. The crude residue was purified by flash chromatography (15 to 25 to 35 to 45 to 55 to 65 to 100% EtOAc/hexanes) to afford 46.0 mg (15%) of 8g and 18.5 mg (6%) of 8h. MS (ESI) 435.1 (M+Na$^+$), 476.1 (M+Na$^+$+CH$_3$CN) observed for both diastereomers.

(6S,8RS)-6-(tert-butoxycarbonyl)-4-oxo-8-(3-phenylpropyl)-4,6,7,8-tetrahydropyrrolo[1,2-a]pyrimidine-3-carboxylic acid (8i)

Methyl ester 8g (46 mg, 0.112 mmol) was dissolved in 1 mL MeOH at 0° C. To this solution, was added 1M LiOH (112 μL, 0.112 mmol). The mixture was allowed to slowly warm to rt with stirring for 22 h. The volatiles were evaporated. The mixture was diluted with Et$_2$O and extracted with H$_2$O (3×). The aqueous was acidified to pH 2, then extracted with EtOAc (3×). The combined organic was dried (a$_2$SO$_4$) and concentrated. Methyl ester 8h (18.5 mg) was treated in the same fashion. The products of the two reactions were combined to afford 57.6 mg (92%) of acid 8i as a 1:1 diastereomeric mixture. $^1$H NMR (300 MHz, CDCl$_3$) δ8.95 (s, 1H), 7.32–7.15 (m, 5H), 5.02 (dd, J=9.9, 1.9, 0.5H), 4.93 (dd, J=9.9, 4.7, 0.5H), 3.47–3.28 (m, 1H), 2.88–2.77 (m, 0.5H), 2.75–2.60 (m, 2H), 2.56–2.49 (m, 0.5H), 2.26–2.01 (m, 2H), 1.83–1.58 (m, 3H), 1.48 (s, 4.5H), 1.45 (s, 4.5H).

tert-Butyl (6S,8RS)-3-{[(benzyloxy)carbonyl]amino}-4-oxo-8-(3-phenylpropyl)-4,6,7,8-tetrahydropyrrolo[1,2-a]pyrimidine-6-carboxylate (C8 diastereomers 8j and 8k)

8i (57.6 mg, 0.145 mmol), TEA (20.1 μL, 0.145 mmol), and DPPA (31.2 μL, 0.145 mmol) were stirred at reflux in 2 mL dioxane for 2 h. Benzyl alcohol (16.5 μL, 0.159 mmol) was added. The reaction was stirred at reflux for an additional 4 h, then concentrated. The crude reaction mixture was purified by flash chromatography (20 to 30 to 40 to 50% EtOAc/hexanes) to afford 14.5 mg (20%) of diastereomer 8j and 9.6 mg (13%) of diastereomer 8k.

C8 diastereomer 8j (less polar): $^1$H NMR (300 MHz, CDCl$_3$) δ8.68 (br s, 1H), 7.40–7.16 (m, 10H), 5.26 (d, J=8.4, 1H), 5.21 (s, 2H), 4.92 (dd, J=9.7, 2.0, 1H), 3.29–3.18 (m, 1H), 2.77–2.59 (m, 2H), 2.48–2.40 (m, 1H), 2.21–2.06 (m, 2H), 1.81–1.69 (m, 2H), 1.46 (s, 9H); MS (ESI) 504.1 (M+H$^+$), 526.1 (M+Na$^+$).

C8 diastereomer 8k (more polar): $^1$H NMR (300 MHz, CDCl$_3$) δ8.68 (br s, 1H), 7.40–7.16 (m, 10H), 5.20 (d, J=1.4, 2H), 4.82 (dd, J=9.7, 4.9, 1H), 3.21–3.10 (m, 1H), 2.78–2.60 (m, 4H), 2.02–1.93 (m, 2H), 1.83–1.70 (m, 2H), 1.44 (s, 9H); MS (ESI) 504.1 (M+H$^+$), 526.1 (M+Na$^+$).

8j (14.5 mg, 0.0288 mmol) was stirred in 1:1 CH$_2$Cl$_2$/TFA (1 mL) and 1 drop H$_2$O for 5 h, then concentrated. The residue was combined with Etg-boro-C$_{10}$H$_{16}$O$_2$ (3-12e) (11.8 mg, 0.043 mmol) in 5:1 CH$_2$Cl$_2$/DMF (600 μL) at 0° C. To this solution was added HOAt (4.3 mg, 0.032 mmol), NaHCO$_3$ (6.0 mg, 0.072 mmol), and EDCI (7.7 mg, 0.040 mmol). The mixture was allowed to warm to rt and stir for 15 h. The reaction mixture was diluted with EtOAc. The organic phase was washed with H$_2$O, 0.1 N HCl, sat. NaHCO$_3$, and brine, dried (Na$_2$SO$_4$), and concentrated. The crude product was purified by flash chromatography (40% EtOAc/hexanes) to afford 12.9 mg (67%) of Example 8. MS (HR-ESI) calculated for C$_{38}$H$_{48}$BN$_4$O$_6$ (M+H$^+$), found 667.3674.

Example 9

Benzyl (6S,8S)-6-[(}(1R)-1-[(3aS,4S,6S,7aR)-hexahydro-3a,5,5-trimethyl-4,6-methano-1,3,2-benzodioxaborol-2-yl]propyl}amino)carbonyl]-4-oxo-8-(3-phenylpropyl)-4,6,7,8-tetrahydropyrrolo[1,2-a]pyrimidin-3-ylcarbamate According to the procedure for the preparation of Example 8, diastereomer 8k (more polar) (9.6 mg, 0.0191 mmol) afforded 5.8 mg (46%) of Example 9. MS (HR-ESI) calculated for C$_{38}$H$_{48}$BN$_4$O$_6$ (M+H$^+$), found 667.3660.

Example 10

(6S,8R)-N-{(1R)-1-[(3aS,4S,6S,7aR)-Hexahydro-3a,5,5-trimethyl-4,6-methano-1,3,2-benzodioxaborol-2-yl]propyl}-4-oxo-8-(3-phenylpropyl)-3-{[3-(trifluoromethyl)benzyl]amino}-4,6,7,8-tetrahydropyrrolo[1,2-a]pyrimidine-6-carboxamide Example 8 (12.2 mg, 0.0183 mmol) and cat. 10% Pd-C were taken up in 2 mL MeOH and 1 drop conc. HCl. The mixture was evacuated and flushed with H$_2$ (3×) and stirred under an atmosphere of H$_2$ for 1 h. The mixture was filtered and concentrated to afford the amine as the HCl salt. To a solution of the amine in DCE (1 mL), was added m-trifluoromethylbenzaldehyde (23 μL, 0.18 mmol), TEA (2.5 μL, 0.018 mmol), AcOH (5.1 μL, 0.089 mmol), and Na(OAc)$_3$BH (37.6 mg, 0.178 mmol). The mixture was stirred at rt for 24 h, then was diluted with EtOAc. The organic phase was washed with sat. NaHCO$_3$ (2×) and brine, dried (Na$_2$SO$_4$), and concentrated. The crude product was purified by flash chromatography (40% EtOAc/hexanes+ 0.5% MeOH) to afford 8.4 mg (68%) of Example 10. MS (ESI) 691.4 (M+H$^+$), 713.3 (M+Na$^+$); 689.4 (M−H$^+$); MS (HR-ESI) calculated for C$_{38}$H$_{47}$BF$_3$N$_4$O$_4$ (M+H$^+$), found 691.3664.

Example 11

(6S,8S)-N-{(1R)-1-[(3aS,4S,6S,7aR)-Hexahydro-3a,5,5-trimethyl-4,6-methano-1,3,2-benzodioxaborol-2-yl]propyl}-4-oxo-8-(3-phenylpropyl)-3-{[3-(trifluoromethyl)benzyl]amino}-4,6,7,8-tetrahydropyrrolo[1,2-a]pyrimidine-6-carboxamide According to the procedure for the preparation of Example 10, Example 9 (4.7 mg, 0.0071 mmol) afforded 2.0 mg (41%) of Example 11. MS (ESI) 691.4 (M+H$^+$), 713.4 (M+Na$^+$); 689.4 (M–H$^+$); MS (HR-ESI) calculated for $C_{38}H_{47}BF_3N_4O_4$ (M+H$^+$), found 691.3667.

Example 12

(6S,8R)-N-{(1R)-1-[(3aS,4S,6S,7aR)-Hexahydro-3a,5,5-trimethyl-4,6-methano-1,3,2-benzodioxaborol-2-yl]propyl]}-8-(benzoylamino)-8-methyl-4-oxo-3-{[3-(trifluoromethyl)benzyl]amino}-4,6,7,8-tetrahydropyrrolo[1,2-a]pyrimidine-6-carboxamide

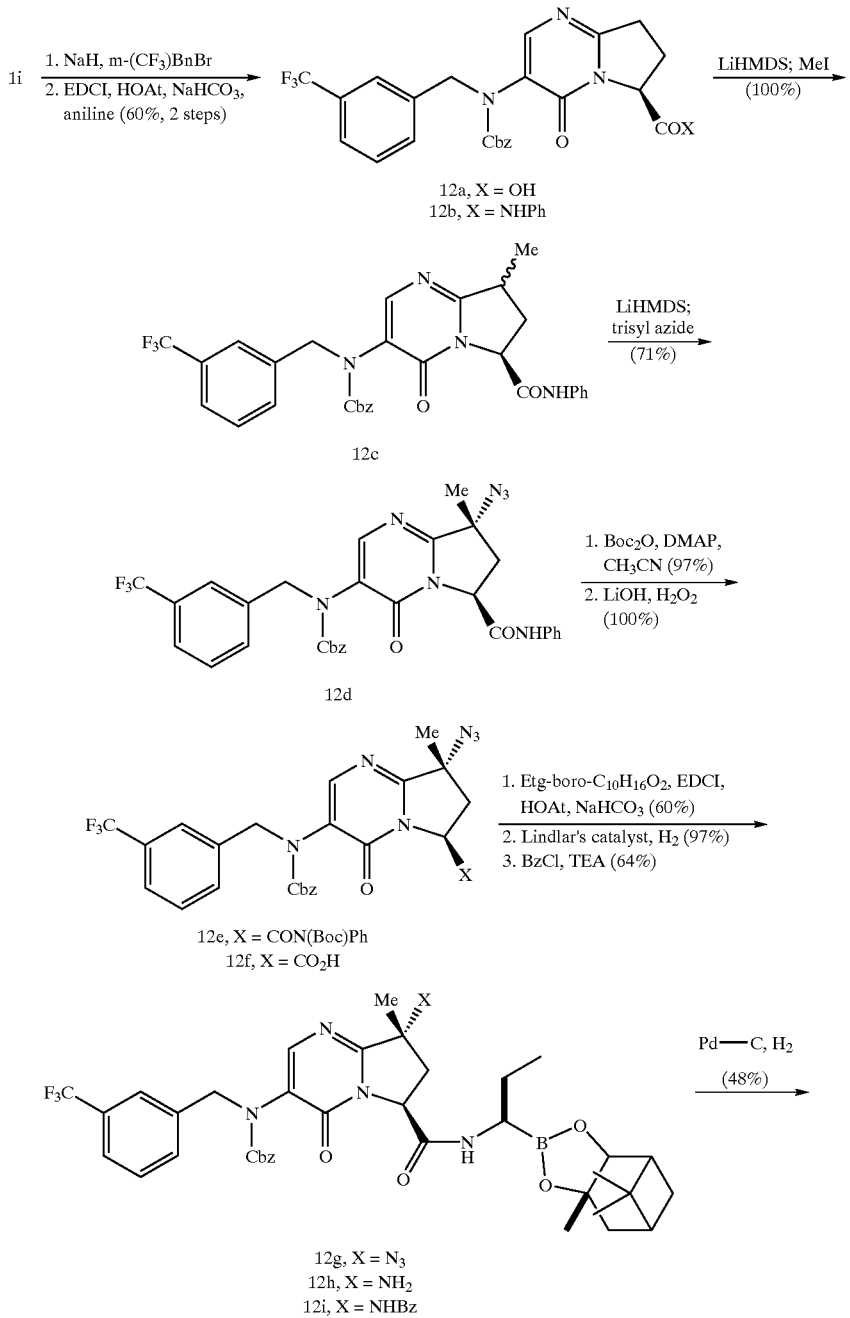

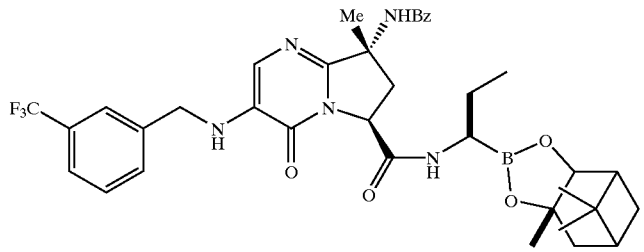

Example 12

(6S)-3-{[(Benzyloxy)carbonyl][3-(trifluoromethyl)benzyl]amino}-4-oxo-4,6,7,8-tetrahydropyrrolo[1,2-a]pyrimidine-6-carboxylic acid (12a)

To a mixture of acid 1i (4.50 g, 13.7 mmol) in 70 mL THF at 0° C., was added 3-(trifluoromethyl)benzyl bromide (8.35 mL, 54.7 mmol), NaH (60% dispersion in oil, 1.64 g, 41.4 mmol), and TBAI (100 mg, catalytic). The reaction was stirred at rt for 15 h, then quenched with the addition of 50 mL $H_2O$. The volatile solvents were removed by rotary evaporation and the aqueous solution obtained was partitioned with $Et_2O$. The organic phase was extracted with 20% sat. $NaHCO_3$ (3×). The combined organic extract was acidified with 1N HCl and extracted with EtOAc (5×). The combined organic extract was washed (brine), dried ($Na_2SO_4$), and concentrated to afford 6.18 g (93%) of the 3-(trifluoromethyl)benzyl amine (12a), which was used in the following step without additional purification.

Benzyl (6S)-6-(anilinocarbonyl)-4-oxo-4,6,7,8-tetrahydropyrrolo[1,2-a]pyrimidin-3-yl[3-(trifluoromethyl)benzyl]carbamate (12b)

To a solution of 12a (6.18 g, 12.7 mmol) and aniline (1.64 mL, 19.0 mmol) in 60 mL 5:1 $CH_2Cl_2$/DMF at 0° C., was added HOAt (1.90 g, 14.0 mmol), $NaHCO_3$ (2.13 g, 25.4 mmol), and EDCI (3.41 g, 17.8 mmol). The mixture was stirred and allowed to warm to rt over 15 h. The reaction was diluted with EtOAc and the organic phase was washed with $H_2O$, sat. $NaHCO_3$, $H_2O$, 1N HCl, $H_2O$, and brine. The organic phase was dried ($Na_2SO_4$) and concentrated. The residue obtained was purified by flash chromatography (50 to 60 to 70% EtOAc/hexanes) to afford 4.60 g (60%, 2 steps) of 12b as an off-white solid. $^1$H NMR (300 MHz, $CDCl_3$) δ9.35 (br s, 1H), 7.68 (br s, 1H), 7.52–7.21 (m, 13H), 7.07 (t, J=7.5, 1H), 5.28 (dd, J=8.7, 0.5, 1H), 5.22–5.11 (m, 2H), 4.84 (br s, 2H), 3.47–3.34 (m, 1H), 3.04–2.95 (m, 1H), 2.80 (br t, J=10.5, 1H), 2.44–2.30 (m, 1H). MS (ESI) 563.5 (M+H$^+$), 35 585.5 (M+Na$^+$), 561.4 (M−H$^+$).

Benzyl (6S,8RS)-6-(anilinocarbonyl)-8-methyl-4-oxo-4,6,7,8-tetrahydropyrrolo[1,2-a]pyrimidin-3-yl[3-(trifluoromethyl)benzyl]carbamate (12c)

To a solution of phenyl amide 12b (1.00 g, 1.78 mmol) in 10 mL THF at −78° C., was added LIHMDS (1M in THF, 3.73 mL, 3.73 mmol). The orange solution was stirred at −78° C. for 10 min, then MeI (1.11 mL, 17.8 mmol) was added. The reaction was allowed to slowly warm to −35° C. over 1.5 h with stirring, then was quenched with the addition of sat. $NH_4Cl$. The mixture was diluted with EtOAc. The organic phase was washed with sat. $NH_4Cl$, 10% $Na_2SO_3$ (2×), and brine and dried ($Na_2SO_4$). The organic phase was filtered through a 2" pad of $SiO_2$, rinsing with EtOAc, and concentrated to afford 1.02 g (quantitative) of a 2:1 diastereomeric mixture of methylated products (12c) as an off-white solid. $^1$H NMR (300 MHz, $CDCl_3$) δ9.41 (br s, 1H), 7.51–7.28 (m, 15H), 7.10 (t, J=7.4, 1H), 5.25–5.12 (m, 3H), 4.85 (br s, 2H), 3.63–3.56 (m, 0.7H), 3.30–3.23 (m, 0.3H), 3.13–3.04 (m, 0.7H), 2.64–2.57 (m, 0.6H), 2.07–1.97 (m, 0.7H), 1.48 (d, J=7.3, 1H), 1.38 (d, J=7.0, 2H); MS (ESI) 599.4 (M+Na$^+$), 575.4 (M−H$^+$).

Benzyl (6S,8R)-6-(anilinocarbonyl)-8-azido-8-methyl-4-oxo-4,6,7,8-tetrahydropyrrolo[1,2-a]pyrimidin-3-yl[3-(trifluoromethyl)benzyl]carbamate (12d)

To a solution of the methyl diastereomers (12c) (1.02 g, 1.78 mmol) in 10 mL THF at −78° C., was added LiHMDS (1M in THF, 3.73 mL, 3.73 mmol). The red solution was stirred at −78° C. for 10 min, then a solution of trisyl azide (606 mg, 1.96 mmol) in 2 mL THF was added. The reaction was stirred at −78° C. for 1.5 h, then was quenched with the addition of AcOH (459 μL, 8.01 mmol). The mixture was stirred at rt for 1 h, then was diluted with EtOAc. The organic phase was washed with sat. $NH_4Cl$ and brine, dried ($Na_2SO_4$), and concentrated. The product was purified by flash chromatography (30 to 35% EtOAc/hexanes) to afford 784 mg (71%) of azide (12d). $^1$H NMR (300 MHz, $CDCl_3$) δ9.26 (br s, 1H), 7.82 (br s, 1H), 7.51–7.25 (m, 13H), 7.10 (t, J=7.3, 1H), 5.23 (m, 3H), 4.91–4.77 (m, 2H), 2.90 (d, J=13.9, 1H), 2.43 (dd, J=13.6, 9.2, 1H), 1.87 (s, 3H); MS (ESI) 640.4 (M+Na$^+$), 616.4 (M−H$^+$).

tert-Butyl (6S,8R)-(8-azido-3-{[(benzyloxy)carbonyl][3-(trifluoromethyl)benzyl]amino}-8-methyl-4-oxo-4,6,7,8-tetrahydropyrrolo[1,2-a]pyrimidin-6-yl)carbonyl(phenyl)carbamate (12e)

To a solution of amide 12d (778 mg, 1.26 mmol) in 6 mL $CH_3CN$ at rt, was added DMAP (137 mg, 0.63 mmol) and $Boc_2O$ (462 mg, 3.78 mmol). The mixture was stirred at rt for 10 min, then was diluted with EtOAc. The organic phase was washed with 1N HCl, $H_2O$, and brine, dried ($Na_2SO_4$), and concentrated. The residue obtained was purified by flash chromatography (25% EtOAc/hexanes) to afford 880 mg (97%) of imide 12e. $^1$H NMR (300 MHz, $CDCl_3$) δ7.67 (br s, 1H), 7.53–7.18 (m, 14H), 5.93 (dd, J=9.4, 5.0, 1H), 5.23–5.14 (m, 2H), 4.93–4.69 (m, 2H), 2.88 (dd, J=14.3, 9.3, 1H), 2.43 (dd, J=14.3, 4.8, 1H), 1.76 (s, 3H), 1.40 (s, 9H); MS (ESI) 740.5 (M+Na$^+$), 716.4 (M−H$^+$).

(6S,8R)-8-Azido-3-{[(benzyloxy)carbonyl][3-(trifluoromethyl)benzyl]amino}-8-methyl-4-oxo-4,6,7,8-tetrahydropyrrolo[1,2-a]pyrimidine-6-carboxylic acid (12f)

To a solution of 12e in 5 mL THF/$H_2O$ (4:1) at 0° C., was added 30% $H_2O_2$ (556 μL, 4.90 mmol) and 1N LiOH (1.97 mL, 1.97 mmol). The mixture was stirred at 0° C. of 2 h, then $Na_2SO_3$ (618 mg, 4.90 mmol) in 3 mL $H_2O$ was added. The mixture was stirred 15 min, then diluted with EtOAc and acidified with 1N HCl. The aqueous was extracted with EtOAc (5×). The combined organic extract was washed with brine and concentrated to afford 890 mg (quantitative) of a 1:1 mixture of acid (12f) and BocNHPh, which was used in the following step with out further purification.

Benzyl (6S,8R)-8-azidio-6-({[(1R)-1-[(3aS,4S,6S,7aR)-hexahydro-3a,5,5-trimethyl-4,6-methano-1,3,2- benzodioxaborol-2-ylpropyl]amino}carbonyl)-8-methyl-4-oxo-4,6,7,8-tetrahydropyrrolo[1,2-a]pyrimidin-3-yl[3-(trifluoromethyl)benzyl]carbamate (12g)

To a solution of 12f (1.23 mmol) and Etg-boro-$C_{10}H_{16}O_2$ (3-12e) (470.6 mg, 1.72 mmol) in 12 mL 5:1 $CH_2Cl_2$/DMF at 0° C., was added HOAt (184 mg, 1.35 mmol), $NaHCO_3$ (258 mg, 3.08 mmol), and EDCI (331 mg, 1.72 mmol). The mixture was allowed to slowly warm to rt and stir for 14.5 h. The reaction was diluted with EtOAc and the organic phase was washed with $H_2O$, sat. $NaHCO_3$, $H_2O$, 1N HCl, $H_2O$, and brine. The organic phase was dried ($Na_2SO_4$) and concentrated. The residue obtained was purified by flash chromatography (40% EtOAc/hexanes) to afford 564 mg (60%, 2 steps from imide 12e) of boronate ester (12g). $^1H$ NMR (300 MHz, $CDCl_3$) δ7.74 (br s, 1H), 7.52 (s, 2H), 7.43 (s, 2H), 7.35–7.25 (m, 5H), 6.85 (d, J=5.5, 1H), 5.18 (s, 2H), 4.97–4.89 (m, 2H), 4.70 (d, J=15.7, 1H), 4.32 (dd, J=8.8, 1.8, 1H), 3.23–3.16 (m, 1H), 2.71 (dd, J=13.5, 3.3, 1H), 2.51–2.30 (m, 2H), 2.25–2.17 (m, 1H), 2.02 (q, J=5.5, 1H), 1.96–1.88 (m, 1H), 1.87–1.80 (m, 1H), 1.84 (s, 1H), 1.78–1.56 (m, 2H), 1.39 (s, 3H), 1.29 (s, 3H), 1.19 (d, J=11.0, 1H), 0.95 (t, J=6.3, 1H), 0.84 (s, 3H); MS (ESI) 784.3 (M+$Na^+$), 760.3 (M–$H^+$).

Benzyl (6S,8R)-6-({[(1R)-1-[(3aS,4S,6S,7aR)-hexahydro-3a,5,5-trimethyl-4,6-methano-1,3,2-benzodioxaborol-2-ylpropyl]amino}carbonyl)-8-amino-8-methyl-4-oxo-4,6,7,8-tetrahydropyrrolo[1,2-a]pyrimidin-3-yl[3-(trifluoromethyl)benzyl]carbamate (12h)

To a solution of azide 12g (7.5 mg, 0.0099 mmol) in 2 mL MeOH, was added Lindlar's catalyst (5 mg). The mixture was evacuated and flushed with $H_2$ (3×), stirred under an atmosphere of $H_2$ for 1 h, then filtered. The solution was concentrated to afford 7.0 mg (97%) of amine 12h as a colorless residue. MS (ESI) 736.6 (M+$H^+$), 758.6 (M+$Na^+$), 734.5 (M–$H^+$).

Benzyl (6S,8R)-6-({[(1R)-1-[(3aS,4S,6S,7aR)-hexahydro-3a,5,5-trimethyl-4,6-methano-1,3,2-benzodioxaborol-2-ylpropyl]amino}carbonyl)-8-(benzoylamino)-8-methyl-4-oxo-4,6,7,8-tetrahydropyrrolo[1,2-a]pyrimidin-3-yl[3-(trifluoromethyl)benzyl]carbamate (12i)

To a solution of amine 12h (7.0 mg, 0.0095 mmol) in 2 mL $CH_2Cl_2$, was added benzoyl chloride (2.2 μL, 0.019 mmol) and triethylamine (2.6 μL, 0.019 mmol). The mixture was stirred at rt for 14 h, then was diluted with EtOAc. The organic solution was washed with 1N HCl, $H_2O$, and brine, dried ($Na_2SO_4$), and concentrated. The crude residue was purified by flash chromatography (60% EtOAc/hexanes) to afford 5.1 mg (64%) of benzamide (12i) as a colorless solid. MS (ESI) 840.7 (M+$H^+$), 862.7 (M+$Na^+$), 838.6 (M–$H^+$).

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-4-oxo-8-[(phenylacetyl)amino]-3-{[3-(trifluoromethyl)benzyl]amino}-4,6,7,8-tetrahydropyrrolo[1,2-a]pyrimidine-6-carboxamide (Example 12)

To a solution of 12i (5.1 mg, 0.0061 mmol) in 1 mL EtOAc, was added 10% Pd-C (5 mg). The mixture was evacuated and flushed with $H_2$ (3×), then stirred under an atmosphere of $H_2$ for 5h. The reaction was filtered and concentrated. The crude product was purified by preparative HPLC (gradient, 50 to 100% $CH_3CN/H_2O$+0.1% TFA) to afford 2.4 mg (48%) of Example 12 as the TFA salt. MS (ESI) 706.7 (M+$H^+$), 728.7 (M+$Na^+$), 600.5 (M–$H^+$); MS (HR-ESI) calculated for $C_{37}H_{44}BF_3N_5O_5$ (M+$H^+$), found 706.3386.

Example 13

(6S,8R)-N-{(1R)-1-[(3aS,4S,6S,7aR)-Hexahydro-3a,5,5-trimethyl-4,6-methano-1,3,2-benzodioxaborol-2-ylpropyl]}-8-amino-8-methyl-4-oxo-8-[(phenylacetyl)amino]-3-{[3-(trifluoromethyl)benzyl]amino}-4,6,7,8-tetrahydropyrrolo[1,2-a]pyrimidine-6-carboxamide (6S,8R)-N-{(1R)-1-[(3aS,4S,6S 7aR)-hexahydro-3a,5,5-trimethyl-4,6-methano-1,3,2-benzodioxaborol-2-ylpropyl]}-8-amino-8-methyl-4-oxo-3-{[3-(trifluoromethyl)benzyl]amino}-4,6,7,8-tetrahydropyrrolo[1,2-a]pyrimidine-6-carboxamide (13a)

To a solution of 12g (564 mg, 0.741 mmol) in 10 mL MeOH, was added 10% Pd/C (80 mg). The mixture was evacuated and flushed with $H_2$ (3×), then stirred under an atmosphere of $H_2$ for 8 h. The mixture was filtered and concentrated to afford 430 mg (97%) of the diamine (13a). MS (ESI) 602.5 (M+$H^+$), 624.5 (M+$Na^+$), 600.5 (M–$H^+$), 620.5 (M+$OH^-$).

To a solution of diamine 13a (10.0 mg, 0.0166 mmol) in 1 mL $CH_2Cl_2$, was added phenylacetyl chloride (2.4 μL, 0.018 mmol) and DMAP (2.4 mg, 0.020 mmol). The mixture was stirred at rt for 6 h, then concentrated. The crude product was purified by preparative HPLC (gradient, 50 to 100% $CH_3CN/H_2O$+0.1% TFA) to afford 6.5 mg (47%) of Example 13 as the TFA salt. MS (ESI) 720.8 (M+$H^+$) 742.7 (M+$Na^+$); 718.7 (M–$H^+$); MS (HR-ESI) calculated for $C_{38}H_{46}BF_3N_5O_5$ (M+$H^+$), found 720.3554.

Example 14

Phenyl (6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-ylcarbamate According to the procedure for the preparation of Example 13, 13a (10 mg, 0.0166 mmol) and phenyl chloroformate (2.3 μL, 0.018 mmol) afforded 3.2 mg (23%) of Example 14 as the TFA salt. MS (ESI) 722.7 (M+$H^+$) 744.7 (M+$Na^+$); 720.7 (M–$H^+$); MS (HR-ESI) calculated for $C_{37}H_{44}BF_3N_5O_6$ (M+$H^+$), found 722.3365.

Example 15

N-((6S,8R)-6-[({(1R)-1-[(3aS,4S,6S,7aR)-Hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)-2-phenyl-4-quinolinecarboxamide To a solution of 13a (10.0 mg, 0.0166 mmol) and 2-phenyl-4-quinolinecarboxylic acid (4.6 mg, 0.018 mmol) in 1:1 THF/$CH_2Cl_2$ (1 mL) and 200 μL DMF, was added TEA (2.8 μL, 0.020 mmol) and HAtU (7.6 mg, 0.020 mmol). The mixture was stirred at rt for 2 h, then was diluted with EtOAc. The organic phase was washed with $H_2O$, $NaHCO_3$, and brine, dried ($Na_2SO_4$), and concentrated. The crude product was purified by flash chromatography (55% EtOAc/hexanes), followed by preparative HPLC (gradient, 50 to 100% $CH_3CN/H_2O$+0.1% TFA) to afford 5.6 mg (32%) of Example 15 as the diTFA salt. MS (ESI) 833.6 (M+$H^+$) 855.6 (M+$Na^+$); 831.6 (M–$H^+$); MS (HR-ESI) calculated for $C_{46}H_{49}BF_3N_6O_5$ (M+$H^+$), found 833.3828.

Example 16

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(anilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide To a solution of 13a (10.0 mg, 0.0166 mmol) in 1 mL $CH_2Cl_2$, was added phenyl isocyanate (2.0 mg, 0.017 mmol). The mixture was stirred as rt for 30 min, then concentrated. Purification by preparative HPLC (gradient, 50–100% $CH_3CN/H_2O+0.1\%$ TFA) afforded 5.6 mg (40%) of Example 16 as the TFA salt. LC-MS (ESI) 721.24 (M+H$^+$).

Example 17

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(benzoylamino)carbonyl]amino}-8-methyl-4-oxo-3-{[3-(trifluoromethyl)benzyl] amino}-4,6,7,8-tetrahydropyrrolo[1,2-a]pyrimidine-6-carboxamide According to the procedure for the preparation of Example 16, 13a (8.0 mg, 0.0105 mmol) and benzoyl isocyanate (1.5 mg, 0.0105 mmol) afforded 5.8 mg (64%) of Example 17 as the TFA salt. MS (HR-ESI) calculated for $C_{38}H_{45}BF_3N_{6I\ O6}$ (M+H$^+$), found 749.3461.

Example 18

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(4-methoxyanilino)carbonyl]amino}-8-methyl-4-oxo-3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and 4-methoxyphenyl isocyanate (2.5 mg, 0.017 mmol) afforded 5.3 mg (37%) of Example 18 as the TFA salt. LC-MS (ESI) 751.26 (M+H$^+$).

Example 19

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(2-fluoroanilino)carbonyl]amino}-8-methyl-4-oxo-3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and 2-fluorophenyl isocyanate (2.3 mg, 0.017 mmol) afforded 5.5 mg (39%) of Example 19 as the TFA salt. LC-MS (ESI) 739.25 (M+H$^+$).

Example 20

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(3-methoxyanilino)carbonyl]amino}-8-methyl-4-oxo-3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and 3-methoxyphenyl isocyanate (2.5 mg, 0.017 mmol) afforded 6.0 mg (42%) of Example 20 as the TFA salt. LC-MS (ESI) 751.25 (M+H$^+$).

Example 21

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-{[(1-naphthylamino) carbonyl]amino}-4-oxo-3-{[3-(trifluoromethyl) benzyl]amino}-4,6,7,8-tetrahydropyrrolo[1,2-a] pyrimidine-6-carboxamide According to the procedure for the preparation of Example 16, 13a (10.0 mg, 0.0166 mmol) and 1-naphthyl isocyanate (2.8 mg, 0.017 mmol) afforded 6.0 mg (41%) of Example 21 as the TFA salt. LC-MS (ESI) 771.29 (M+H$^+$).

Example 22

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(3-cyanoanilino)carbonyl]amino}-8-methyl-4-oxo-3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and 3-cyanophenyl isocyanate (2.4 mg, 0.017 mmol) afforded 6.6 mg (46%) of Example 22 as the TFA salt. LC-MS (ESI) 746.27 (M+H$^+$).

Example 23

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(3-acetylanilino)carbonyl]amino}-8-methyl-4-oxo-3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and 3-acetylphenyl isocyanate (2.7 mg, 0.017 mmol) afforded 6.2 mg (43%) of Example 23 as the TFA salt. LC-MS (ESI) 763.28 (M+H$^+$).

Example 24

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-{[(4-phenoxyanilino) carbonyl]amino}3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and 4-phenoxyphenyl isocyanate (3.5 mg, 0.017 mmol) afforded 6.8 mg (44%) of Example 24 as the TFA salt. LC-MS (ESI) 813.31 (M+H$^+$).

Example 25

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(4-acetylanilino)carbonyl]amino}-8-methyl-4-oxo-3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and 4-acetylphenyl isocyanate (2.7 mg, 0.017 mmol) afforded 6.5 mg (45%) of Example 25 as the TFA salt. LC-MS (ESI) 763.28 (M+H$^+$).

Example 26

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-{[(2-naphthylamino) carbonyl]amino}-4-oxo-3-{[3-(trifluoromethyl) benzyl]amino}-4,6,7,8-tetrahydropyrrolo[1,2-a] pyrimidine-6-carboxamide According to the procedure for the preparation of Example 16, 13a (10.0 mg, 0.0166 mmol) and 2-naphthyl isocyanate (2.8 mg, 0.017 mmol) afforded 5.3 mg (36%) of Example 26 as the TFA salt. LC-MS (ESI) 771.28 (M+H⁺).

Example 27

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-4-oxo-8-{[((trans-2-phenylcyclopropyl)amino)carbonyl]amino}-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and trans-2-phenylcyclopropyl isocyanate (2.6 mg, 0.017 mmol) afforded 4.4 mg (30%) of Example 27 as the TFA salt. LC-MS (ESI) 761.22 (M+H⁺).

Example 28

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(2,4-difluoroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2,4-difluorophenyl isocyanate (2.6 mg, 0.017 mmol) afforded 5.4 mg (37%) of Example 28 as the TFA salt. LC-MS (ESI) 757.19 (M+H⁺).

Example 29

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(2,5-difluoroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2,5-difluorophenyl isocyanate (2.6 mg, 0.017 mmol) afforded 6.2 mg (43%) of Example 29 as the TFA salt. LC-MS (ESI) 757.20 (M+H⁺).

Example 30

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(2-methoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2-methoxyphenyl isocyanate (2.5 mg, 0.017 mmol) afforded 4.4 mg (31%) of Example 30 as the TFA salt. LC-MS (ESI) 751.25 (M+H⁺).

Example 31

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-4-oxo-8-{[(2-(trifluoromethyl)anilino)carbonyl]amino}-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2-(trifluoromethyl)phenyl isocyanate (3.1 mg, 0.017 mmol) afforded 5.5 mg (37%) of Example 31 as the TFA salt. LC-MS (ESI) 789.24 (M+H⁺).

Example 32

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(3-fluoroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 3-fluorophenyl isocyanate (2.3 mg, 0.017 mmol) afforded 6.8 mg (48%) of Example 32 as the TFA salt. LC-MS (ESI) 739.25 (M+H⁺).

Example 33

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-4-oxo-8-{[(3-(trifluoromethyl)anilino)carbonyl]amino}-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 3-(trifluoromethyl)phenyl isocyanate (3.1 mg, 0.017 mmol) afforded 6.9 mg (46%) of Example 33 as the TFA salt. LC-MS (ESI) 789.25 (M+H⁺).

Example 34

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(4-fluoroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-fluorophenyl isocyanate (2.3 mg, 0.017 mmol) afforded 5.3 mg (37%) of Example 34 as the TFA salt. LC-MS (ESI) 739.26 (M+H⁺).

Example 35

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-4-oxo-8-{[(4-(trifluoromethyl)anilino)carbonyl]amino}-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-(trifluoromethyl)phenyl isocyanate (3.1 mg, 0.017 mmol) afforded 6.4 mg (43%) of Example 35 as the TFA salt. LC-MS (ESI) 789.26 (M+H⁺).

Example 36

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-8-{[(4-methylanilino)carbonyl]amino}-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and p-tolyl isocyanate (2.2 mg, 0.017 mmol) afforded 5.3 mg (38%) of Example 36 as the TFA salt. LC-MS (ESI) 735.29 (M+H⁺).

Example 37

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(2,6-diisopropylanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2,6-diisopropylphenyl isocyanate (3.4 mg, 0.017 mmol) afforded 4.9 mg (32%) of Example 37 as the TFA salt. LC-MS (ESI) 805.37 (M+H⁺).

Example 38

Methyl 2-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate According to the procedure for the preparation of Example 16, 13a (10.0 mg, 0.0166 mmol) and methyl 2-isocyanatobenzoate (2.9 mg, 0.017 mmol) afforded 4.9 mg (33%) of Example 38 as the TFA salt. LC-MS (ESI) 779.28 (M+H⁺).

Example 39

Ethyl 2-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate According to the procedure for the preparation of Example 16, 13a (10.0 mg, 0.0166 mmol) and ethyl 2-isocyanatobenzoate (3.2 mg, 0.017 mmol) afforded 4.2 mg (28%) of Example 39 as the TFA salt. LC-MS (ESI) 793.30 (M +H⁺).

Example 40

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(2-isopropylanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2-isopropylphenyl isocyanate (2.7 mg, 0.017 mmol) afforded 4.9 mg (34%) of Example 40 as the TFA salt. LC-MS (ESI) 763.32 (M+H⁺).

Example 41

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-3-{[3-(trifluoromethyl)benzyl]amino}-8-{[(3,4,5-trimethoxyanilino)carbonyl]amino}-4,6,7,8-tetrahydropyrrolo[1,2-a]pyrimidine-6-carboxamide According to the procedure for the preparation of Example 16, 13a (10.0 mg, 0.0166 mmol) and 3,4,5-trimethoxyphenyl isocyanate (3.5 mg, 0.017 mmol) afforded 3.7 mg (24%) of Example 41 as the TFA salt. LC-MS (ESI) 811.31 (M+H⁺).

Example 42

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-{[(3-(methylthio)anilino)carbonyl]amino}-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 3-(methylthio)phenyl isocyanate (2.7 mg, 0.017 mmol) afforded 4.8 mg (33%) of Example 42 as the TFA salt. LC-MS (ESI) 767.25 (M+H⁺).

Example 43

Ethyl 3-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate According to the procedure for the preparation of Example 16, 13a (10.0 mg, 0.0166 mmol) and ethyl 3-isocyanatobenzoate (3.2 mg, 0.017 mmol) afforded 6.1 mg (41%) of Example 43 as the TFA salt. LC-MS (ESI) 793.29 (M+H⁺).

Example 44

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(4-ethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-ethoxyphenyl isocyanate (2.7 mg, 0.017 mmol) afforded 4.2 mg (29%) of Example 44 as the TFA salt. LC-MS (ESI) 765.29 (M+H⁺).

Example 45

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-{[(4-(methylthio)anilino)carbonyl]amino}-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-(methylthio)phenyl isocyanate (2.7 mg, 0.017 mmol) afforded 5.7 mg (39%) of Example 45 as the TFA salt. LC-MS (ESI) 767.26 (M+H⁺).

Example 46

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(4-isopropylanilino)carbonyl]amino}-8-methyl-4-oxo-3-{[3-(trifluoromethyl)benzyl]amino}-4,6,7,8-tetrahydropyrrolo [1,2-a]pyrimidine-6-carboxamide According to the procedure for the preparation of Example 16, 13a (10.0 mg, 0.0166 mmol) and 4-isopropylphenyl isocyanate (2.7 mg, 0.017 mmol) afforded 4.3 mg (30%) of Example 46 as the TFA salt. LC-MS (ESI) 763.32 (M+H+).

Example 47

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(4-ethylanilino)carbonyl]amino}-8-methyl-4-oxo-3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and 4-ethylphenyl isocyanate (2.4 mg, 0.017 mmol) afforded 5.7 mg (40%) of Example 47 as the TFA salt. LC-MS (ESI) 749.30 (M+H+).

Example 48

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-{[(4-(trifluoromethoxy)anilino)carbonyl]amino}-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-(trifluoromethoxy)phenyl isocyanate (3.4 mg, 0.017 mmol) afforded 6.6 mg (43%) of Example 48 as the TFA salt. LC-MS (ESI) 805.25 (M+H+).

Example 49

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-({[(2-phenylethyl) amino]carbonyl}amino)-3-{[3-(trifluoromethyl) benzyl]amino}-4,6,7,8-tetrahydropyrrolo[1,2-a] pyrimidine-6-carboxamide According to the procedure for the preparation of Example 16, 13a (10.0 mg, 0.0166 mmol) and phenethyl isocyanate (2.4 mg, 0.017 mmol) afforded 4.6 mg (32%) of Example 49 as the TFA salt. LC-MS (ESI) 749.30 (M+H+).

Example 50

Methyl 3-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl] amino}-4,6,7,8-tetrahydropyrrolo[1,2-a]pyrimidin-8-yl)amino]carbonyl}amino)benzoate According to the procedure for the preparation of Example 16, 13a (10.0 mg, 0.0166 mmol) and methyl 3-isocyanatobenzoate (2.9 mg, 0.017 mmol) afforded 6.2 mg (42%) of Example 50 as the TFA salt. LC-MS (ESI) 779.26 (M+H+).

Example 51

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[([1,1'-biphenyl]-2-ylamino)carbonyl] amino}-8-methyl-4-oxo-3-{[3-(trifluoromethyl) benzyl]amino}-4,6,7,8-tetrahydropyrrolo[1,2-a] pyrimidine-6-carboxamide According to the procedure for the preparation of Example 16, 13a (10.0 mg, 0.0166 mmol) and 2-biphenyl isocyanate (3.2 mg, 0.017 mmol) afforded 5.1 mg (34%) of Example 51 as the TFA salt. LC-MS (ESI) 797.30 (M+H+).

Example 52

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-3-{[3-(trifluoromethyl) benzyl]amino}-8-{[(tritylamino)carbonyl]amino}-4, 6,7,8-tetrahydropyrrolo[1,2-a]pyrimidine-6-carboxamide According to the procedure for the preparation of Example 16, 13a (10.0 mg, 0.0166 mmol) and triphenylmethyl isocyanate (4.7 mg, 0.017 mmol) afforded 6.6 mg (40%) of Example 52 as the TFA salt. LC-MS (ESI) 887.35 (M+H+).

Example 53

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-[({[(1R)-1-(1-naphthyl)ethyl] amino}carbonyl)amino]-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and (R)-(−)-1-naphthyl)ethyl isocyanate (3.3 mg, 0.017 mmol) afforded 3.8 mg (25%) of Example 53 as the TFA salt. LC-MS (ESI) 799.31 (M+H+).

Example 54

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-[({[(1)-1-(1-phenyl) ethyl]amino}carbonyl)amino]-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and (S)-(−)-1-phenylethyl isocyanate (2.4 mg, 0.017 mmol) afforded 3.8 mg (27%) of Example 54 as the TFA salt. LC-MS (ESI) 749.30 (M+H+).

Example 55

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(isopropylamino)carbonyl]amino}-8-methyl-4-oxo-3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and isopropyl isocyanate (1.4 mg, 0.017 mmol) afforded 4.1 mg (31%) of Example 55 as the TFA salt. LC-MS (ESI) 687.29 (M+H+).

Example 56

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-{[(2-phenoxyanilino) carbonyl]amino}-3-{[3-(trifluoromethyl)benzyl] amino}-4,6,7,8-tetrahydropyrrolo[1,2-a]pyrimidine-6-carboxamide According to the procedure for the preparation of Example 16, 13a (10.0 mg, 0.0166 mmol) and

Example 57

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(2,6-difluoroanilino)carbonyl]amino}8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2,6-difluorophenyl isocyanate (2.6 mg, 0.017 mmol) afforded 6.1 mg (42%) of Example 57 as the TFA salt. LC-MS (ESI) 757.24 (M+H$^+$).

Example 58

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-[({[(1R)-1-(1-phenyl)ethyl]amino}carbonyl)amino]-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and (R)-(+)-1-phenylethyl isocyanate (2.4 mg, 0.017 mmol) afforded 4.8 mg (34%) of Example 58 as the TFA salt. LC-MS (ESI) 749.29 (M+H$^+$).

Example 59

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(4-isopropylanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-isopropylphenyl isocyanate (2.7 mg, 0.017 mmol) afforded 5.8 mg (40%) of Example 59 as the TFA salt. LC-MS (ESI) 763.30 (M+H$^+$).

Example 60

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-({[4-(dimethylamino)anilino]carbonyl}amino)-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-(dimethylamino)phenyl isocyanate (2.7 mg, 0.017 mmol) afforded 9.8 mg (60%) of Example 60 as the TFA salt. LC-MS (ESI) 764.30 (M+H$^+$).

Example 61

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(3,4-dichloroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 3,4-dichlorophenyl isocyanate (3.1 mg, 0.017 mmol) afforded 5.1 mg (34%) of Example 61 as the TFA salt. LC-MS (ESI) 789.18 (M+H$^+$).

Example 62

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(4-tert-butylanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-tert-butylphenyl isocyanate (2.9 mg, 0.017 mmol) afforded 6.1 mg (41%) of Example 62 as the TFA salt. LC-MS (ESI) 777.31 (M+H$^+$).

Example 63

Methyl 2-({[(((6S,8R)-6-[({(1R)-1-[(3aS,4S,6S,7aR)-Hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)-3-methylbutanoate According to the procedure for the preparation of Example 16, 13a (10.0 mg, 0.0166 mmol) and (S)-(–)-2-isocyanato-3-methylbutyric acid methyl ester (2.6 mg, 0.017 mmol) afforded 5.2 mg (36%) of Example 63 as the TFA salt. LC-MS (ESI) 759.29 (M+H$^+$).

Example 64

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(benzylamino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and benzyl isocyanate (2.2 mg, 0.017 mmol) afforded 9.0 mg (64%) of Example 64 as the TFA salt. MS (ESI) 735.3 (M+H$^+$), 757.4 (M+Na$^+$); 733.3 (M–H$^+$).

Example 65

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-({[(4-chlorobenzoyl)amino]carbonyl}amino)-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and p-chlorobenzoyl isocyanate (3.0 mg, 0.017 mmol) afforded 7.0 mg (47%) of Example 65 as the TFA salt. MS (ESI) 783.5 (M+H$^+$) 805.7 (M+Na$^+$); 781.7 (M–H$^+$).

Example 66 tert-Butyl 2-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate According to the procedure for the preparation of Example 16, 13a (10.0 mg, 0.0166 mmol) and t-butyl 2-isocyanatobenzoate (0.017 mmol) afforded 3.0 mg (22%) of Example 66. MS (ESI) 821.9 (M+H$^+$) 843.8 (M+Na$^+$); 819.7 (M−H$^+$), 839.7 (M+F$^-$).

Example 67

2-({[(((6S,8R)-6-[({(1R)-1-[(3aS,4S,6S,7aR)-Hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoic acid A solution of Example 66 (1.9 mg, 0.0023 mmol) and 4N HCl/dioxane (1 mL), was stirred for 6.5 h, then concentrated. The crude residue was purified by preparative HPLC (gradient, 50 to 100% CH$_3$CN/H$_2$O+0.1% TFA) to afford 1.1 mg (54%) of Example 67 as the TFA salt. MS (ESI) 765.7 (M+H$^+$) 787.7 (M+Na$^+$); 763.7 (M−H$^+$).

Example 68

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(2-chloroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2-chlorophenyl isocyanate (0.017 mmol) afforded 9.1 mg (63%) of Example 68 as the TFA salt. MS (HR-ESI) calculated for C$_{37}$H$_{44}$BClF$_3$N$_6$O$_5$ (M+H$^+$), found 755.3137.

Example 69

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(2,5-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2,5-dimethoxyphenyl isocyanate (0.017 mmol) afforded 8.9 mg (60%) of Example 69 as the TFA salt. MS (HR-ESI) calculated for C$_{39}$H$_{49}$BF$_3$N$_6$O$_7$ (M+H$^+$), found 781.3710.

Example 70

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-4-oxo-8-[(2-toluidinocarbonyl)amino]-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and o-tolyl isocyanate (0.017 mmol) afforded 8.4 mg (60%) of Example 70 as the TFA salt. MS (HR-ESI) calculated for C$_{38}$H$_{47}$BF$_3$N$_6$O$_5$ (M+H$^+$), found 735.3673.

Example 71

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(5-chloro-2,4-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 5-chloro-2,4-dimethoxyphenyl isocyanate (0.017 mmol) afforded 9.4 mg (61%) of Example 71 as the TFA salt. MS (HR-ESI) calculated for C$_{39}$H$_{48}$BClF$_3$N$_6$O$_7$ (M+H$^+$), found 815.3341.

Example 72

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(2,4-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2,4-dimethoxyphenyl isocyanate (0.017 mmol) afforded 9.0 mg (61%) of Example 72 as the TFA salt. MS (HR-ESI) calculated for C$_{39}$H$_{49}$BF$_3$N$_6$O$_7$ (M+H$^+$), found 781.3717.

Example 73

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(2-ethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2-ethoxyphenyl isocyanate (0.017 mmol) afforded 9.1 mg (62%) of Example 73 as the TFA salt. MS (HR-ESI) calculated for C$_{39}$H$_{49}$BF$_3$N$_6$O$_6$ (M+H$^+$), found 765.3788.

Example 74

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(5-chloro-2-methoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 5-chloro-2-methoxyphenyl isocyanate (0.017 mmol) afforded 8.2 mg (55%) of Example 74 as the TFA salt. MS (HR-ESI) calculated for C$_{38}$H$_{46}$BClF$_3$N$_6$O$_6$ (M+H$^+$), found 785.3208.

Example 75

Butyl 2-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate According to the procedure for the preparation of Example 16, 13a (10.0 mg, 0.0166 mmol) and butyl isocyanaotbenzoate (0.017 mmol) afforded 8.5 mg (55%) of Example 75 as the TFA salt. MS (HR-ESI) calculated for C$_{42}$H$_{53}$BF$_3$N$_6$O$_7$ (M+H$^+$), found 821.4049.

Example 76

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-8-({[(2-methylthio)anilino]carbonyl}amino)-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2-(thiomethyl)phenyl isocyanate (0.017 mmol) afforded 8.7 mg (60%) of Example 76 as the TFA salt. MS (HR-ESI) calculated for $C_{38}H_{47}ESF_3N_6O_5$ (M+H$^+$), found 815.3341.

Example 77

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(4-chloroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-chlorophenyl isocyanate (0.017 mmol) afforded 8.4 mg (58%) of Example 77 as the TFA salt. MS (HR-ESI) calculated for $C_{37}H_{44}BClF_3N_6O_5$ (M+H$^+$), found 755.3106.

Example 78

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-{[(4-fluoro-2nitroanilino)carbonyl]amino}-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 4-fluoro-2-nitrophenyl isocyanate (0.017 mmol) afforded 6.3 mg (55%) of Example 78 as the TFA salt. MS (HR-ESI) calculated for $C_{37}H_{43}BF_4N_7O_7$ (M+H$^+$), found 784.3261.

Example 79

Dimethyl 5-({[(((6S,8R)-6-[({(1R)-1-[(3aS,4S,6S, 7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)isophthalate According to the procedure for the preparation of Example 16, 13a (10.0 mg, 0.0166 mmol) and dimethyl 5-isocyanatoisophthalate (0.017 mmol) afforded 6.7 mg (42%) of Example 79 as the TFA salt. MS (HR-ESI) calculated for $C_{41}H_{49}BF_3N_6O_9$ (M+H$^+$), found 837.3601.

Example 80

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-3-{[3-(trifluoromethyl)benzyl]amino}-8-[({3-(trifluoromethyl)sulfanyl]anilino}carbonyl)amino]-4,6,7,8-tetrahydropyrrolo[1,2-a]pyrimidine-6-carboxamide According to the procedure for the preparation of Example 16, 13a (10.0 mg, 0.0166 mmol) and 3-(thiotrifluoromethyl)phenyl isocyanate (0.017 mmol) afforded 9.4 mg (61%) of Example 80 as the TFA salt. MS (HR-ESI) calculated for $C_{38}H_{44}BF_6N_6O_5S$ (M+H$^+$), found 821.3110.

Example 81

Ethyl 4-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate According to the procedure for the preparation of Example 16, 13a (10.0 mg, 0.0166 mmol) and ethyl 4-isocyanatobenzoate (0.017 mmol) afforded 8.9 mg (59%) of Example 81 as the TFA salt. MS (HR-ESI) calculated for $C_{40}H_{49}BF_3N_6O_7$ (M+H$^+$), found 793.3718.

Example 82

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-{[(2-nitroanilino)carbonyl]amino}-4-oxo-3-{[3-(trifluoromethyl)benzyl]amino}-4,6,7,8-tetrahydropyrrolo[1,2-a]pyrimidine-6-carboxamide According to the procedure for the preparation of Example 16, 13a (10.0 mg, 0.0166 mmol) and 2-nitrophenyl isocyanate (0.017 mmol) afforded 8.8 mg (60%) of Example 82 as the TFA salt. MS (HR-ESI) calculated for $C_{37}H_{44}BF_3N_7O_7$ (M+H$^+$), found 766.3362.

Example 83

(6S,8R)-N-{(1R)-1-[(3aS,4S,6S,7aR)-Hexahydro-3a, 5,5-trimethyl-4,6-methano-1,3,2-benzodioxaborol-2-yl]propyl}-8-{[(2-aminoanilino)carbonyl]amino}-8-methyl-4-oxo-3-{[3-(trifluoromethyl)benzyl]amino)-4,6,7,8-tetrahydropyrrolo[1,2-a]pyrimidine-6-carboxamide To a solution of Example 82 (4.0 mg, 0.0052 mmol) in 1 mL MeOH, was added 5 mg 10% Pd-C. The mixture was evacuated and flushed with $H_2$ (3×), then stirred under an atmosphere of $H_2$ for 15 min. The mixture was filtered and concentrated to afford 3.8 mg (98%) of Example 83 as the TFA salt. MS (ESI) 736.5 (M+H$^+$) 758.5 (M+Na$^+$); 734.4 (M–H$^+$).

Example 84

N—((6S,8R)-6-[({(1RS)-1-[(3aS,4S,6S,7aR)-Hexahydro-3a,5,5-trimethyl-4,6-methano-1,3,2-benzodioxaborol-2-yl]-3,3-difluropropyl}amino)carbonyl]-8-methyl-4-oxo-3-{[3-(trifluoromethyl)benzyl]amino}-4,6,7,8-tetrahydropyrrolo[1,2-a]pyrimidin-8-yl)-2-phenyl-4-quinolinecarboxamide Benzyl (6S,8R)-6-[({1-[(3aS,4S,6S,7aR)-hexahydro-3a,5,5-trimethyl-4,6-methano-1,3,2-benzodioxaborol-2-yl]-3,3-difluoropropyl}amino)carbonyl]-8-azido-8-methyl-4-oxo-4,6,7,8-tetrahydropyrrolo[1,2-a]pyrimidin-3-yl[3-(trifluoromethyl)benzyl]carbamate (84a)

To a solution of 12f (0.471 mmol) and the diF-Eta-boropinacol (170 mg, 0.660 mmol) in 4:1 $CH_2Cl_2$ (6 mL) at 0° C., were added HOAt (71 mg, 0.518 mmol), NaHCO$_3$ (99 mg, 1.18 mmol), and EDCI (127 mg, 0.660 mmol).; The mixture was allowed to warm to rt and stir for 3 h. Pinane diol (160 mg, 0.942 mmol) was added and the mixture was stirred for 1 h. The mixture was diluted with EtOAc. The organic phase was washed with 1N HCl, $H_2O$, sat. NaHCO$_3$, $H_2O$, and brine, dried (Na$_2$SO$_4$), and concentrated. The crude material was purified by flash chromatography (35% EtOAc/hexanes), followed by size-exclusion chromatography (Sephadex LH-20, MeOH) to afford 141 mg (38% from the imide 12e) of 84a as a colorless residue. MS (ESI) 820.6 (M+Na$^+$).

(6S,8R)-N-{1-[(3aS,4S,6S,7aR)-hexahydro-3a,5,5-trimethyl-4,6-methano-1,3,2-benzodioxaborol-2-yl]-3,3-difluoropropyl}-8-amino-8-methyl-4-oxo-3-{[3-(trifluoromethyl)benzyl]amino}-4,6,7,8-tetrahydropyrrolo[1,2-a]pyrimidine-6-carboxamide (84b)

To a solution of 84a (141 mg, 0.177 mmol) in 5 mL MeOH, was added 10% Pd-C (50 mg). The mixture was evacuate and flushed with $H_2$ (3×), then was stirred under an atmosphere of $H_2$ for 8 h. The mixture was filtered and concentrated to give 113 mg (quantitative) of 84b. MS (ESI) 638.4 (M+H$^+$), 660.3 (M+Na$^+$), 636.3 (M–H$^+$).

To a solution of 84b (10.0 mg, 0.0157 mmol) and 2-phenyl-4-quinolinecarboxylic acid (4.3 mg, 0.017 mmol) in $CH_2Cl_2$ (0.5 mL) and 100 µL DMF, was added TEA (2.6

L, 0.019 mmol) and HAtU (7.1 mg, 0.019 mmol). The mixture was stirred at rt for 16 h, concentrated. Purification by preparative HPLC (gradient, 50 to 100% $CH_3CN/H_2O$+ 0.1% TFA) afforded 6.7 mg (39%) of Example 84 as the bis TFA salt. MS (ESI) 869.8 (M+H$^+$) 891.8 (M+Na$^+$).

Example 85

(6S,8R)-N-{(1RS)-1-[(3aS,4S,6S,7aR)-Hexahydro-3a,5,5-trimethyl-4,6-methano-1,3,2-benzodioxaborol-2-yl]-3,3-difluoropropyl}-8-{[(2,5-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide To a solution of 84b (10.0 mg, 0.0157 mmol) in $CH_2Cl_2$ (0.5 mL), was added 2,5-dimethyoxyphenyl isocyanate (0.016 mmol). The mixture was stirred at rt for 15 h, then concentrated. Purification by preparative HPLC (gradient, 50 to 100% $CH_3CN/H_2O$+0.1% TFA) afforded 4.0 mg (27%) of Example 85 as the TFA salt. MS (HR-ESI) calculated for $C_{39}H_{47}BF_5N_6O_7$ (M+H$^+$), found 817.3539.

Example 86

(6S,8R)-N-{(1RS)-1-[(3aS,4S,6S,7aR)-Hexahydro-3a,5,5-trimethyl-4,6-methano-1,3,2-benzodioxaborol-2-yl]-3,3-difluoropropyl}-8-{[(5-chloro-2,4-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 85, 84b (10.0 mg, 0.0157 mmol) and 5-chloro-2,4-dimethoxyphenyl isocyanate (0.016 mmol) afforded 5.4 mg (36%) of Example 86 as the TFA salt. MS (HR-ESI) calculated for $C_{39}H_{46}BClF_5N_6O_7$ (M+H$^+$), found 851.3153.

Example 87

Methyl 2-({[(((6S,8R)-6-[({(1RS)-1-[(3aS,4S,6S,7aR)-hexahydro-3a,5,5-trimethyl-4,6-methano-1,3,2-benzodioxaborol-2-yl]-3,3-difluoropropyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate According to the procedure for the preparation of Example 85, 84b (10.0 mg, 0.0157 mmol) and methyl 2-isocyanatobenzoate (0.016 mmol) afforded 4.9 mg (34%) of Example 87 as the TFA salt. MS (HR-ESI) calculated for $C_{39}H_{45}BF_5N_6O_7$ (M+H$^+$), found 815.3370.

Example 88

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-8-({[2-(methylthionyl)anilino]carbonyl}amino)-4-oxo-3-{[3-(trifluoromethyl)benzyl]amino}-4,6,7,8-tetrahydropyrrolo[1,2-a]pyrimidine-6-carboxamide According to the procedure for the preparation of Example 85, 84b (10.0 mg, 0.0157 mmol) and 2-(methylthio)phenyl isocyanate (0.016 mmol) afforded 5.3 mg (37%) of Example 88 as the TFA salt. MS (HR-ESI) calculated for $C_{38}H_{45}BF_5N_6O_5S$ (M+H$^+$), found 803.3181.

Example 89

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(2-ethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 85, 84b (10.0 mg, 0.0157 mmol) and 2-ethoxyphenyl isocyanate (0.016 mmol) afforded 4.6 mg (32%) of Example 89 as the TFA salt. MS (HR-ESI) calculated for $C_{39}H_{47}BF_5N_6O_6$ (M+H$^+$), found 801.3562.

Example 90

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-{[(5-chloro-2-methoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 85, 84b (10.0 mg, 0.0157 mmol) and 5-chloro-2-methoxyphenyl isocyanate (0.016 mmol) afforded 5.2 mg (35%) of Example 90 as the TFA salt. MS (HR-ESI) calculated for $C_{38}H_{44}BClF_5N_6O_6$ (M+H$^+$), found 821.3013.

Example 91

Ethyl 2-({[(((6S,8R)-6-[({(1RS)-1-[3aS,4S,6S,7aR)-hexahydro-3a,5,5-trimethyl-4,6-methano-1,3,2-benzodioxaborol-2-yl]-3,3-difluoropropyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate According to the procedure for the preparation of Example 85, 84b (10.0 mg, 0.0157 mmol) and ethyl 2-isocyanatobenzoate (0.016 mmol) afforded 4.8 mg (32%) of Example 91 as the TFA salt. MS (HR-ESI) calculated for $C_{40}H_{47}BF_5N_6O_7$ (M+H$^+$), found 829.3534.

Example 92 tert-Butyl ((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetate

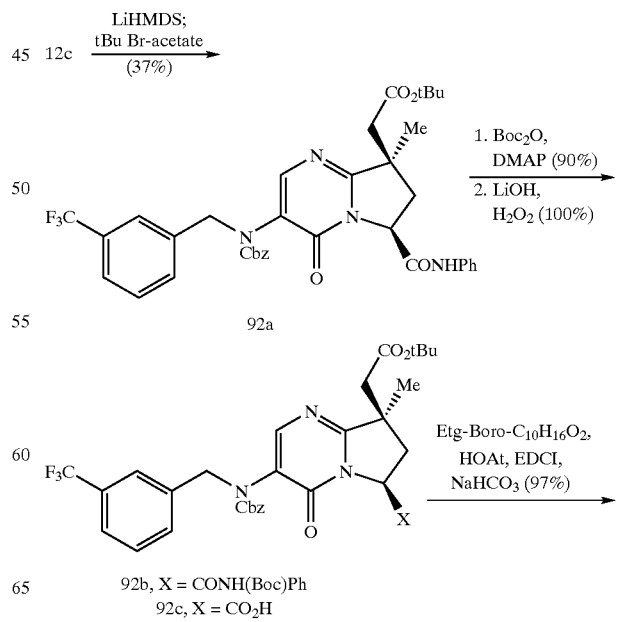

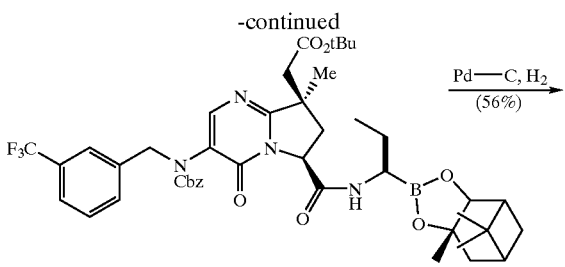

92d

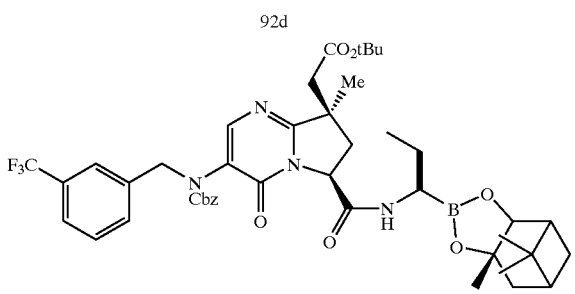

Example 92 tert-Butyl ((6S,8R)-6-(anilinocarbonyl)-8-methyl-4-oxo-3-{[3-(trifluoromethyl)benzyl]amino}-4,6,7,8-tetrahydropyrrolo[1,2-a]pyrimidin-8-yl)acetate (92a)

To a solution of 12c (0.987 g, 1.71 mmol) in 8.6 mL THF at −78° C., was added LiHMDS (1M in THF, 3.59 mL, 3.59 mmol). The red solution was stirred at −78° C. for 10 min, then a solution of t-butyl bromoacetate (0.278 mL, 1.88 mmol) was added. The reaction was allowed to slowly warm to −50° C. over 1 h, then was quenched with the addition of sat. $NH_4Cl$. The mixture was poured into 50 mL $H_2O$ and extracted with 100 mL EtOAc. The organic phase was washed with 0.1N HCl and brine, dried ($Na_2SO_4$), and concentrated. The product was purified by flash chromatography (50% EtOAc/hexanes) to afford 432 mg (37%) of 92a. $^1$H NMR (300 MHz, $CDCl_3$) δ8.94 (br s, 1H), 7.51–7.26 (m, 15H), 7.09 (t, J=7.5, 1H), 5.25–5.13 (m, 3H), 5.06 (dd, J=9.4, 6.0, 1H), 4.85 (br s, 2H), 2.89 (dd, J=13.9, 5.8, 1H), 2.80 ($AB_q$, $J_{AB}$=16.8, $δv_{AB}$=91.9, 2H), 2.44 (dd, J=13.5, 9.1, 1H), 1.38 (s, 12H); MS (ESI) 713.2 (M+Na$^+$), 689.4 (M−H$^+$).

tert-Butyl((6S,8R)-6-{[(tert-butoxycarbonyl)anilino]carbonyl}-8-methyl-4-oxo-3-{[3-(trifluoromethyl)benzyl]amino}-4,6,7,8-tetrahydropyrrolo[1,2-a]pyrimidin-8-yl)acetate (92b)

To a solution of 92a (428 mg, 0.620 mmol) in 5 mL $CH_3CN$ at rt, was added DMAP (38 mg, 0.31 mmol) and $Boc_2O$ (406 mg, 1.86 mmol). The mixture was stirred at rt for 3 h, then was diluted with EtOAc. The organic phase was washed with 1N HCl, $H_2O$, and brine, dried ($Na_2SO_4$), and concentrated. The residue obtained was purified by flash chromatography (25% EtOAc/hexanes) to afford 439 mg (90%) of 92b. $^1$H NMR (300 MHz, $CDCl_3$) δ7.54–7.21 (m, 15H), 5.97 (dd, J=9.1, 5.5, 1H), 5.16 (br s, 2H), 4.84 (br s, 2H), 2.88–2.53 (m, 4H), 1.44 (s, 3H), 1.40 (s, 9H), 1.39 (s, 9H); MS (ESI) 791.7 (M+H$^+$), 813.7 (M+Na$^+$); 789.7 (M−H$^+$).

(6S,8R)-8-(2-tert-Butoxy-2-oxoethyl)-8-methyl-4-oxo-3-{[3-(trifluoromethyl)benzyl]amino}-4,6,7,8-tetrahydropyrrolo[1,2-a]pyrimidine-6-carboxylic acid (92c)

To a solution of 92b (434 mg, 0.549 mmol) in 5 mL THF/$H_2O$ (4:1) at 0° C., was added 30% $H_2O_2$ (249 □L, 2.20 mmol) and 1N LiOH (0.933 mL, 0.933 mmol). The mixture was stirred at 0° C. of 2 h, then $Na_2SO_3$ (118 mg, 0.933 mmol) in 1 mL $H_2O$ was added. The mixture was stirred 5 min, then diluted with EtOAc and acidified with 0.5N HCl. The aqueous was extracted with EtOAc (5×). The combined organic extract was washed with brine, dried ($Na_2SO_4$) and concentrated to afford 423 mg (quantitative) of a 1:1 mixture of 92c and BocNHPh, which was used in the following step with out further purification. MS (ESI) 616.5 (M+H$^+$), 638.5 (M+Na$^+$), 660.5 (M−H$^+$+2Na$^+$); 789.7 (M−H$^+$).

tert-Butyl ((6S,8R)-6-({[(1R)-1-[(3aS,4S,6S,7aR)-hexahydro-3a,5,5-trimethyl-4,6-methano-1,3,2-benzodioxaborol-2-ylpropyl]amino}carbonyl)-3-{[(benzyloxy)carbonyl][3-(trifluoromethyl)benzyl]amino}-8-methyl-4-oxo-4,6,7,8-tetrahydropyrrolo[1,2-a]pyrimidin-8-yl)acetate (92d)

To a solution of 92c (0.549 mmol) in 5:1 $CH_2Cl_2$/DMF (4 mL) at 0° C., was added HOAt (82 mg, 0.604 mmol), EDCI (116 mg, 0.604 mmol), Etg-boro-$C_{10}H_{16}O_2$ (3-12e) (180 mg, 0.659 mmol) and $NaHCO_3$ (115 mg, 1.37 mmol). The mixture was stirred with warming to rt for 3 h. The mixture was poured into half-sat. $NaHCO_3$, then extrated with EtOAc. The organic phase was washed with 0.5 N HCl and brine, dried ($Na_2SO_4$), and concentrated in vacuo. The crude reaction product was purified by flash chromatography (4% MeOH/$CH_2Cl_2$) to afford 443 mg (97%) of 92d. $^1$H NMR (300 MHz, $CDCl_3$) δ7.50–7.27 (m, 10H), 6.82 (br s, 1H), 5.17 (s, 2H), 4.92–4.88 (m, 2H), 5.68–5.61 (m, 2H), 4.27 (d, J=8.4, 1H), 3.20 (q, J=6.5, 1H), 2.93–2.85 (m, 1H), 2.75 ($AB_q$, $J_{AB}$=16.1, $δv_{AB}$=97.6, 2H), 2.34–2.25 (m, 2H), 2.22–2.13 (m, 1H), 2.06–1.99 (m, 1H), 1.92–1.57 (m, 4H), 1.40 (s, 9H), 1.37 (s, 3H), 1.37 (s, 3H), 1.31–1.19 (m, 1H), 1.27 (s, 3H), 0.94 (t, J=7.2, 3H), 0.82 (s, 3H); MS (ESI) 835.8 (M+H$^+$), 857.7 (M+Na$^+$); 833.7 (M−H$^+$).

To a solution of the 92d (443 mg, 0.549 mmol) in 10 mL EtOAc, was added 10% Pd/C (89 mg). The mixture was evacuated and flushed with $H_2$ (3×), then stirred under an atmosphere of $H_2$ for 2.5 h. The mixture was filtered and concentrated. The resultant residue was purified by flash chromatography (50 to 60% EtOAc/hexanes) to afford 214 mg (56%, for three steps) of Example 92 as a colorless glass. 1H NMR (300 MHz, $CDCl_3$) δ7.59–7.43 (m, 4H), 7.02–6.99 (m, 1H), 6.97 (s, 1H), 4.91 (dd, J=9.2, 4.4, 1H), 4.35 (s, 2H), 4.32 (d, J=8.8, 1H), 3.15 (q, J=6.5, 1H), 2.98 (dd, J=13.9, 4.4, 1H), 2.69 ($AB_q$, $J_{AB}$=15.7, $δv_{AB}$=70.4, 2H), 2.37–2.15 (m, 3H), 2.03 (t, J=6.1, 1H), 1.90–1.58 (m, 4H), 1.42 (s, 9H), 1.39 (s, 3H), 1.37 (s, 3H), 1.33–1.21 (m, 1H), 1.28 (s, 3H), 0.97 (t, J=7.3, 3H), 0.84 (s, 3H); MS (ESI) 701.6 (M+H$^+$), 723.6 (M+Na$^+$); 699.6 (M−H$^+$).

Example 93

(6S,8S)-N-{(1R)-1-[(3aS,4S,6S,7aR)-Hexahydro-3a,5,5-trimethyl-4,6-methano-1,3,2-benzodioxaborol-2-yl]propyl}-8-(2-anilino-2-oxoethyl)-8-methyl-4-oxo-3-{[3-(trifluoromethyl)benzyl]amino}-4,6,7,8-tetrahydropyrrolo[1,2-a]pyrimidine-6-carboxamide tert-Butyl ((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetate (93a)

Example 92 (214 mg, 0.305 mmol) was dissolved in 5 mL 4N HCl in dioxane. The mixture was stirred at rt for 3.5 h, then concentrated. The residue was triturated with $Et_2O$ to afford 195 mg (94%) of 93a as a white solid after decanting the $Et_2O$.

To a solution of 93a (11.4 mg, 0.0168) and aniline (7.3 □L, 0.084 mmol) in 5:1 $CH_2Cl_2$/DMF (1 mL), were added HOAt (2.5 mg, 0.019 mmol), NaHCO$_3$ (3.5 mg, 0.042 mmol), EDCI (4.5 mg, 0.024 mmol). The mixture was stirred at rt for 24 h, then was diluted with EtOAc. The organic phase was washed with H$_2$O, sat. NaHCO$_3$, and brine, dried (Na$_2$SO$_4$), and concentrated. The crude residue was purified by flash chromatography (80% EtOAc/hexanes), followed by preparative HPLC (gradient, 50 to 100% CH$_3$CN/H$_2$O) to afford 3.9 mg of Example 93 (28%) as the TFA salt. MS (ESI) 720.6 (M+H$^+$) 742.6 (M+Na$^+$); 718.5 (M−H$^+$).

Example 94

(6S,8S)-N-{(1R)-1-[(3aS,4S,6S,7aR)-Hexahydro-3a,
5,5-trimethyl-4,6-methano-1,3,2-benzodioxaborol-2-
yl]propyl}-8-[2-(4-nitroanilino)-2-oxoethyl]-8-
methyl-4-oxo-3-{[3-(trifluoromethyl)benzyl]
amino}-4,6,7,8-tetrahydropyrrolo[1,2-a]pyrimidine-
6-carboxamide According to the procedure for the preparation of Example 93, 93a (11.4 mg, 0.0168 mmol) and 4-nitroaniline (11.6 mg, 0.084 mmol) afforded 1.9 mg (13%) of Example 94 as the TFA salt. MS (ESI) 765.6 (M+H$^+$) 787.5 (M+Na$^+$); 763.5 (M−H$^+$).

Example 95

(6S,8S)-N-{(1R)-1-[(3aS,4S,6S,7aR)-Hexahydro-3a,
5,5-trimethyl-4,6-methano-1,3,2-benzodioxaborol-2-
yl]propyl}-8-methyl-4-oxo-8-[2-oxo-2-(2-
pyridinylamino)ethyl]-3-{[3-(trifluoromethyl)
benzyl]amino}-4,6,7,8-tetrahydropyrrolo[1,2-a]
pyrimidine-6-carboxamide According to the procedure for the preparation of Example 93, 93a (11.4 mg, 0.0168 mmol) and 2-aminopyridine (7.9 mg, 0.084 mmol) afforded 4.6 mg (29%) of Example 95 as the diTFA salt. MS (ESI) 721.6 (M+H$^+$) 743.6 (M+Na$^+$); 719.5 (M−H$^+$).

Example 96

(6S,8S)-N-{(1R)-1-[(3aS,4S,6S,7aR)-Hexahydro-3a,
5,5-trimethyl-4,6-methano-1,3,2-benzodioxaborol-2-
yl]propyl}-8-[2-(1-naphthylamino)-2-oxoethyl]-8-
methyl-4-oxo-3-{[3-(trifluoromethyl)benzyl]
amino}-4,6,7,8-tetrahydropyrrolo[1,2-a]pyrimidine-
6-carboxamide To a solution of 93a (10.0 mg, 0.0147 mmol) in 1 mL CH$_3$CN at rt, were added 1-aminonaphthalene (10 mg, 0.07 mmol), 0.5M DIEA in CH$_3$CN (74 μL, 0.0365 mmol), and 0.5M HAtU in CH$_3$CN (41 μL, 0.021 mmol). The mixture was stirred at rt for 18 h, then purified by preparative HPLC (gradient, 50 to 100% CH$_3$CN/H$_2$O+0.1% TFA) to afford 2.0 mg (17%) of Example 96 as the TFA salt. MS (HR-ESI) calculated for C$_{42}$H$_{48}$BF$_3$N$_5$O$_5$ (M+H$^+$), found 829.3534.

Example 97

(6S,8S)-N-{(1R)-1-[(3aS,4S,6S,7aR)-Hexahydro-3a,
5,5-trimethyl-4,6-methano-1,3,2-benzodioxaborol-2-
yl]propyl}-8-[2-(3-methoxyanilino)-2-oxoethyl]-8-
methyl-4-oxo-3-{[3-(trifluoromethyl)benzyl]
amino}-4,6,7,8-tetrahydropyrrolo[1,2-a]pyrimidine-
6-carboxamide According to the procedure for the preparation of Example 96, 93a (10.0 mg, 0.0147 mmol) and m-anisidine (0.07 mmol), afforded 6.3 mg (50%) of Example 97 as the TFA salt. MS (HR-ESI) calculated for C$_{39}$H$_{48}$BF$_3$N$_5$O$_6$ (M+H$^+$), found 750.3642.

Example 98

(6S,8S)-N-{(1R)-1-[(3aS,4S,6S,7aR)-Hexahydro-3a,
5,5-trimethyl-4,6-methano-1,3,2-benzodioxaborol-2-
yl]propyl}-8-[2-oxo-2-(5-quinolinylamino)ethyl]-8-
methyl-4-oxo-3-{[3-(trifluoromethyl)benzyl]
amino}-4,6,7,8-tetrahydropyrrolo[1,2-a]pyrimidine-
6-carboxamide According to the procedure for the preparation of Example 96, 93a (10.0 mg, 0.0147 mmol) and 5-aminoquinoline (0.07 mmol), afforded 4.3 mg (29%) of Example 98 as the bis TFA salt. MS (HR-ESI) calculated for C$_{41}$H$_{47}$BF$_3$N$_6$O$_5$ (M+H$^+$), found 771.3670.

Example 99

(6S,8S)-N-{(1R)-1-[(3aS,4S,6S,7aR)-Hexahydro-3a,
5,5-trimethyl-4,6-methano-1,3,2-benzodioxaborol-2-
yl]propyl}-8-{2-[(2-methyl-6-quinolinyl)amino]-2-
oxoethyl}-8-methyl-4-oxo-3-{[3-(trifluoromethyl)
benzyl]amino}-4,6,7,8-tetrahydropyrrolo[1,2-a]
pyrimidine-6-carboxamide According to the procedure for the preparation of Example 96, 93a (10.0 mg, 0.0147 mmol) and 6-amino-2-methylquinoline (0.07 mmol), afforded 9.6 mg (65%) of Example 99 as the bis TFA salt. MS (HR-ESI) calculated for C$_{42}$H$_{49}$BF$_3$N$_6$O$_5$ (M+H$^+$), found 785.3815.

Example 100

(6S,8S)-N-{(1R)-1-[(3aS,4S,6S,7aR)-Hexahydro-3a,
5,5-trimethyl-4,6-methano-1,3,2-benzodioxaborol-2-
yl]propyl}-8-[2-oxo-2-(3-pyridinylamino)ethyl]-8-
methyl-4-oxo-3-{[3-(trifluoromethyl)benzyl]
amino}-4,6,7,8-tetrahydropyrrolo[1,2-a]pyrimidine-
6-carboxamide According to the procedure for the preparation of Example 96, 93a (10.0 mg, 0.0147 mmol) and 3-aminopyridine (0.07 mmol), afforded 4.0 mg (31%) of Example 100 as the bis TFA salt. MS (HR-ESI) calculated for C$_{37}$H$_{45}$BF$_3$N$_6$O$_5$ (M+H$^+$), found 721.3490.

Example 101

(6S,8S)-N-{(1R)-1-[(3aS,4S,6S,7aR)-Hexahydro-3a,
5,5-trimethyl-4,6-methano-1,3,2-benzodioxaborol-2-
yl]propyl}-8-[2-(1-isoquinolinylamino)-2-oxoethyl]-
8-methyl-4-oxo-3-{[3-(trifluoromethyl)benzyl]
amino}-4,6,7,8-tetrahydropyrrolo[1,2-a]pyrimidine-
6-carboxamide According to the procedure for the preparation of Example 96, 93a (10.0 mg, 0.0147 mmol) and 2-aminoisoquinoline (0.07 mmol), afforded 10.3 mg (70%) of Example 101 as the bis TFA salt. MS (HR-ESI) calculated for C$_{41}$H$_{47}$BF$_3$N$_6$O$_5$ (M+H$^+$), found 771.3655.

Example 102

(6S,8S)-N-{(1R)-1-[(3aS,4S,6S,7aR)-Hexahydro-3a,
5,5-trimethyl-4,6-methano-1,3,2-benzodioxaborol-2-
yl]propyl}-2-oxoethyl]-8-methyl-4-oxo-8-[2-oxo-2-
(2-quinolinylamino)ethyl]-3-{[3-(trifluoromethyl)
benzyl]amino}-4,6,7,8-tetrahydropyrrolo[1,2-a]
pyrimidine-6-carboxamide According to the procedure for the preparation of Example 96, 93a (10.0 mg, 0.0147 mmol) and 2-aminoquinoline (0.07 mmol), afforded 9.5 mg (65%) of Example 102 as the bis TFA salt. MS (HR-ESI) calculated for $C_{41}H_{47}BF_3N_6O_5$ (M+H$^+$), found 771.3669.

Example 103

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-(2-methoxyanilino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 96, 93a (10.0 mg, 0.0147 mmol) and o-anisidine (0.07 mmol), afforded 1.9 mg (15%) of Example 103 as the TFA salt. MS (HR-ESI) calculated for $C_{39}H_{48}BF_3N_5O_6$ (M+H$^+$), found 750.3672.

Example 104

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-([1,1'-biphenyl]-4-ylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 96, 93a (10.0 mg, 0.0147 mmol) and 4-aminobiphenyl (0.07 mmol), afforded 7.3 mg (55%) of Example 104 as the TFA salt. MS (HR-ESI) calculated for $C_{44}H_{50}BF_3N_5O_5$ (M+H$^+$), found 796.3858.

Example 105

Methyl 4-{[(((6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetyl]amino}benzoate According to the procedure for the preparation of Example 96, 93a (10.0 mg, 0.0147 mmol) and methyl 4-aminobenzoate (0.07 mmol), afforded 4.0 mg (31%) of Example 105 as the TFA salt. MS (HR-ESI) calculated for $C_{40}H_{48}BF_3N_5O_7$ (M+H$^+$), found 778.3605.

Example 106

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-([benzylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 96, 93a (10.0 mg, 0.0147 mmol) and benzylamine (0.07 mmol), afforded 6.5 mg (52%) of Example 106 as the TFA salt. MS (HR-ESI) calculated for $C_{39}H_{47}BF_3N_5O_6$ (M+H$^+$), found 734.3714.

Example 107

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-{2-[4-(hydroxymethyl)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 96, 93a (10.0 mg, 0.0147 mmol) and 4-aminobenzyl alcohol (0.07 mmol), afforded 4.6 mg (36%) of Example 107 as the TFA salt. MS (HR-ESI) calculated for $C_{39}H_{48}BF_3N_5O_6$ (M+H$^+$), found 750.3664.

Example 108

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-{2-[4-(dimethylamino)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 96, 93a (10.0 mg, 0.0147 mmol) and N,N-dimethyl-1,4-phenylenediamine (0.07 mmol), afforded 2.4 mg (17%) of Example 108 as the bis TFA salt. MS (HR-ESI) calculated for $C_{40}H_{51}BF_3N_6O_5$ (M+H$^+$), found 763.3995.

Example 109

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-(4-tert-butylanilino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 96, 93a (10.0 mg, 0.0147 mmol) and 4-t-butylaniline (0.07 mmol), afforded 8.0 mg (61%) of Example 109 as the TFA salt. MS (HR-ESI) calculated for $C_{42}H_{54}BF_3N_5O_5$ (M+H$^+$), found 776.4190.

Example 110

(6S,8S)-N-{(1R)-1-[(3aS,4S,6S,7aR)-Hexahydro-3a, 5,5-trimethyl-4,6-methano-1,3,2-benzodioxaborol-2-yl]propyl}-2-oxoethyl}-8-methyl-4-oxo-8-{2-[3-(trifluoromethyl)anilino]-3-{[3-(trifluoromethyl)benzyl]amino}-4,6,7,8-tetrahydropyrrolo[1,2-a]pyrimidine-6-carboxamide According to the procedure for the preparation of Example 96, 93a (10.0 mg, 0.0147 mmol) and 3-(trifluoromethyl)aniline (0.07 mmol), afforded 6.2 mg (47%) of Example 110 as the TFA salt. MS (HR-ESI) calculated for $C_{39}H_{45}BF_6N_5O_6$ (M+H$^+$), found 788.3429.

Example 111

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-{2-[4-(benzyloxy)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 96, 93a (10.0 mg, 0.0147 mmol) and 4-benzyloxyaniline hydrochloride (0.07 mmol), afforded 7.7 mg (56%) of Example 111 as the TFA salt. MS (HR-ESI) calculated for $C_{45}H_{52}BF_3N_5O_6$ (M+H$^+$), found 826.3974.

Examples 112 and 113 tert-Butyl((6S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-4-oxo-3-{[3-(trifluoromethyl)benzyl]amino}-4,6,7,8-tetrahydropyrrolo[1,2-a]pyrimidin-8-yl)acetate (C8 diastereomers)

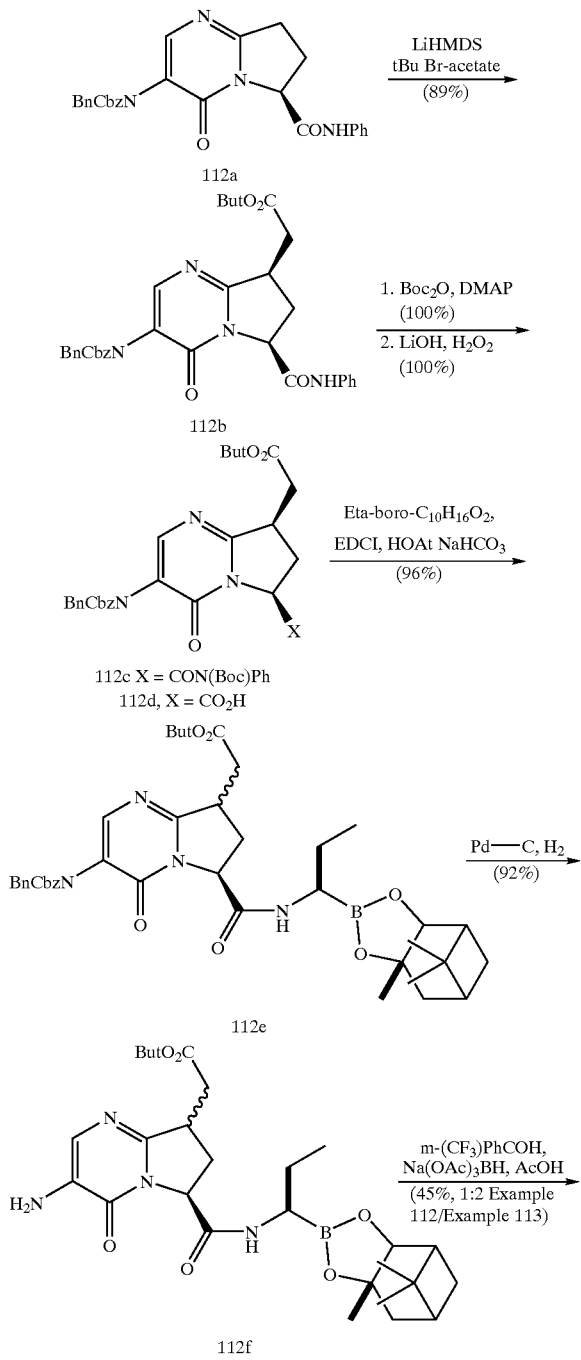

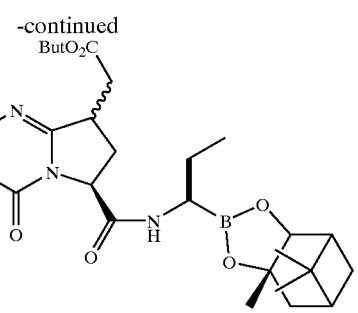

Examples 112 and 113
(C8 diastereomers)

Benzyl (6S)-6-(anilinocarbonyl)-4-oxo-4,6,7,8-tetrahydropyrrolo[1,2-a]pyrimidin-3-yl(benzyl)carbamate (112a)

According to the procedure for the preparation of 12b, 112a was prepared using benzyl bromide. $^1$H NMR (300 MHz, CDCl$_3$) δ9.40 (br s, 1H), 7.49 (d, J=7.7, 2H), 7.33–7.21 (m, 12H), 7.12 (t, J=7.3, 1H), 5.31 (d, J=8.4, 1H), 5.18 (br s, 2H), 4.81 (br s, 1H), 3.45–3.32 (m, 1H), 3.03–2.91 (m, 2H), 2.43–2.30 (m, 1H). MS (ESI) 495.4 (M+H$^+$), 517.4 (M+Na$^+$), 493.4 (M–H$^+$).

tert-Butyl ((6S,8R)-6-(anilinocarbonyl)-3-{benzyl[(benzyloxy)carbonyl]amino}-4-oxo-4,6,7,8-tetrahydropyrrolo[1,2-a]pyrimidin-8-yl)acetate (112b)

To a solution of 112a (101.6 mg, 0.205 mmol) in 1 mL THF at –78° C., was added 1N LiHMDS in THF (0.431 mL, 0.431 mmol). The mixture was stirred at –78° C. for 10 min, then t-butyl bromoacetate (30.3 μL, 0.205 mmol) was added, dropwise. The mixture was stirred at –78° C. for 5 h, then quenched with sat. NH$_4$Cl. The mixture was diluted with EtOAc and washed with sat. NH$_4$Cl and brine, dried (Na$_2$SO$_4$), and concentrated. The crude product was purified by flash chromatography to afford 110.7 mg (89%) of 112b. $^1$H NMR (300 MHz, CDCl$_3$) δ9.38 (br s, 1H), 7.63 (br s, 1H), 7.45 (d, J=8.1, 2H), 7.33–7.17 (m, 12H), 7.02 (t, J=7.3, 1H), 5.17–5.11 (m, 3H), 4.84 (br s, 1H), 4.69 (br s, 1H), 3.62–3.51 (m, 1H), 2.84 (d, J=6.9, 2H), 2.79–2.67 (m, 1H), 2.40 (br s, 1H), 1.43 (s, 9H); MS (ESI) 609.2 (M+H$^+$), 631.2 (M+Na$^+$), 607.2 (M–H$^+$).

tert-butyl ((6S,8R)-3-{benzyl[(benzyloxy)carbonyl]amino}-6-{[(tert-butoxycarbonyl)anilino]carbonyl}-4-oxo-4,6,7,8-tetrahydropyrrolo[1,2-a]pyrimidin-8-yl)acetate (112c)

To a solution of 112b (110.7 mg, 0.182 mmol) in 5 mL CH$_3$CN at rt, was added DMAP (11.1 mg, 0.091 mmol) and Boc2O (119 mg, 0.546 mmol). The mixture was stirred at rt for 2.5 h, then diluted with EtOAc. The organic phase was washed with 1N HCl, H$_2$O, sat. NaHCO$_3$, H$_2$O, and brine, dried (Na$_2$SO$_4$), and concentrated. The crude product was purified by flash chromatography (30% EtOAc/hexanes) to afford 128.9 mg (100%) of 112c. $^1$H NMR (300 MHz, CDCl$_3$) δ7.49 (br s, 1H), 7.43–7.32 (m, 3H), 7.25–7.22 (m, 12H), 5.93 (dd, J=9.1, 5.5, 1H), 5.22–5.17 (m, 2H), 5.13 (br s, 1H), 4.80 (br s, 1H), 3.67–3.56 (m, 1H), 3.18–3.05 (m, 1H), 2.90 (dd, J=16.8, 3.7, 1H), 2.53 (dd, J=16.8, 10.6, 1H), 2.21–2.10 (m, 1H), 1.44 (s, 9H), 1.40 (s, 9H); MS (ESI) 709.3 (M+H$^+$), 731.2 (M+Na$^+$), 707.2 (M–H$^+$).

(6S)-3-{Benzyl[(benzyloxy)carbonyl]amino}-8-(2-tert-butoxy-2-oxoethyl)-4-oxo-4,6,7,8-tetrahydropyrrolo[1,2-a]pyrimidine-6-carboxylic acid (112d)

To a solution of 112c (128.9 mg, 0.182 mmol) in 4:1 THF/H$_2$O (5 mL) at 0° C., were added 30% H$_2$O$_2$ (83 μL, 0.728 mmol) and 1N LiOH (291 μL, 0.291 mmol). The mixture was allowed to slowly warm to rt and was stirred 14 h. The mixture was diluted with EtOAc and shaken with aq. $Na_2SO_3$. The mixture was acidified to pH ~2, then extracted with EtOAc (3×). The combined organic phase was washed with $H_2O$ and brine, dried ($Na_2SO_4$), and concentrated to afford acid 130 mg (quantitative) of 112d as a mixture of C8 diastereomers, along with an equal molar amount of BocNHPh, which was used in the following step without further purification. MS (ESI) 709.3 ($M+H^+$), 731.2 ($M+Na^+$), 707.2 ($M-H^+$).

tert-Butyl((6S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-3-{benzyl[(benzyloxy)carbonyl]amino}-4-oxo-4,6,7,8-tetrahydropyrrolo[1,2-a]pyrimidin-8-yl)acetate (112e)

To a solution of 112d (0.182 mmol) and Etg-boro-$C_{10}H_{16}O_2$ (3-12e) (59.8 mg, 0.218 mmol) in 5:1 $CH_2Cl_2$/DMF (2.4 mL) at 0° C., was added HOAt (27.2 mg, 0.200 mmol), $NaHCO_3$ (38.2 mg, 0.455 mmol), and EDCI (48.9 mg, 0.255 mmol). The mixture was stirred at 0° C. for 1 h. The mixture was diluted with EtOAc and washed with 1N HCl, $H_2O$, sat. $NaHCO_3$, $H_2O$, and brine, dried ($Na_2SO_4$), and concentrated. The mixture was purified by flash chromatography (1:1 EtOAc/hexanes) to afford 116 mg (96%) of 112e as a mixture of C8 diastereomers. MS (ESI) 753.3 ($M+H^+$), 775.3 ($M+Na^+$), 751.4 ($M-H^+$).

tert-Butyl{(6S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-3-amino-4-oxo-4,6,7,8-tetrahydropyrrolo[1,2-a]pyrimidin-8-yl}acetate hydrochloride (112f)

To a solution of 112e (116 mg, 0.175 mmol) in 10:1 MeOH/$H_2O$ (3 mL), was added 10% Pd-C (20 mg). The mixture was evacuated and flushed with $H_2$ (3×), then stirred under an atmosphere of $H_2$ for 1 h. The mixture was filtered and concentrated to afford 85.0 mg (92%) of 112f, which was used in the following step without further purification.

Example 112 and Example 113

To a solution of 112f (85.0 mg, 0.161 mmol) in DCE (2 mL), was added m-trifluoromethylbenzaldehyde (212 μL, 1.61 mmol), AcOH (46 μL, 0.80 mmol), and $Na(OAc)_3BH$ (341 mg, 1.61 mmol). The mixture was stirred at rt for 16 h, then was diluted with EtOAc. The organic phase was washed with sat. $NaHCO_3$ (2×) and brine, dried ($Na_2SO_4$), and concentrated. The crude product was purified by flash chromatography (50 to 55 to 60% EtOAc/hexanes), followed by HPLC (gradient, 50 to 100% $CH_3CN/H_2O+0.1\%$ TFA) to afford 20.0 mg (16%) of the less polar diastereomer Example 112 and 37.0 mg (29%) of the more polar diastereomer Example 113, both as TFA salts.

Data for Example 112: MS (HR-ESI) calculated for $C_{35}H_{47}BF_3N_4O_6$ ($M+H^+$), found 687.3549.

Data for Example 113: MS (HR-ESI) calculated for $C_{35}H_{47}BF_3N_4O_6$ ($M+H^+$), found 687.3552.

Example 114

(6S)-N-{(1R)-1-[(3aS,4S,6S,7aR)-Hexahydro-3a,5,5-trimethyl-4,6-methano-1,3,2-benzodioxaborol-2-yl]propyl}-8-(2-anilino-2-oxoethyl)-4-oxo-3-{[3-(trifluoromethyl)benzyl]amino}-4,6,7,8-tetrahydropyrrolo[1,2-a]pyrimidine-6-carboxamide (less polar C8 diastereomer)

((6S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-4-oxo-3-{[3-(trifluoromethyl)benzyl]amino}-4,6,7,8-tetrahydropyrrolo[1,2-a]pyrimidin-8-yl)acetic acid hydrochloride (114a)

Example 112 (13.6 mg, 0.0170 mmol) was stirred in 1 mL 4N HCl/dioxane for 1.5 h, then concentrated to afford 114a. The material was used as is in the following step without further purification.

According to the procedure for the preparation of 12b, 114a (0.0170 mmol) afforded 3.0 mg (25%) of Example 114. MS (HR-ESI) calculated for $C_{37}H_{43}BF_3N_5O_5$ ($M+H^+$), found 706.3389.

Example 115

(6S)-N-{(1R)-1-[(3aS,4S,6S,7aR)-Hexahydro-3a,5,5-trimethyl-4,6-methano-1,3,2-benzodioxaborol-2-yl]propyl}-8-(2-anilino-2-oxoethyl)-4-oxo-3-{[3-(trifluoromethyl)benzyl]amino}-4,6,7,8-tetrahydropyrrolo[1,2-a]pyrimidine-6-carboxamide (more polar C8 diastereomer)

According to the procedure for the preparation of Example 114, Example 112 (14.9 mg, 0.0186 mmol) afforded 5.0 mg (38%) of Example 115. MS (HR-ESI) calculated for $C_{37}H_{43}BF_3N_5O_5$ ($M+H^+$), found 706.3373.

Example 116

(6S,8R)-N-{(1R)-1-[(3aS,4S,6S,7aR)-Hexahydro-3a,5,5-trimethyl-4,6-methano-1,3,2-benzodioxaborol-2-yl]propyl}-8-methyl-4-oxo-8-(3-phenylpropyl)-3-{[3-(trifluoromethyl)benzyl]amino}-4,6,7,8-tetrahydropyrrolo[1,2-a]pyrimidine-6-carboxamide

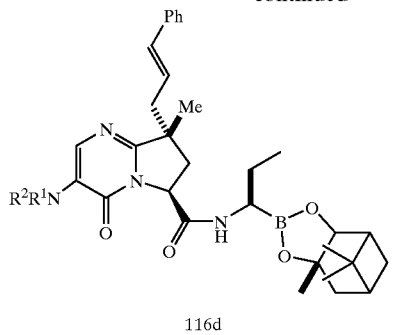

116d

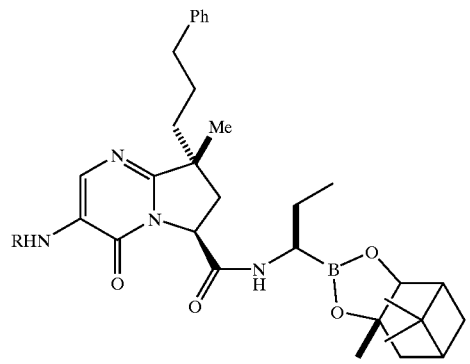

116e, R = H
Example 116, R = 3-(CF₃)benzyl

Benzyl (6S,8R)-6-(anilinocarbonyl)-8-methyl-4-oxo-8-[(2E)-3-phenyl-2-propenyl]-4,6,7,8-tetrahydropyrrolo[1,2-a]pyrimidin-3-yl(benzyl)carbamate (116a)

To a solution of 12c (32 mg, 0.063 mmol) in 1 mL THF at −78° C., was added LiHMDS (157 μL, 0.157 mmol). The mixture was stirred at −78° C. for 10 min, then cinnamyl bromide (18.6 mg, 0.095 mmol) in 250 μL THF was added. The reaction was stirred at −78° C. for 1.5 h, then quenched with sat. NH₄Cl. The mixture was diluted with EtOAc, washed with sat NH₄Cl and brine, dried (Na₂SO₄), and concentrated. The crude mixture was purified by flash chromatography (35% EtOAc/hexanes) to afford 26.0 mg (66%) of 116a. ¹H NMR (300 MHz, CDCl₃) δ9.57 (br s, 1H), 7.74 (br s, 1H), 7.47 (d, J=8.1, 2H), 7.29–7.23 (m, 17H), 7.07 (t, J=7.5, 1H), 6.47 (d, J=15.7, 1H), 6.02–5.97 (m, 1H), 5.20–5.17 (m, 3H), 4.80 (br s, 1H), 2.70–2.41 (m, 4H), 1.48 (s, 3H).

Benzyl (6S,8R)-6-(anilinocarbonyl)-8-methyl-4-oxo-8-[(2E)-3-phenyl-2-propenyl]-4,6,7,8-tetrahydropyrrolo[1,2-a]pyrimidin-3-yl(benzyl)carbamate (116b)

According to the procedure for the preparation of 12e, 116a (26 mg, 0.042 mmol) afforded 30.1 mg (quantitative) of imide 116b. ¹H NMR (300 MHz, CDCl₃) δ7.59 (br s, 1H), 7.42–7.17 (m, 20H), 6.48 (d, J=15.8, 1H), 6.03 (br s, 1H), 5.85 (dd, J=10.0, 4.2, 1H), 5.22–5.10 (m, 3H), 4.78 (br s, 1H), 2.90 (dd, J=14.0, 10.0, 1H), 2.64–2.50 (m, 2H), 2.21 (dd, J=14.1, 4.2, 1H), 1.41 (s, 3H), 1.37 (s, 3H).

(6S,8R)-3-{Benzyl[(benzyloxy)carbonyl]amino}-8-methyl-4-oxo-8-[(2E)-3-phenyl-2-propenyl]-4,6,7,8-tetrahydropyrrolo[1,2-a]pyrimidine-6-carboxylic acid (116c)

According to the procedure for the preparation of 12f, 116b (30.1 mg, 0.0415 mmol) afforded 31 mg (quantitative) of a 1:1 mixture of acid 116c and BocNHPh, which was used without further purification in the following step.

Benzyl (6S,8R)-6-[({(1R)-1-[(3aS,4S,6S,7aR)-hexahydro-3a,5,5-trimethyl-4,6-methano-1,3,2-benzodioxaborol-2-yl] propyl}amino)carbonyl]-8-methyl-4-oxo-8-[(2E)-3-phenyl-2-propenyl]-4,6,7,8-tetrahydropyrrolo[1,2-a]pyrimidin-3-yl (benzyl)carbamate (116d)

According to the procedure for the preparation of 12g, 116c (0.0415 mmol) afforded 23.8 mg (75%) of 116d. MS (ESI) 803.4 (M+Cl⁻), (6S,8R)-N-{(1R)-1-[(3aS,4S,6S,7aR)-hexahydro-3a,5,5-trimethyl-4,6-methano-1,3,2-benzodioxaborol-2-yl]propyl}-3-amino-8-methyl-4-oxo-8-(3-phenylpropyl)-4,6,7,8-tetrahydropyrrolo[1,2-a]pyrimidine-6-carboxamide (116e)

To a solution of 116d in MeOH (2 mL), were added conc. HCl (3 drops) and 10% Pd-C (10 mg). The mixture was evacuated and flushed with H₂ (3×), then stirred under an atmosphere of H₂ for 45 min. The mixture was filtered and concentrated to afford 17.3 mg (96%) of 116e as the HCl salt. MS (ESI) 547.3 (M+H⁺), 569.3 (M+Na⁺), 545.2 (M−H⁺).

According to the procedure for the preparation of Example 112, 116e (17.2 mg, 0.0295 mmol) afforded after preparative HPLC purification (gradient, 70 to 100% CH₃CN/H₂O) 3.5 mg (14%) of Example 116 as the TFA salt. MS (HR-ESI) calculated for $C_{39}H_{49}BF_3N_4O_4$ (M+H⁺), found 705.3808.

Example 117

(6S,8S)-N-{(1R)-1-[(3aS,4S,6S,7aR)-Hexahydro-3a,5,5-trimethyl-4,6-methano-1,3,2-benzodioxaborol-2-yl]propyl}-8-(2-anilino-2-oxoethyl)-8-methyl-4-oxo-3-{[3-(trifluoromethyl)benzyl]amino}-4,6,7,8-tetrahydropyrrolo[1,2-a]pyrimidine-6-carboxamide

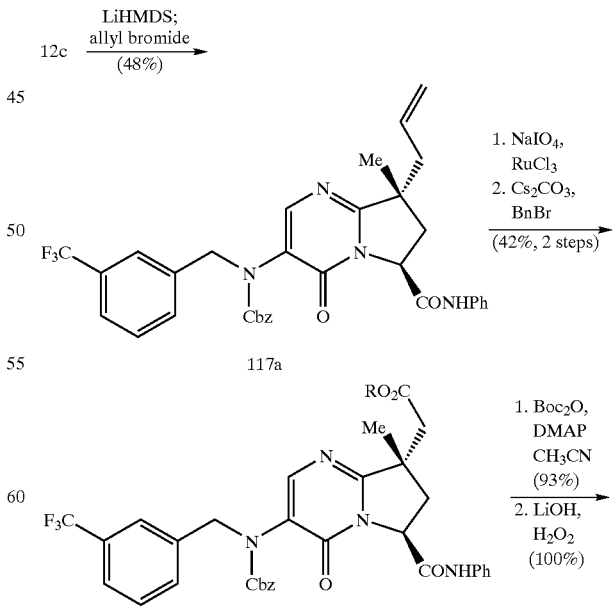

117b, R = H
117c, R = Bn

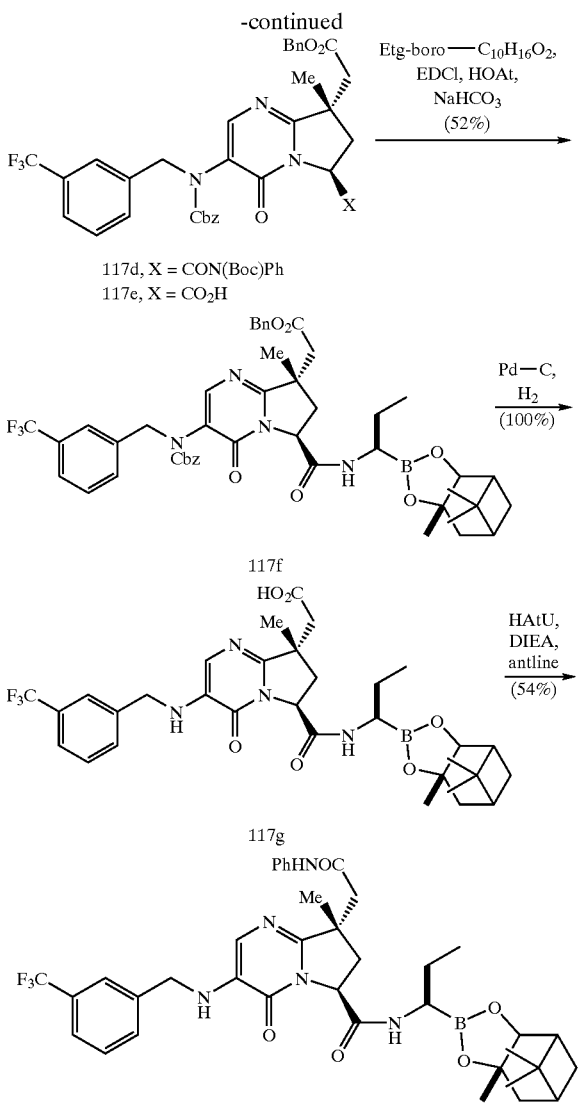

Example 117

Benzyl (6S,8R)-8-allyl-6-(anilinocarbonyl)-8-methyl-4-oxo-4,6,7,8-tetrahydropyrrolo[1,2-a]pyrimidin-3-yl[3-(trifluoromethyl)benzyl]carbamate (117a)

To a solution of 12c (2.155 g, 3.74 mmol) in 16 mL THF at −78° C., was added 1.0 M LIHMDS in THF (7.66 mL, 7.66 mmol). The mixture was stirred at −78° C. for 10 min, then allyl bromide (0.81 mL, 9.34 mmol) was added. The mixture was allowed to slowly warm to −40° C. and was maintained at this temperature for 30 min. The reaction was quenched with sat. NH$_4$Cl, then diluted with EtOAc. The organic phase was washed with 0.5 M HCl and brine, dried (Na$_2$SO$_4$), and concentrated. The crude residue was purified by flash chromatography (40% EtOAc/hexanes) to afford 1.101 g (48%) of 117a as a colorless gum. MS (ESI) 617.2 (M+H$^+$).

((6S,8S)-6-(Anilinocarbonyl)-3-{[(benzyloxy)carbonyl][3-(trifluoromethyl)benzyl]amino}-8-methyl-4-oxo-4,6,7,8-tetrahydropyrrolo[1,2-a]pyrimidin-8-yl)acetic acid (117b)

To a solution of 117a (1.073 g, 1.740 mmol) in 15.4 mL CH$_3$CN/CCl$_4$/H$_2$O (2:2:3), were added NaIO$_4$ (1.56 g, 7.31 mmol) and a solution of RuCl$_3$.H$_2$O (18 mg, 0.087 mmol) in 2.25 mL of CH$_3$CN/CCl$_4$/H$_2$O (2:2:3). The mixture was stirred vigorously for 16 h, then was poured into H$_2$O and extracted with CH$_2$Cl$_2$ (2×). The combined organic phase was dried (Na$_2$SO$_4$), filtered, and concentrated in vacuo to afford 1.17 g of 117b as a brown foam, which was used in the following step without further purification. MS (ESI) 657.3 (M+Na$^+$); 633.4 (M−H$^+$).

Benzyl ((6S,8S)-6-(anilinocarbonyl)-3-{[(benzyloxy)carbonyl][3-(trifluoromethyl)benzyl]amino}-8-methyl-4-oxo-4,6,7,8-tetrahydropyrrolo[1,2-a]pyrimidin-8-yl)acetate (117c)

To a solution of 117b (1.740 mmol) in 7 mL DMF, were added Cs$_2$CO$_3$ (850 mg, 2.61 mmol) and BnBr (0.31 mL, 2.61 mmol). The mixture was stirred at rt for 1 h, then diluted with EtOAc. The organic phase was washed with 0.5 N HCl and brine, dried (Na$_2$SO$_4$), and concentrated. The crude product was purified by flash chromatography (35% EtOAc/hexanes) to afford 533 mg (42%, 2 steps) of 117c as a colorless glass. MS(ESI) 725.3 (M+H$^+$).

Benzyl ((6S,8S)-3-{[(benzyloxy)carbonyl][3-(trifluoromethyl)benzyl]amino}-6-{[(tert-butoxycarbonyl)anilino]carbonyl}-8-methyl-4-oxo-4,6,7,8-tetrahydropyrrolo[1,2-a]pyrimidin-8-yl)acetate (117d)

To a solution of 117c (530 mg, 0.731 mmol) in 6 mL CH$_3$CN, were added Boc$_2$O (0.479 g, 2.19 mmol) and DMAP (45 mg, 0.366 mmol). The mixture was stirred at rt for 45 min, then diluted with EtOAc. The organic phase was washed with 0.5 M HCl and brine, dried (Na$_2$SO$_4$), and concentrated. The product was purified by flash chromatography (25% EtOAc/hexanes) to afford 560 mg (93%) of 117d as a colorless glass. MS(ESI) 825.3 (M+H$^+$).

(6S,8S)-3-{[(Benzyloxy)carbonyl][3-(trifluoromethyl)benzyl]amino}-8-[2-(benzyloxy)-2-oxoethyl]-8-methyl-4-oxo-4,6,7,8-tetrahydropyrrolo[1,2-a]pyrimidine-6-carboxylic acid (117e)

To a solution of 117d (537 mg, 0.651 mmol) in 4:1 THF/H20 at 0° C., were added 30% H$_2$O$_2$ (0.295 mL, 2.604 mmol) and 1M LiOH (1.107 mL, 1.107 mmol). The mixture was stirred at 0° C. for 2 h, then a solution of Na$_2$SO$_3$ (140 mg, 1.107 mmol) in 1 mL H$_2$O was added dropwise. The mixture was poured into 0.5 M HCl and the product was extracted with EtOAc. The organic phase was washed with brine, dried (Na$_2$SO$_4$), and concentrated to afford 527 mg of 117e, which was contaminated with BocNHPh. The mixture was used as is in the following step. MS(ESI) 650.3 (M+H$^+$); 648.3 (M−H$^+$).

Benzyl ((6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-3-{[(benzyloxy)carbonyl][3-(trifluoromethyl)benzyl]amino}-8-methyl-4-oxo-4,6,7,8-tetrahydropyrrolo[1,2-a]pyrimidin-8-yl)acetate (117f)

To a solution of 117e (0.651 mmol) in 3.9 mL 5:1 CH$_2$Cl$_2$/DMF at 0° C., were added HOAt (97 mg, 0.716 mmol), EDCI (137 mg, 0.716 mmol), Etg-boro-C$_{10}$H$_{16}$O$_2$ (3-12e), and NaHCO3 (137 mg, 1.63 mmol). The mixture was stirred at rt for 2 h, then was diluted with EtOAc. The organic phase was washed with half-saturated NaHCO$_3$, 0.5 M HCl, and brine, dried (Na$_2$SO$_4$), and concentrated. The crude product was purified by flash chromatography (40% EtOAc/hexanes) to afford 296 mg (52%) of 117f as a colorless glass. MS(ESI) 869.5 (M+H$^+$), 891.5 (M+H$^+$).

((6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetic acid (117g)

To a solution of 117f (293 mg, 0.337 mmol) in 5 mL MeOH, was added 29 mg 10% Pd-C. The mixture was evacuated and flushed with H$_2$ (3×), then was stirred under an atmosphere of H$_2$ for 45 min. The mixture was filtered and concentrated in vacuo to afford 217 mg (100%) of 117g as a colorless glass. MS(ESI) 645.4 (M+H$^+$)

To a solution of 117g (10 mg, 0.0155 mmol) in 1 mL CH$_3$CN, were added aniline (7.2 mg, 0.0766 mmol), a 0.5 M solution of DIEA in CH$_3$CN (62 □L, 0.031 mmol), and 0.5 M solution of HAtU in CH$_3$CN (39 □L, 0.019 mmol). The mixture was stirred at rt for 6 h, then was purified by HPLC to afford 7.0 mg (54%) of Example 117 as the TFA salt. MS (HR-ESI) calculated for C$_{38}$H$_{45}$BF$_3$N$_5$O$_5$ (M+H$^+$), found 720.3553.

Example 118

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-(benzylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and benzylamine (0.0766 mmol) afforded 7.8 mg (59%) of Example 118 as the TFA salt. MS (HR-ESI) calculated for C$_{39}$H$_{47}$BF$_3$N$_5$O$_5$ (M+H$^+$), found 734.3704.

Example 119

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-(1-isoquinolinylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and 1-aminoisoquinoline (0.0766 mmol) afforded 9.7 mg (63%) of Example 119 as the bis-TFA salt. MS (HR-ESI) calculated for C$_{41}$H$_{46}$BF$_3$N$_6$O$_5$ (M+H$^+$), found 771.3679.

Example 120

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-(2-methoxyanilino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and o-anisidine (0.0766 mmol) afforded 7.1 mg (53%) of Example 120 as the TFA salt. MS (HR-ESI) calculated for C$_{39}$H$_{47}$BF$_3$N$_5$O$_6$ (M+H$^+$), found 750.3679.

Example 121

Methyl 2-{[(((6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetyl]amino}benzoate According to the procedure for the preparation of Example 117, 117g (10.0 mg, 0.0155 mmol) and methyl anthrinilate (0.0766 mmol) afforded 1.9 mg (14%) of Example 121 as the TFA salt. MS (HR-ESI) calculated for C$_{40}$H$_{47}$BF$_3$N$_5$O$_7$ (M+H$^+$), found 778.3575.

Example 122

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-[2-oxo-2-(3-pyridinylamino)ethyl]-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and 3-aminopyridine (0.0766 mmol) afforded 8.9 mg (61%) of Example 122 as the bis-TFA salt. MS (HR-ESI) calculated for C$_{37}$H$_{44}$BF$_3$N$_6$O$_5$ (M+H$^+$), found 721.3480.

Example 123

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-{2-[2-(hydroxymethyl)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and 2-aminobenzyl alcohol (0.0766 mmol) afforded 6.6 mg (49%) of Example 123 as the TFA salt. MS (HR-ESI) calculated for C$_{39}$H$_{47}$BF$_3$N$_5$O$_6$ (M+H$^+$), found 750.3657.

Example 124

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-(4-benzyl-1-piperidinyl)-2-oxoethyl]-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and 4-benzylpiperidine (0.0766 mmol) afforded 7.1 mg (50%) of Example 124 as the TFA salt. MS (HR-ESI) calculated for C$_{44}$H$_{55}$BF$_3$N$_5$O$_5$ (M+H$^+$), found 802.4321.

Example 125

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-{2-oxo-2-[4-(2-oxo-2,3-dihydro-1H-benzimidazol-1-yl)-1-piperidinyl]ethyl}-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and 4-(2-keto-1-benzimidaolinyl)piperidine (0.0766 mmol) afforded 8.0 mg (54%) of Example 125 as the TFA salt. MS (HR-ESI) calculated for C$_{44}$H$_{53}$BF$_3$N$_7$O$_6$ (M+H$^+$), found 844.4196.

Example 126

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-[2-(3-methyl-3-phenyl-1-piperidinyl)-2-oxoethyl]-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and 3-methyl- 3-phenylpiperidine (0.0766 mmol) afforded 8.9 mg (63%) of Example 126 as the TFA salt. MS (HR-ESI) calculated for $C_{44}H_{55}BF_3N_5O_5$ (M+H$^+$), found 802.4304.

Example 127

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-(4-benzyl-4-hydroxy-1-piperidinyl)-2-oxoethyl]-8-methyl-4-oxo-3-{([3-(trifluoromethyl) benzyl]amino}-4,6,7,8-tetrahydropyrrolo[1,2-a] pyrimidine-6-carboxamide According to the procedure for the preparation of Example 117, 117g (10.0 mg, 0.0155 mmol) and 4-benzyl-4-hydroxypiperidine (0.0766 mmol) afforded 8.1 mg (56%) of Example 127 as the TFA salt. MS (HR-ESI) calculated for $C_{44}H_{55}BF_3N_5O_6$ (M+H$^+$), found 818.4303.

Example 128

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-(4-benzyl-1-piperazinyl)-2-oxoethyl]-8-methyl-4-oxo-3-{[3-(trifluoromethyl) benzyl]amino}-4,6,7,8-tetrahydropyrrolo[1,2-a] pyrimidine-6-carboxamide According to the procedure for the preparation of Example 117, 117g (10.0 mg, 0.0155 mmol) and 1-benzylpiperazine (0.0766 mmol) afforded 8.6 mg (54%) of Example 128 as the bis-TFA salt. MS (HR-ESI) calculated for $C_{43}H_{54}BF_3N_6O_5$ (M+H$^+$), found 803.4268.

Example 129

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-[2-oxo-2-(4-phenyl-1-piperazinyl)ethyl]-3-{[3-(trifluoromethyl)benzyl] amino}-4,6,7,8-tetrahydropyrrolo[1,2-a]pyrimidine-6-carboxamide According to the procedure for the preparation of Example 117, 117g (10.0 mg, 0.0155 mmol) and 1-phenylpiperazine (0.0766 mmol) afforded 8.1 mg (51%) of Example 129 as the bis-TFA salt. MS (HR-ESI) calculated for $C_{42}H_{52}BF_3N_6O_5$ (M+H$^+$), found 789.4134.

Example 130

Benzyl 4-[(((6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl] amino}-4,6,7,8-tetrahydropyrrolo[1,2-a]pyrimidin-8-yl)acetyl]-1-piperazinecarboxylate According to the procedure for the preparation of Example 117, 117g (10.0 mg, 0.0155 mmol) and benzyl 1-piperazinecarboxylate (0.0766 mmol) afforded 9.3 mg (62%) of Example 130 as the TFA salt. MS (HR-ESI) calculated for $C_{44}H_{54}BF_3N_6O_7$ (M+H$^+$), found 847.4175.

Example 131

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-[2-(3,4-dihydro-2(1H)-isoquinolinyl)-2-oxoethyl]-8-methyl-4-oxo-3-{[3-(trifluoromethyl) benzyl]amino}-4,6,7,8-tetrahydropyrrolo[1,2-a] pyrimidine-6-carboxamide According to the procedure for the preparation of Example 117, 117g (10.0 mg, 0.0155 mmol) and 1,2,3,4-tetrahydroisoquinoline (0.0766 mmol) afforded 5.7 mg (42%) of Example 131 as the TFA salt. MS (HR-ESI) calculated for $C_{41}H_{49}BF_3N_5O_5$ (M+H$^+$), found 760.3851.

Example 132

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-{2-[4-(4-acetylphenyl)-1-piperazinyl]-2-oxoethyl}-8-methyl-4-oxo-3-{[3-(trifluoromethyl) benzyl]amino}-4,6,7,8-tetrahydropyrrolo[1,2-a] pyrimidine-6-carboxamide According to the procedure for the preparation of Example 117, 117g (10.0 mg, 0.0155 mmol) and 4-piperazinoacetophenone (0.0766 mmol) afforded 7.8 mg (48%) of Example 132 as the bis-TFA salt. MS (HR-ESI) calculated for $C_{44}H_{54}BF_3N_6O_6$ (M+H$^+$), found 831.4241.

Example 133

(6S,8S) —N-{(1R)-1-[(3aS,4S,6S,7aR)-Hexahydro-3a,5,5-trimethyl-4,6-methano-1,3,2-benzodioxaborol-2-yl]propyl}-8-methyl-8-{2-[3-(methylsulfanyl)anilino]-2-oxoethyl}-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and 3-(methylthio)aniline (0.0766 mmol) afforded 7.5 mg (55%) of Example 133 as the TFA salt. MS (HR-ESI) calculated for $C_{39}H_{47}BF_3N_5O_5S$ (M+H$^+$), found 766.3443.

Example 134

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-{2-[(2-methyl-4-quinolinyl) amino]-2-oxoethyl}-4-oxo-3-{[3-(trifluoromethyl) benzyl]amino}-4,6,7,8-tetrahydropyrrolo[1,2-a] pyrimidine-6-carboxamide According to the procedure for the preparation of Example 117, 117g (10.0 mg, 0.0155 mmol) and 4-amino-2-methylquinoline (0.0766 mmol) afforded 8.5 mg (54%) of Example 134 as the bis TFA salt. MS (HR-ESI) calculated for $C_{42}H_{48}BF_3N_6O_5$ (M+H$^+$), found 785.3803.

Example 135

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-[2-(1-naphthylamino)-2-oxoethyl]-4-oxo-3-{[3-(trifluoromethyl)benzyl] amino}-4,6,7,8-tetrahydropyrrolo[1,2-a]pyrimidine-6-carboxamide According to the procedure for the preparation of Example 117, 117g (10.0 mg, 0.0155 mmol) and 1-aminonaphthylene (0.0766 mmol) afforded 5.6 mg (41%) of Example 135 as the TFA salt. MS (HR-ESI) calculated for $C_{42}H_{47}BF_3N_5O_5$ (M+H$^+$), found 770.3690.

Example 136

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-methyl-8-[2-(2-nitroanilino)-2-oxoethyl]-4-oxo-3-{[3-(trifluoromethyl)benzyl] amino}-4,6,7,8-tetrahydropyrrolo[1,2-a]pyrimidine-6-carboxamide According to the procedure for the preparation of Example 117, 117g (10.0 mg, 0.0155 mmol) and o-nitroaniline (0.0766 mmol) afforded 4.8 mg (35%) of Example 136 as the TFA salt. MS (HR-ESI) calculated for $C_{38}H_{44}BF_3N_6O_7$ (M+H$^+$), found 765.3395.

Example 137

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-methyl-4-oxo-8-{2-oxo-2-[(2-phenyl-4-quinolinyl)amino]ethyl}-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and 2-phenylquinolin-4-amine (0.0766 mmol) afforded 2.8 mg (21%) of Example 137. MS (HR-ESI) calculated for $C_{47}H_{50}BF_3N_6O_5$ (M+H$^+$), found 770.3690.

Example 138

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-(2-{2-[(dimethylamino)carbonyl]anilino}-2-oxoethyl)-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and N,N-dimethyl-2-aminobenzamide (0.0766 mmol) afforded 7.0 mg (50%) of Example 138 as the TFA salt. MS (HR-ESI) calculated for $C_{41}H_{50}BF_3N_6O_6$ (M+H$^+$), found 791.3915.

Example 139

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-(2-{2-[(methylamino)carbonyl]anilino}-2-oxoethyl)-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and N-methyl-2-aminobenzamide (0.0766 mmol) afforded 7.4 mg (54%) of Example 139 as the TFA salt. MS (HR-ESI) calculated for $C_{40}H_{48}BF_3N_6O_6$ (M+H$^+$), found 777.3763.

Example 140

(6S,8S)-N-{(1R)-1-[(3aS,4S,6S,7aR)-Hexahydro-3a, 5,5-trimethyl-4,6-methano-1,3,2-benzodioxaborol-2-yl]propyl}-8-{2-[2-(aminocarbonyl)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide According to the procedure for the preparation of Example 117, 117g (10.0 mg, 0.0155 mmol) and 2-aminobenzamide (0.0766 mmol) afforded 7.4 mg (55%) of Example 140 as the TFA salt. MS (HR-ESI) calculated for $C_{39}H_{46}BF_3N_6O_6$ (M+H$^+$), found 763.3621.

TABLE 1

| Ex. | A$^3$ | R$^3$ | R$^{13}$ | R$^1$ | MS (M + H+) |
|---|---|---|---|---|---|
| 1 | Cbz-NH— | H | H | Allyl | 561.2905 |
| 2 | Cbz-NH— | H | H | Ethyl | 549.2867 |
| 3 | —NH$_2$ | H | H | Ethyl | 415.2497 |
| 4 | benzyl-NH— | H | H | Ethyl | 505.3010 |
| 5 | m-CF$_3$-benzyl-NH— | H | H | Ethyl | 573.2884 |
| 6 | phenyl-CONH— | H | H | Ethyl | 519.2773 |
| 7 | acetyl-NH— | H | H | Ethyl | 457.2606 |
| 8 | Cbz-NH— | Ph-propyl | H | Ethyl | 667.3674 |
| 9 | Cbz-NH— | H | Ph-propyl | Ethyl | 667.3660 |
| 10 | m-CF$_3$-benzyl-NH— | Ph-propyl | H | Ethyl | 691.3664 |
| 11 | m-CF$_3$-benzyl-NH— | H | Ph-propyl | Ethyl | 691.3667 |
| 116 | m-CF$_3$-benzyl-NH— | Me | Ph-propyl | Ethyl | 705.3808 |

TABLE 2

| Ex. | R$^4$ | R$^1$ | MS(M + H+) |
|---|---|---|---|
| 12 | benzyl | Ethyl | 706.3386 |
| 13 | phenyl | Ethyl | 720.3554 |
| 15 | 2-phenyl-4-quinolinyl | Ethyl | 833.3828 |
| 84 | 2-phenyl-4-quinolinyl | 2,2-diF-ethyl | 869.3645 |
| 124 | 4-benzyl-1-piperidinyl | Ethyl | 802.4321 |
| 125 | 4-(2-oxo-2,3-dihydro-1H-benzimidazol-1-yl)-1-piperidinyl | Ethyl | 844.4196 |
| 126 | 3-methyl-3-phenyl-piperidinyl | Ethyl | 802.4304 |
| 127 | 4-benzyl-4-hydroxy-1-piperidinyl | Ethyl | 818.4303 |
| 128 | 4-benzyl-1-piperazinyl | Ethyl | 803.4268 |
| 129 | 4-phenyl-1-piperazinyl | Ethyl | 789.4134 |
| 130 | 1-Benzyloxycarbonyl piperazinyl | Ethyl | 847.4175 |
| 131 | 3,4-dihydro-2(1H)-isoquinolinyl | Ethyl | 760.3851 |
| 132 | 4-(4-acetylphenyl)-1-piperazinyl | Ethyl | 831.4241 |

TABLE 3

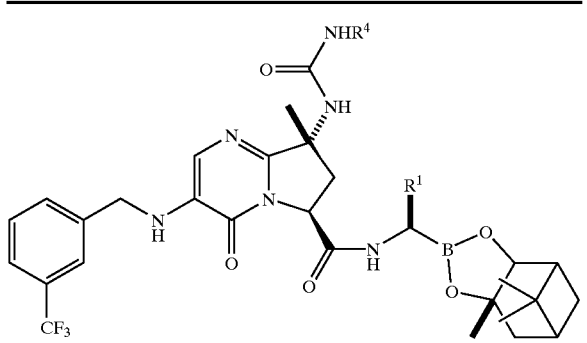

| Ex. | R⁴ | R¹ | MS(M + H+) |
|---|---|---|---|
| 16 | phenyl | Ethyl | 721.24 |
| 18 | 4-methoxyphenyl | Ethyl | 751.26 |
| 19 | 2-F-phenyl | Ethyl | 739.25 |
| 20 | 3-methoxyphenyl | Ethyl | 751.25 |
| 21 | 1-naphthyl | Ethyl | 771.29 |
| 22 | 3-cyanophenyl | Ethyl | 746.27 |
| 23 | 3-(acetyl)phenyl | Ethyl | 763.28 |
| 24 | 3-phenoxyphenyl | Ethyl | 813.31 |
| 25 | 4-(acetyl)phenyl | Ethyl | 763.28 |
| 26 | 2-naphthyl | Ethyl | 771.28 |
| 27 | Trans-2-phenylcyclopropyl | Ethyl | 761.22 |
| 28 | 2,4-diF-phenyl | Ethyl | 757.19 |
| 29 | 2,5-diF-phenyl | Ethyl | 757.20 |
| 30 | 2-methoxyphenyl | Ethyl | 751.25 |
| 31 | 2-CF₃-phenyl | Ethyl | 789.24 |
| 32 | 3-F-phenyl | Ethyl | 739.25 |
| 33 | 3-CF₃-phenyl | Ethyl | 789.25 |
| 34 | 4-F-phenyl | Ethyl | 739.26 |
| 35 | 4-CF₃-phenyl | Ethyl | 789.26 |
| 36 | 4-methylphenyl | Ethyl | 735.29 |
| 37 | 2,6-diisopropylphenyl | Ethyl | 805.37 |
| 38 | 2-(methoxycarbonyl)-phenyl | Ethyl | 779.28 |
| 39 | 2-(ethoxycarbonyl)-phenyl | Ethyl | 793.30 |
| 40 | 2-isopropylphenyl | Ethyl | 763.32 |
| 41 | 3,4,5,-trimethoxyphenyl | Ethyl | 811.31 |
| 42 | 3-(methylthio)phenyl | Ethyl | 767.25 |
| 43 | 3-(ethoxycarbonyl)-phenyl | Ethyl | 793.29 |
| 44 | 4-ethoxyphenyl | Ethyl | 765.29 |
| 45 | 4-(methylthio)phenyl | Ethyl | 767.26 |
| 46 | 4-isopropylphenyl | Ethyl | 763.32 |
| 47 | 4-ethylphenyl | Ethyl | 749.30 |
| 48 | 4-CF₃O-phenyl | Ethyl | 805.25 |
| 49 | phenethyl | Ethyl | 749.30 |
| 50 | 3-(methoxycarbonyl)-phenyl | Ethyl | 779.26 |
| 51 | 2-biphenyl | Ethyl | 797.30 |
| 52 | triphenylmethyl | Ethyl | 887.35 |
| 53 | 1-((R)-1-naphthyl)-ethyl | Ethyl | 799.31 |
| 54 | 1-((S)-phenyl)ethyl | Ethyl | 749.30 |
| 55 | isopropyl | Ethyl | 687.29 |
| 56 | 2-phenoxyphenyl | Ethyl | 813.27 |
| 57 | 2,6-diF-phenyl | Ethyl | 757.24 |
| 58 | 1-((R)-phenyl)ethyl | Ethyl | 749.29 |
| 59 | 4-isopropylphenyl | Ethyl | 763.30 |
| 60 | 4-(dimethylamino)-phenyl | Ethyl | 764.30 |
| 61 | 3,4-diCl-phenyl | Ethyl | 789.18 |
| 62 | 4-tert-butylphenyl | Ethyl | 777.31 |
| 63 | 2-((S)-3-methylbutyric acid methyl ester) | Ethyl | 759.29 |
| 64 | benzyl | Ethyl | 735.3 |

TABLE 3-continued

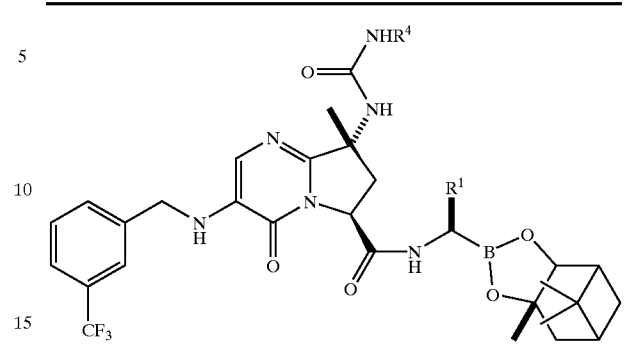

| Ex. | R⁴ | R¹ | MS(M + H+) |
|---|---|---|---|
| 66 | 2-(tert-butoxycarbonyl)phenyl | Ethyl | 821.9 |
| 67 | 2-benzoic acid | Ethyl | 765.7 |
| 68 | 2-Cl-phenyl | Ethyl | 755.3137 |
| 69 | 2,5-dimethoxyphenyl | Ethyl | 781.3710 |
| 70 | 2-methylphenyl | Ethyl | 735.3673 |
| 71 | 5-Cl-2,4-dimethoxyphenyl | Ethyl | 815.3341 |
| 72 | 2,4-dimethoxyphenyl | Ethyl | 781.3717 |
| 73 | 2-ethoxyphenyl | Ethyl | 765.3788 |
| 74 | 5-Cl-2-methoxyphenyl | Ethyl | 785.3208 |
| 75 | 2-(butoxycarbonyl)-phenyl | Ethyl | 821.4049 |
| 76 | 2-(methylthio)-phenyl | Ethyl | 815.3341 |
| 77 | 4-Cl-phenyl | Ethyl | 755.3106 |
| 78 | 4-F-2-nitrophenyl | Ethyl | 784.3261 |
| 79 | 5-isophthalate dimethyl ester | Ethyl | 837.3601 |
| 80 | 3-CF₃S-phenyl | Ethyl | 821.3110 |
| 81 | 4-(ethoxycarbonyl)-phenyl | Ethyl | 793.3718 |
| 82 | 2-nitrophenyl | Ethyl | 766.3362 |
| 83 | 2-aminophenyl | Ethyl | 734.4 |
| 85 | 2,5-dimethoxyphenyl | 2,2-diF-ethyl | 817.3539 |
| 86 | 5-Cl-2,4-dimethoxyphenyl | 2,2-diF-ethyl | 851.3153 |
| 87 | 2-(methoxycarbonyl)-phenyl | 2,2-diF-ethyl | 815.3370 |
| 88 | 2-(methylthio)phenyl | 2,2-diF-ethyl | 803.3181 |
| 89 | 2-ethoxyphenyl | 2,2-diF-ethyl | 801.3562 |
| 90 | 5-Cl-2-methoxyphenyl | 2,2-diF-ethyl | 821.3013 |
| 91 | 2-(ethoxycarbonyl)-phenyl | 2,2-diF-ethyl | 829.3534 |
| 117 | phenyl | Ethyl | 720.3553 |
| 118 | benzyl | Ethyl | 734.3704 |
| 119 | 1-isoquinolinyl | Ethyl | 771.3679 |
| 120 | 2-methoxy-phenyl | Ethyl | 750.3679 |
| 121 | 2-(methoxycarbonyl)-phenyl | Ethyl | 778.3575 |
| 122 | 3-pyridinyl | Ethyl | 721.3480 |
| 123 | 2-(hydroxymethyl)phenyl | Ethyl | 750.3657 |
| 133 | 3-(methylsulfanyl)phenyl | Ethyl | 766.3443 |
| 134 | 2-methyl-4-quinolinyl | Ethyl | 785.3803 |
| 135 | 1-naphthyl | Ethyl | 770.3690 |
| 136 | 2-nitrophenyl | Ethyl | 765.3395 |
| 137 | (2-phenyl-4-quinolinyl) | Ethyl | 770.3690 |
| 138 | 2-((dimethylamino) carbonyl) phenyl | Ethyl | 791.3915 |
| 139 | 2-((methylamino)carbonyl) phenyl | Ethyl | 777.3763 |
| 140 | 2-(aminocarbonyl)phenyl | Ethyl | 763.3621 |

TABLE 4

| Ex. | R⁴ | R¹ | MS(M + H+) |
|---|---|---|---|
| 17 | benzyl | Ethyl | 749.3461 |
| 65 | p-Cl-benzyl | Ethyl | 783.5 |

TABLE 5

| Ex. | R³ | R⁴ | R¹ | MS(M + H+) |
|---|---|---|---|---|
| 93 | Me | phenyl | Ethyl | 720.6 |
| 94 | Me | 4-nitrophenyl | Ethyl | 765.6 |
| 95 | Me | 2-pyridinyl | Ethyl | 721.6 |
| 96 | Me | 1-naphthyl | Ethyl | 829.3534 |
| 97 | Me | 3-methoxyphenyl | Ethyl | 750.3642 |
| 98 | Me | 5-quinolinyl | Ethyl | 771.3670 |
| 99 | Me | 2-methyl-6-quinolinyl | Ethyl | 785.3815 |
| 100 | Me | 3-pyridinyl | Ethyl | 721.3490 |
| 101 | Me | 1-isoquinolinyl | Ethyl | 771.3655 |
| 102 | Me | 2-quinolinyl | Ethyl | 771.3669 |
| 103 | Me | 2-methoxyphenyl | Ethyl | 750.3672 |
| 104 | Me | (1,1')-biphenyl)4-yl | Ethyl | 796.3858 |
| 105 | Me | 4-(methoxycarbonyl)phenyl | Ethyl | 778.3605 |
| 106 | Me | benzyl | Ethyl | 734.3714 |
| 107 | Me | 4-(hydroxymethyl)phenyl | Ethyl | 750.3664 |
| 108 | Me | 4-(dimethylamino)phenyl | Ethyl | 763.3995 |
| 109 | Me | 4-tert-butylphenyl | Ethyl | 776.4190 |
| 110 | Me | 3-(trifluoromethyl)phenyl | Ethyl | 788.3429 |
| 111 | Me | 4-(benzyloxy)phenyl | Ethyl | 826.3974 |
| 114 | H* | phenyl* | Ethyl | 706.3389 |
| 115 | H* | phenyl* | Ethyl | 706.3373 |

*C8 stereochemistry not determined.

TABLE 6

| Ex. | R³ | R⁴ | R¹ | MS(M + H+) |
|---|---|---|---|---|
| 14 | Me | phenyl | Ethyl | 722.3365 |
| 92 | Me | tert-butyl* | Ethyl | 687.3549 |
| 112 | H* | tert-butyl* | Ethyl | 687.3549 |
| 113 | H* | tert-butyl* | Ethyl | 687.3552 |

*C8 stereochemistry not determined.

Utility

The compounds of Formula (I) are expected to inhibit the activity of Hepatitis C Virus NS3 protease and, therefore, to possess utility in the cure and prevention of HCV infections. The NS3 protease inhibition is demonstrated using assays for NS3 protease activity, for example, using the assay described below for assaying inhibitors of NS3 protease. The compounds of Formula (I) are expected to show activity against NS3 protease in cells, as demonstrated by the cellular assay described below. A compound is considered to be active if it has an $IC_{50}$ value of less than about 100 $\mu$M in this assay. It is more preferred if it has an $IC_{50}$ value of less than about 60 $\mu$M. It is even more preferred if it has an $IC_{50}$ value of less than about 1 $\mu$M. It is most preferred if it has an $IC_{50}$ value of less than about 0.1 $\mu$M. Compounds of the present invention have been shown to have an $IC_{50}$ value of less than about 100 $\mu$M in this assay.

Expression and Purification of NS3 Protease

The plasmid cf1SODp600, containing the complete coding region of HCV NS3 protease, genotype 1a, was obtained from ATCC (database accession: DNA Seq. Acc. M62321, originally deposited by Chiron Corporation). PCR primers were designed that allow amplification of the DNA fragment encoding the NS3 protease catalytic domain (amino acids 1 to 192) as well as its two N-terminal fusions, a 5 amino acid leader sequence MGAQH (serving as a expression tag) and a 15 amino acid His tag MRGSHHHHHHMGAQH. The NS3 protease constructs were cloned in the bacterial expression vector under the control of the T7 promoter and transformed in *E. coli* BL 21 (DE3) cells. Expression of the NS3 protease was obtained by addition of 1 mM IPTG and cells were growing for additional 3 h at 25° C. The NS3 protease constructs have several fold difference in expression level, but exhibit the same level of solubility and enzyme specific activity. A typical 10 L fermentation yielded approximately 200 g of wet cell paste. The cell paste was stored at −80° C. The NS3 protease was purified based on published procedures (Steinkuhler C. et al. *Journal of Virology* 70, 6694–6700, 1996 and Steinkuhler C. et al. *Journal of Biological Chemistry* 271, 6367–6373, 1996.) with some modifications. Briefly, the cells were resuspended in lysis buffer (10 mL/g) containing PBS buffer (20 mM sodium phosphate, pH 7.4, 140 mM NaCl), 50% glycerol, 10 mM DTT, 2% CHAPS and 1 mM PMSF. Cell lysis was performed with use of microfluidizer. After homogenizing, DNase was added to a final concentration 70 U/mL and cell lysate was incubated at 4° C. for 20 min. After centrifugation at 18,000 rpm for 30 min at 4° C. supernatant was applied on SP Sepharose column (Pharmacia), previously equilibrated at a flow rate 3 mL/min in buffer A (PBS buffer, 10% glycerol, 3 mM DTT). The column was extensively washed with buffer A and the protease was eluted by applying 25 column volumes of a linear 0.14–1.0 M NaCl gradient. NS3 containing fractions were pooled and concentrated on an Amicon stirred ultrafiltration cell using a YM-10 membrane. The enzyme was further purified on 26/60 Superdex 75 column (Pharmacia), equilibrated in buffer A. The sample was loaded at a flow rate 1 mL/min, the column was then washed with a buffer A at a flow rate 2 mL/min. Finally, the NS3 protease containing fractions were applied on Mono S 10/10 column (Pharmacia) equilibrated in 50 mM Tris.HCl buffer, pH 7.5, 10% glycerol and 1 mM DTT and operating at flow rate 2 mL/min. Enzyme was eluted by applying 20 column volumes of a linear 0.1–0.5 M NaCl gradient. Based on SDS-PAGE analysis as well as HPLC analysis and active site titration, the purity of the HCV NS3 1a protease was greater than 95%. The enzyme was stored at −70° C. and diluted just prior to use.

Enzyme Assays

Concentrations of protease were determined in the absence of NS4a by using the peptide ester substrate Ac-DED (Edans)EEAbuψ[COO]ASK(Dabcyl)-NH$_2$ (Taliani et al. *Anal. Biochem.* 240, 60–67, 1996.) and the inhibitor, H-Asp-Glu-Val-Val-Pro-boroAlg-OH (administered as a hydrolyzed compound to the boronic acid), and by using tight binding reaction conditions (Bieth, *Methods Enzymol.* 248, 59–85, 1995). Best data was obtained for an enzyme level of 50 nM. Alternately, protease (63 μg/mL) was allowed to react with 3 μM NS4a, 0.10 mM Ac-Glu-Glu-Ala-Cys-pNA, and varying level of H-Asp-Glu-Val-Val-Pro-boroAlg-OH (0–6 μM). Concentrations of protease were determined from linear plots of Activity vs. [inhibitor]. Molar concentrations of proteases were determined from the x-intercept.

$K_m$ values were determined measuring the rate of hydrolysis of the ester substrate over a range of concentrations from 5.0 to 100 μM in the presence of 3 μM KKNS4a (KKGSVVIVGRIVLSGKPAIIPKK). Assay were run at 25° C., by incubating ~1 nM enzyme with NS4a for 5 min in 148 μL of buffer (50 mM Tri buffer, pH 7.0, 50% glycerol, 2% Chaps, and 5.0 mM DTT. Substrate (2.0 μL) in buffer was added and the reaction was allowed to proceed for 15 min. Reactions were quenched by adding 3.0 μL of 10% TFA, and the levels of hydrolysis were determined by HPLC. Aliquots (50 μL) were injected on the HPLC and linear gradients from 90% water, 10% acetonitrile and 0.10% TFA to 10% water, 90% acetonitrile and 0.10% TFA were run at a flow rate of 1.0 mL/min over a period of 30 min. HPLCs were run on a HP1090 using a Rainin 4.6×250 mm C18 column (cat #83-201-C) fluorescent detection using 350 and 500 nm as excitation and emission wavelengths, respectively. Levels of hydrolysis were determined by measuring the area of the fluorescent peak at 5.3 min. 100% hydrolysis of a 5.0 μM sample gave an area of 7.95±0.38 fluorescence units.). Kinetic constants were determined from the iterative fit of the Michaelis equation to the data. Results are consistent with data from Liveweaver Burk fits and data collected for the 12.8 min peak measured at 520 nm.

Enzyme activity was also measured by measuring the increase in fluorescence with time by exciting at 355 nm and measuring emission at 495 nm using a Perkin Elmer LS 50 spectrometer. A substrate level of 5.0 μM was used for all fluorogenic assays run on the spectrometer.

Inhibitor Evaluation In vitro

Inhibitor effectiveness was determined by measuring enzyme activity both in the presence and absence of inhibitor. Velocities were fit to the equation for competitive inhibition for individual reactions of inhibitors with the enzyme using $$v_i/v_o = [K_m(1+I/K_i)+S]/[K_m+S].$$

The ratio $v_i/v_o$ is equal to the ratio of the Michaelis equations for velocities measured in the presence ($v_i$) and absence ($v_o$) of inhibitor. Values of $v_i/v_o$ were measured over a range of inhibitor concentrations with the aid of an Excel™ Spreadsheet. Reported $K_i$ values are the average of 3–5 separate determinations. Under the conditions of this assay, the $IC_{50}$ and $K_i$s are comparable measures of inhibitor effectiveness.

Using the methodology described above, a number of compounds of the present invention were found to exhibit a $K_i$ of ≦60 μM, thereby confirming the utility of the compounds of the present invention as effective NS3 protease inhibitors.

Inhibitor Evaluation in Cell Assay

The following method was devised to assess inhibitory action of test compounds on the HCV NS3 protease in cultured cells. Because it is not possible to efficiently infect cells with hepatitis C virus, an assay was developed based on co-expression in transfected cell lines of two plasmids, one is able to direct synthesis of the NS3 protease and the other to provide a polypeptide analogous to a part of the HCV non-structural protein containing a single known peptide sequence highly susceptible to cleavage by the protease. When installed in cultured cells by one of a variety of standard methods, the substrate plasmid produces a stable polypeptide of approximately 50KD, but when the plasmid coding for the viral protease is co-expressed, the enzymatic action of the protease hydrolyzes the substrate at a unique sequence between a cysteine and a serine pair, yielding products which can be detected by antibody-based technology, eg, a western blot. Quantitation of the amounts of precursor and products can be done by scanning film auto-radiograms of the blots or direct luminescense-based emissions from the blots in a commercial scanning device. The general organization of the two plasmids is disclosed in a PCT application PCT/US00/18655. The disclosure of which is hereby incorporated by reference. The coding sequences for the NS3 protease and the substrate were taken from genotype 1a of HCV, but other genotypes, eg 2a, may be substituted with similar results.

The DNA plasmids are introduced into cultured cells using electroporation, liposomes or other means. Synthesis of the protease and the substrate begin shortly after introduction and may be detected within a few hours by immunological means. Therefore, test compounds are added at desired concentrations to the cells within a few minutes after introducing the plasmids. The cells are then placed in a standard $CO_2$ incubator at 37° C., in tissue culture medium eg Dulbecco-modified MEM containing 10% bovine serum. After 6–48 hours, the cells are collected by physically scraping them from plastic dishes in which they have been growing, centrifuging them and then lysing about $10^6$ of the concentrated cells in a minimal volume of buffered detergent, eg 20 μL of 1% sodium dodecyl sulfate in 0.10 M Tris-HCl, pH 6.5, containing 1% mercaptaethanol and 7% glycerol. The samples are then loaded onto a standard SDS polyacrylamide gel, the polypeptides separated by electrophoresis, and the gel contents then electroblotted onto nitrocellulose or other suitable paper support, and the substrate and products detected by decoration with specific antibodies.

Preparation of H-Asp-Glu-Val-Val-Pro-boroAlg pinanediol ester.trifluoroacetate

Preparation of Boc-Asp(O'Bu)-Glu(O'Bu)-Val-Val-Pro-OH

Boc-Val-Pro-OBzl was prepared by dissolving H-Pro-OBzl (20 g, 83 mmol) in 50 mL of chloroform and adding Boc-Val-OH (18.0 g, 83 mmol), HOBt (23.0 g, 165 mmol), NMM (9.0 mL, 83 mmol) and DCC (17.0 g, 83 mmol). The reaction mixture was stirred overnight at room temperature. The mixture was filtered and solvent was evaporated. Ethyl acetate was added and insoluble material was removed by filtration. The filtrate was washed with 0.2N HCl, 5% NaHCO$_3$, and saturated aqueous NaCl. It was dried over Na$_2$SO$_4$, filtered and evaporate to give a white solid (30 g, 75 mmol, 90%). ESI/MS calculated for $C_{22}H_{32}N_2O_5$ +H: 405.2. Found 405.6.

Boc-Val-Val-Pro-OBzl was prepared by dissolving Boc-Val-Pro-OBzl (14.0 g, 35.0 mmol) in 4N HCl in dioxane (20 mL) and allowing the reaction to stir for 2 h under an inert atmosphere at room temperature. The reaction mixture was concentrated by evaporation in vacuo and ether was added to yield a precipitate. It was collected by filtration under nitrogen. After drying in vacuo with P$_2$O$_5$, H-Val-Pro-OBzl was obtained as a white solid (22.6 g, 30.3 mmol, 89%). (ESI/MS calculated for $C_{17}H_{24}N_2O_3$ +H: 305.2. Found: 305.2.) H-Val-Pro-OBzl (9.2 g, 27 mmol) was dissolved in 50 mL of CH$_2$Cl$_2$ and Boc-Val-OH (7.3 g, 27 mmol), HOBt (7.3 g, 54 mmol), NMM (3.0 mL, 27 mmol) and DCC (5.6 g, 27 mmol) were added. The reaction mixture stirred overnight at room temperature. The mixture was filtered and the filtrate was evaporated. The residue was dissolved in ethyl acetate and the solution was re-filtered. The filtrate was washed with 0.2N HCl, 5% NaHCO$_3$, and saturated aqueous NaCl. It was dried over Na$_2$SO$_4$, filtered and evaporated to give a yellow oil (10.6 g, 21.1 mmol, 78%). ESI/MS calculated for $C_{27}H_{41}N_3O_6$+Na: 526.3 Found: 526.4.

Z-Glu(O'Bu)-Val-Val-Pro-OBzl was also prepared by DCC coupling. H-Val-Val-Pro-OBzl.hydrochloride was obtained in a 100% yield by treating the corresponding Boc compound with anhydrous HCl using the procedure described for H-Val-Pro-OBzl (ESI/MS calculated for $C_{22}H_{33}N_3O_4$+H: 404.2. Found 404.3.). The amine hydrochloride (7.40 g, 16.8 mmol) was dissolved in 185 mL DMF and 25 mL THF. Z-Glu(O'Bu)-OH (5.60 g, 16.8 mmol), HOBt (4.60 g, 33.6 mmol), NMM (1.85 mL, 16.8 mmol) and DCC (3.5 g, 16.8 mmol) were added. The reaction was run and the product was isolated by the procedure described for Boc-Val-Val-Pro-OBzl. The tetrapeptide was obtained as a white foam (12.0 g, 16.1 mmol, 96%). ESI/MS calculated for $C_{39}H_{54}N_4O_9$+Na: 745.4. Found: 745.4.

H-Glu(O'Bu)-Val-Val-Pro-OH was prepared by dissolving Z-Glu(O'Bu)-Val-Val-Pro-OBzl (2.90 g, 3.89 mmol) in 100 mL methanol containing 1% acetic acid. Pearlman's catalyst, Pd(OH)$_2$, (100 mg) was added and the flask was placed on the Parr hydrogenation apparatus with an initial H$_2$ pressure of 34 psi. After three hours, the catalyst was removed by filtration through a celite pad and the filtrate was evaporated in vacuo to yield a yellow oil (1.30 g, 2.61 mmol, 67%). ESI/MS calculated for $C_{24}H_{42}N_4O_7$+H: 499.3 Found: 499.4.

Boc-Asp(O'Bu)-Glu(O'Bu)-Val-Val-Pro-OH was prepared by active ester coupling. Boc-Asp(O'Bu)-N-hydroxysuccinimide ester was prepared by coupling Boc-Asp(OtBu)-OH (3.00 g, 10.4 mmol) to N-hydroxysuccinimide (1.19 g, 10.4 mmol) in 50 mL of ethylene glycol dimethyl ether. The reaction flask was placed in an ice bath at 0° C. and DCC was added. The reaction mixture was slowly allowed to warm to room temperature and to stir overnight. The mixture was filtered and the filtrate was evaporated in vacuo. The residue was dissolved in ethyl acetate and re-filtered. The filtrate was evaporated give a white solid. Recrystallized from ethyl acetate: hexane gave the activated ester (3.38 g, 8.80 mmol, 84%). (ESI/MS calculated for $C_{17}H_{26}N_2O_8$+H: 387.2. Found: 387.4.)H-Glu(O'Bu)-Val-Val-Pro-OH (5.40 g, 10.8 mmol) was dissolved in 100 mL of water. Sodium bicarbonate (0.92 g, 11.0 mmol) was added followed by triethylamine (2.30 mL, 16.5 mmol). The N-hydroxysuccinimide ester (3.84 g, 10.0 mmol) was dissolved in 100 mL dioxane and was added to the H-Glu(O'Bu)-Val-Val-Pro-OH solution. The mixture stirred overnight at room temperature. Dioxane was removed in vacuo and 1.0 M HCl was added to give pH~1. The product was extracted into ethyl acetate. The ethyl acetate solution was washed with 0.2 N HCl, dried over sodium sulfate, filtered, and evaporated to yield a yellow oil (7.7 g, 10.0 mmol, 100%). ESI/MS calculated for $C_{37}H_{63}N_5O_{12}$+Na: 792.4. Found: 792.4.

Boc-Asp(O'Bu)-Glu(O'Bu)-Val-Val-Pro-boroAlg-pinanediol was prepared by coupling the protected pentapeptide to H-boroAlg-pinanediol. Boc-Asp(O'Bu)-Glu(O'Bu)-Val-Val-Pro-OH (1.8 g, 2.3 mmol) was dissolved 10 mL THF and was cooled to −20° C. Isobutyl chloroformate (0.30 mL, 2.3 mmol) and NMM (0.25 mL, 2.3 mmol) were added. After 5 minutes, this mixture was added to H-boroAlg-pinanediol (0.67 g, 2.3 mmol) dissolved in THF (8 mL) at −20° C. Cold THF (~5 mL) was used to aid in the transfer. Triethylamine (0.32 mL, 2.3 mmol) was added and the reaction mixture was allowed to come to room temperature and to stir overnight. The mixture was filtered and solvent was removed by evaporation. The residue was dissolved in ethyl acetate, washed with 0.2 N HCl, 5% NaHCO$_3$, and saturated NaCl. The organic phase was dried with Na$_2$SO$_4$, filtered, and evaporated to yield a yellow oil. Half of the crude product (1.5 g) was purified in 250 mg lots by HPLC using a 4 cm×30 cm Rainin C-18 reverse phase column. A gradient from 60: 40 acetonitrile: water to 100% acetonitrile was run over a period of 28 minutes at a flow rate of 40 mL/min. The fractions containing the desired product were pooled and lyophilized to yield a white solid (46 mg). $^1$H-NMR (CD$_3$OD) δ0.9–1.0 (m, 15H), 1.28 (s, 3H), 1.3 (s,3H), 1.44 (3s, 27H), 1.6–2.8 (20H), 3.7(m,1H), 3.9(m, 1H), 4.1–4.7 (7H), 5.05(m, 2H), 5.9(m, 1H). High res (ESI/MS) calculated for $C_{51}H_{86}N_6O_{13}B_1$+H: 1001.635. Found 1001.633.

Preparation of H-Asp-Glu-Val-Val-Pro-boroAlg pinanediol ester.trifluoroacetate: The hexapeptide analog, Boc-Asp(O'Bu)-Glu(O'Bu)-Val-Val-Pro-boroAlg-pinanediol, (22.5 mg, 0.023 mmol) was treated with 2 mL of TFA: CH$_2$Cl$_2$ (1:1) for 2 h. The material was concentrated in vacuo and purified by HPLC using C-18 Vydac reverse phase (2.2×25 cm) column with a gradient starting at 60:40 acetonitrile/water with 0.1%TFA going to 95:5 over 25 minutes with a flow rate of 8 mL/min. The product eluted at 80% acetonitrile. The fractions were evaporated and dried under high vacuum to give 8.9 mg (49%) of the desired product as white amorphous solid. $^1$H-NMR (CD$_3$OD) δ5.82 (m, 1H), 5.02 (m, 2H), 4.58(m, 1H), 4.42 (m, 3H), 4.18 (m, 4H), 3.90 (m, 1H), 3.62 (m, 1H), 3.01 (dd, 1H), 2.78 (m, 1H), 2.62 (m, 1H), 2.41–1.78 (m, 17H), 1.31 (s, 3H), 1.28 (s, 3H), 1.10–0.82 (m, 15H). ESI/MS calculated for $C_{38}H_{62}N_6O_{11}B$+H: 789.2. Found: 789.2.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

Dosage and Formulation

The HCV protease inhibitor compounds of this invention can be administered as treatment for the control or prevention of hepatitis C virus infections by any means that produces contact of the active agent with the agent's site of action, i.e., the NS3 protease, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

What is claimed is:

1. A compound of Formula (I):

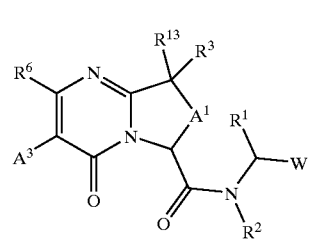

or a stereoisomer, or pharmaceutically acceptable salt form, wherein:

$A^1$ is —$CH_2$— or —$CH_2CH_2$—;

$A^3$ is H, —C(=O)$R^{9a}$, —O$R^{9a}$, —S$R^{9a}$, —S(=O)$R^{9a}$, —S(=O)$_2R^{9a}$, —NHCO$R^{9a}$, —CONH$R^{9a}$, —NHS (=O)$_2$R$^{9a}$, —S(=O)$_2$NHR$^{9a}$, —NHC(=O)OR$^{9a}$, —OC(=O)NHR$^{9a}$, —C(=O)OR$^{9a}$, —O—C(=O)R$^{9a}$, —NR$^8$R$^{9a}$; —NH—A$^4$—R$^{9b}$; or —NH—A$^4$—A$^5$—R$^{9b}$;

W is —B(OR$^{26}$)(OR$^{27}$);

R$^1$ is selected from the group: H; C$_1$–C$_4$ alkyl substituted with 0–2 R$^{1a}$; C$_2$–C$_4$ alkenyl substituted with 0–2 R$^{1a}$; and C$_2$–C$_4$ alkynyl substituted with 0–2 R$^{1a}$;

R$^{1a}$ is selected at each occurrence from the group: Cl, F, Br, CF$_3$, CHF$_2$, OH, C$_3$–C$_6$ cycloalkyl, C$_1$–C$_6$ alkoxy, —S—(C$_1$–C$_6$ alkyl); C$_1$–C$_4$ alkyl substituted with 0–2 R$^{1c}$; aryl substituted with 0–3 R$^{1c}$; and 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 R$^{1c}$;

R$^{1c}$ is selected at each occurrence from the group: C$_1$–C$_4$ alkyl, Cl, F, Br, I, OH, SH, —CN, —NO$_2$, —OR$^{1d}$, —C(=O)OR$^{1d}$, —NR$^{1d}$R$^{1d}$, —SO$_2$R$^{1d}$, —SO$_3$R$^{1d}$, —C(=O)NHR$^{1d}$, —NHC(=O)R$^{1d}$, —SO$_2$NHR$^{1d}$, —CF$_3$, —OCF$_3$, C$_3$–C$_6$ cycloalkyl, phenyl, and benzyl;

R$^{1d}$ is selected at each occurrence from the group: H, C$_1$–C$_4$ alkyl, phenyl and benzyl;

R$^2$ is H;

R$^3$ is selected from the group: R$^4$, —(CH$_2$)$_p$—NH—R$^4$, —(CH$_2$)$_p$—NHC(=O)—R$^4$, —(CH$_2$)$_p$—C(=O)NH—R$^4$, —(CH$_2$)$_p$—C(=O)O—R$^4$, —(CH$_2$)$_p$—NHC(=O)NH—R$^4$, —(CH$_2$)$_p$—NHC(=O)NHC(=O)—R$^4$, —(CH$_2$)$_p$—C(=O)—R$^4$, —(CH$_2$)$_p$—O—R$^4$, and —(CH$_2$)$_p$—S—R$^4$;

p is 0, 1, or 2;

R$^4$ is selected from the group: C$_1$–C$_4$ alkyl substituted with 0–3 R$^{4a}$; C$_2$–C$_4$ alkenyl substituted with 0–3 R$^{4a}$; C$_2$–C$_4$ alkynyl substituted with 0–3 R$^{4a}$; C$_3$–C$_6$ cycloalkyl substituted with 0–2 R$^{4b}$; aryl substituted with 0–5 R$^{4b}$; and 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–4 R$^{4b}$;

R$^{4a}$ is, at each occurrence, independently selected from: H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O)R$^{11a}$, —SO$_2$R$^{11}$, —SO$_2$N$^{11}$R$^{11a}$, —NHC(=NH)NHR$^{11}$, —C(=NH)NHR$^{11}$, =NOR$^{11}$, —NR$^{11}$C(=O)OR$^{11a}$, —NR$^{11}$C(=O)NR$^{11}$R$^{11a}$, —NR$^{11}$SO$_2$NR$^{11}$R$^{11a}$, —NR$^{11}$SO$_2$R$^{11a}$; C$_1$–C$_4$ alkyl substituted with 0–2 R$^{4b}$; C$_2$–C$_4$ alkenyl substituted with 0–2 R$^{4b}$; C$_2$–C$_4$ alkynyl substituted with 0–2 R$^{4b}$; C$_3$–C$_7$ cycloalkyl substituted with 0–3 R$^{4c}$; aryl substituted with 0–5 R$^{4c}$; and 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 R$^{4c}$;

R$^{4b}$ is, at each occurrence, independently selected from: H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11a}$, —NHC(=NH)NHR$^{11}$, —C(=NH)NHR$^{11}$, =NOR$^{11}$, —NR$^{11}$C(=O)OR$^{11a}$, —OC(=O)NR$^{11}$R$^{11a}$, —NR$^{11}$C(=O)NR$^{11}$R$^{11a}$, —NR$^{11}$SO$_2$NR$^{11}$R$^{11a}$, —NR$^{11}$SO$_2$R$^{11a}$, —OP(O)(OR$^{11}$)$_2$; C$_1$–C$_4$ alkyl substituted with 0–3 R$^{4c}$; C$_2$–C$_4$ alkenyl substituted with 0–3 R$^{4c}$; C$_2$–C$_4$ alkynyl substituted with 0–3 R$^{4c}$; C$_3$–C$_6$ cycloalkyl substituted with 0–4 R$^{4d}$; aryl substituted with 0–5 R$^{4d}$; and 5–10 membered heterocyclic group consisting of carbon atoms and 1–4 heteroatoms selected from the group: O, S, and N; optionally saturated or unsaturated; and said 5–10 membered heterocyclic group is substituted with 0–3 R$^{4d}$;

R$^{4c}$ is, at each occurrence, independently selected from: H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11a}$, C$_1$–C$_4$ haloalkyl, C$_1$–C$_4$ haloalkoxy; C$_1$–C$_4$ alkyl substituted with 0–3 R$^{4d}$; C$_2$–C$_4$ alkenyl substituted with 0–3 R$^{4d}$; C$_2$–C$_4$ alkynyl substituted with 0–3 R$^{4d}$; C$_3$–C$_6$ cycloalkyl substituted with 0–4 R$^{4d}$; aryl substituted with 0–5 R$^{4d}$; and 5–10 membered heterocyclic group consisting of carbon atoms and 1–4 heteroatoms selected from the group: O, S, and N; optionally saturated or unsaturated; and said 5–10 membered heterocyclic group is substituted with 0–3 R$^{4d}$;

R$^{4d}$ is, at each occurrence, independently selected from: H, F, Cl, Br, I, —NO$_2$, —CN, —NCS, —CF$_3$, —OCF$_3$, =O, OH, —CO$_2$H, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11a}$, C$_1$–C$_4$ alkyl, C$_1$–C$_4$ alkoxy, C$_1$–C$_4$ haloalkyl, C$_1$–C$_4$ haloalkoxy, phenyl, and benzyl;

R$^6$ is H or C$_{11}$–C$_6$ alkyl;

R$^8$ is H, methyl, ethyl, propyl, or butyl;

R$^{9a}$ is selected from the group: H; C$_1$–C$_4$ alkyl substituted with 0–2 R$^{9c}$; C$_2$–C$_4$ alkenyl substituted with 0–2 R$^{9c}$; C$_2$–C$_4$ alkynyl substituted with 0–2 R$^{9c}$; C$_3$–C$_6$ cycloalkyl substituted with 0–2 R$^{9d}$; phenyl substituted with 0–3 R$^{9d}$; and 5–6 membered heterocyclic group consisting of carbon atoms and 1–4 heteroatoms selected from the group: O, S, and N; optionally saturated, partially unsaturated or unsaturated; and said heterocyclic group is substituted with 0–3 R$^{9d}$;

R$^{9b}$ is selected from the group: H, —S(=O)R$^{11}$, —S(=O)$_2$R$^{11}$, —S(=O)$_2$NHR$^{11}$, —C(=O)R$^{11}$, —C(=O)OR$^{11}$, —C(=O)NHR$^{11}$; —C(=O)NHC(=O)R$^{11}$; C$_1$–C$_4$ alkyl substituted with 0–2 R$^{9c}$; C$_2$–C$_4$ alkenyl substituted with 0–2 R$^{9c}$; C$_2$–C$_4$ alkynyl substituted with 0–2 R$^{9c}$; C$_3$–C$_6$ cycloalkyl substituted with 0–2 R$^{9d}$; aryl substituted with 0–5 R$^{9d}$; and 5–10 membered heterocyclic group consisting of carbon atoms and 1–4 heteroatoms selected from the group: O, S, and N; optionally saturated, partially unsaturated or unsaturated; and said 5–10 membered heterocyclic group is substituted with 0–3 R$^{9d}$;

R$^{9c}$ is selected from the group: CF$_3$, OCF$_3$, Cl, F, Br, OH, C(O)OR$^{11}$, NH$_2$, NH(CH$_3$), N(CH$_3$)$_2$, —CN, NO$_2$, phenyl and benzyl;

R$^{9d}$ is selected at each occurrence from the group: CF$_3$, OCF$_3$, Cl, F, Br, OH, C(O)OR$^{11}$, NH$_2$, NH(CH$_3$), N(CH$_3$)$_2$, —CN, NO$_2$; C$_1$–C$_4$ alkyl substituted with 0–1 R$^{9e}$, C$_1$–C$_4$ alkoxy substituted with 0–1 R$^{9e}$, C$_3$–C$_6$ cycloalkyl substituted with 0–1 R$^{9e}$, phenyl substituted with 0–3 $R^{9e}$, and 5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–3 $R^{9e}$;

$R^{9e}$ is selected at each occurrence from the group: $C_1$–$C_4$ alkyl, $C_1$–$C_4$ alkoxy, $CF_3$, $OCF_3$, Cl, F, Br, OH, phenyl, $C(O)OR^{11}$, $NH_2$, $NH(CH_3)$, $N(CH_3)_2$, —CN, and $NO_2$;

$R^{11}$ and $R^{11a}$ are, at each occurrence, independently selected from the group: H, $C_1$–$C_4$ alkyl substituted with 0–1 $R^{11b}$, phenyl substituted with 0–2 $R^{11b}$; and benzyl substituted with 0–2 $R^{11b}$;

$R^{11b}$ is OH, $C_1$–$C_4$ alkoxy, F, Cl, Br, I, $NH_2$, or —NH ($C_1$–$C_4$ alkyl);

$R^{13}$ is selected from the group: H, $C_1$–$C_4$ alkyl, $C_2$–$C_4$ alkenyl, $C_2$–$C_4$ alkynyl, $C_3$–$C_6$ cycloalkyl, $C_3$–$C_6$ cycloalkyl($C_1$–$C_4$ alkyl), aryl and aryl-$C_1$–$C_4$ alkyl;

$OR^{26}$ and $OR^{27}$ are independently selected from: a)-OH, d) $C_1$–$C_8$ alkoxy, and when taken together, $OR^{26}$ and $OR^{27}$ form: e) a cyclic boronic ester where said cyclic boronic ester contains from 2 to 16 carbon atoms;

$A^4$ and $A^5$ are independently selected from an amino acid residue wherein said amino acid residue, at each occurence, is independently selected from the group: Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O$^t$Bu), Glu(O$^t$Bu), Hyp(O$^t$Bu), Thr (O$^t$Bu), Asp(OBzl), Glu(OBzl), Hyp(OBzl), Pro (OBzl), Thr(OBzl), cyclohexylglycine, cyclohexylalanine, cyclopropylglycine, t-butylglycine, phenylglycine, and 3,3-diphenylalanine.

2. A compound of claim 1, or a stereoisomer, or pharmaceutically acceptable salt form wherein:

$A^1$ is —$CH_2$—;

$A^3$ is H, —$NHCOR^{9a}$, —$CONHR^{9a}$, —NHC(=O)O$R^{9a}$, —$NR^8R^{9a}$; or —NH—$A^4$—$R^{9b}$;

W is —$B(OR^{26})(OR^{27})$;

$R^1$ is selected from the group: H; $C_1$–$C_4$ alkyl substituted with 0–2 $R^{1a}$; $C_2$–$C_4$ alkenyl substituted with 0–2 $R^{1a}$; and $C_2$–$C_4$ alkynyl substituted with 0–2 $R^{1a}$;

$R^{1a}$ is selected at each occurrence from the group: Cl, F, Br, $CF_3$, and $CHF_2$;

$R^2$ is H;

$R^3$ is selected from the group: $R^4$, —$(CH_2)_p$—NH—$R^4$, —$(CH_2)_p$—NHC(=O)—$R^4$, —$(CH_2)_p$—C(=O) NH—$R^4$, —$(CH_2)_p$—C(=O)O—$R^4$, —$(CH_2)_p$—NHC(=O)NH—$R^4$, —$(CH_2)_p$—NHC(=O)NHC (=O)—$R^4$, —$(CH_2)_p$—C(=O)—$R^4$, —$(CH_2)_p$—O—$R^4$, and —$(CH_2)_p$—S—$R^4$;

p is 0 or 1;

$R^4$ is selected from the group: $C_1$–$C_4$ alkyl substituted with 0–3 $R^{4a}$; $C_2$–$C_4$ alkenyl substituted with 0–3 $R^{4a}$; $C_2$–$C_4$ alkynyl substituted with 0–3 $R^{4a}$; $C_3$–$C_6$ cycloalkyl substituted with 0–2 $R^{4b}$; phenyl substituted with 0–3 $R^{4b}$; naphthyl substituted with 0–3 $R^{4b}$; and 5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4b}$;

$R^{4a}$ is, at each occurrence, independently selected from: H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}C(=O)OR^{11a}$, —$NR^{11}C(=O)NR^{11}R^{11a}$, —$NR^{11}SO_2NR^{11}R^{11a}$, —$NR^{11}SO_2R^{11a}$; $C_1$–$C_4$ alkyl substituted with 0–1 $R^{4b}$; $C_2$–$C_4$ alkenyl substituted with 0–1 $R^{4b}$; $C_2$–$C_4$ alkynyl substituted with 0–1 $R^{4b}$; $C_3$–$C_7$ cycloalkyl substituted with 0–2 $R^{4c}$; phenyl substituted with 0–3 $R^{4c}$; naphthyl substituted with 0–3 $R^{4c}$; and 5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4c}$;

$R^{4b}$ is, at each occurrence, independently selected from: H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —C(=NH)$NHR^{11}$, =$NOR^{11}$, —$NR^{11}C(=O)OR^{11a}$, —OC(=O)$NR^{11}R^{11a}$, —$NR^{11}C(=O)NR^{11}R^{11a}$, —$NR^{11}SO_2NR^{11}R^{11a}$, —$NR^{11}SO_2R^{11a}$, —OP(O)$(OR^{11})_2$; $C_1$–$C_4$ alkyl substituted with 0–2 $R^{4c}$; $C_2$–$C_4$ alkenyl substituted with 0–2 $R^{4c}$; $C_2$–$C_4$ alkynyl substituted with 0–2 $R^{4c}$; $C_3$–$C_6$ cycloalkyl substituted with 0–3 $R^{4d}$; phenyl substituted with 0–3 $R^{4d}$; naphthyl substituted with 0–3 $R^{4d}$; and 5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4d}$;

$R^{4c}$ is, at each occurrence, independently selected from: H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11}$, —C(=O)$R^{11a}$, —S(=O)$R^{11a}$, —$SO_2R^{11}$, —$SO_2NR^{11}R^{11a}$, $C_1$–$C_4$ haloalkyl, $C_1$–$C_4$ haloalkoxy; $C_1$–$C_4$ alkyl substituted with 0–1 $R^{4d}$; $C_2$–$C_4$ alkenyl substituted with 0–1 $R^{4d}$; $C_2$–$C_4$ alkynyl substituted with 0–1 $R^{4d}$; $C_3$–$C_6$ cycloalkyl substituted with 0–2 $R^{4d}$; phenyl substituted with 0–3 $R^{4d}$; naphthyl substituted with 0–3 $R^{4d}$; and 5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4d}$;

$R^{4d}$ is, at each occurrence, independently selected from: H, F, Cl, Br, I, —$NO_2$, —CN, —NCS, —$CF_3$, —$OCF_3$, =O, OH, —$CO_2H$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, $C_1$–$C_4$ alkyl, $C_1$–$C_4$ alkoxy, $C_1$–$C_4$ haloalkyl, $C_1$–$C_4$ haloalkoxy, phenyl, and benzyl;

$R^6$ is H, methyl, ethyl, propyl, or butyl;

$R^8$ is H or methyl;

$R^{9a}$ is selected from the group: H; $C_1$–$C_4$ alkyl substituted with 0–1 $R^{9c}$; $C_2$–$C_4$ alkenyl substituted with 0–1 $R^{9c}$; $C_2$–$C_4$ alkynyl substituted with 0–1 $R^{9c}$; phenyl substituted with 0–3 $R^{9d}$; and 5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–3 $R^{9d}$;

$R^{9b}$ is selected from the group: H, —C(=O)$R^{9c}$, —(=O)$OR^{9c}$, —C(=O)$NHR^{9c}$, $C_1$–$C_4$ alkyl, and phenyl;

$R^{9c}$ is selected from the group: $CF_3$, $OCF_3$, Cl, F, OH, C(O)$OR^{11}$, $NH_2$, NH($CH_3$), N($CH_3$)$_2$, —CN, $NO_2$, and phenyl;

$R^{9d}$ is selected at each occurrence from the group: $CF_3$, $OCF_3$, Cl, F, Br, OH, C(O)$OR^{11}$, $NH_2$, NH($CH_3$), N($CH_3$)$_2$, —CN, $NO_2$, $C_1$–$C_4$ alkyl, $C_1$–$C_4$ alkoxy, and phenyl;

$R^{11}$ and $R^{11a}$ are, at each occurrence, independently selected from the group: H, methyl, ethyl, propyl, butyl, phenyl and benzyl;

$R^{13}$ is selected from the group: H, $C_1$–$C_4$ alkyl, phenyl and phenyl-$C_1$–$C_4$ alkyl;

$OR^{26}$ and $OR^{27}$ are independently selected from: a)-OH, d) $C_1$–$C_8$ alkoxy, and when taken together, $OR^{26}$ and $OR^{27}$ form: e) a cyclic boronic ester where said cyclic boronic ester is formed from the group: pinanediol, pinacol, 1,2-ethanediol, 1,3-propanediol, 1,2-propanediol, 2,3-butanediol, 1,2-diisopropylethandio, 5,6-decanediol, 1,2-dicyclohexylethanediol, diethanolamine, and 1,2-diphenyl-1,2-ethanediol; and $A^4$ is selected from the group: Ala, Arg, Asn, Asp, Aze, Cys, Gln, Glu, Gly, His, Hyp, Ile, Leu, Lys, Met, Orn, Phe, Pro, Sar, Ser, Thr, Trp, Tyr, Val, Abu, Alg, Ape, Cha, Cpa, Cpg, Dfb, Dpa, Gla, Irg, HomoLys, Phe(4-fluoro), Tpa, Asp(OMe), Glu(OMe), Hyp(OMe), Asp(O′Bu), Glu(O′Bu), Hyp(O′Bu), Thr(O′Bu), Asp(OBzl), Glu(OBzl), Hyp(OBzl), Pro(OBzl), Thr(OBzl), cyclohexylglycine, cyclohexylalanine, cyclopropylglycine, t-butylglycine, phenylglycine, and 3,3-diphenylalanine.

3. A compound of claim 2, or a stereoisomer, or pharmaceutically acceptable salt form wherein:

$A^1$ is —$CH_2$—;

$A^3$ is H, —$NHCOR^{9a}$, —$CONHR^{9a}$, —NHC(=O)$OR^{9a}$, —$NR^8R^{9a}$; or —NH—$A^4$—$R^{9b}$;

W is pinanediol boronic ester;

$R^1$ is selected from the group: H; $C_1$–$C_4$ alkyl substituted with 0–2 $R^{1a}$; $C_2$–$C_4$ alkenyl substituted with 0–2 $R^{1a}$; and $C_2$–$C_4$ alkynyl substituted with 0–2 $R^{1a}$;

$R^{1a}$ is selected at each occurrence from the group: Cl, F, Br, $CF_3$, and $CHF_2$;

$R^2$ is H;

$R^3$ is selected from the group: $R^4$, —$(CH_2)_p$—NH—$R^4$, —$(CH_2)_p$—NHC(=O)—$R^4$, —$(CH_2)_p$—C(=O)NH—$R^4$, —$(CH_2)_p$—C(=O)O—$R^4$, —$(CH_2)_p$—NHC(=O)NH—$R^4$, —$(CH_2)_p$—NHC(=O)NHC(=O)—$R^4$, —$(CH_2)_p$—C(=O)—$R^4$, —$(CH_2)_p$—O—$R^4$, and —$(CH_2)_p$—S—$R^4$;

p is 0 or 1;

$R^4$ is selected from the group: $C_1$–$C_4$ alkyl substituted with 0–3 $R^{4a}$; $C_2$–$C_4$ alkenyl substituted with 0–3 $R^{4a}$; $C_2$–$C_4$ alkynyl substituted with 0–3 $R^{4a}$; $C_3$–$C_6$ cycloalkyl substituted with 0–2 $R^{4b}$; phenyl substituted with 0–3 $R^{4b}$; naphthyl substituted with 0–3 $R^{4b}$; and 5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4b}$;

$R^{4a}$ is, at each occurrence, independently selected from: H, F, Cl, Br, I, —$NO_2$, —CN, —NCS, —$CF_3$, —$OCF_3$, =O, OH, —$CO_2H$, —C(=NH)$NH_2$, —$CO_2R^{11}$, —C(=O)$NR^{11}R^{11a}$, —NHC(=O)$R^{11}$, —$NR^{11}R^{11a}$, —$OR^{11a}$, —$SR^{11a}$, —C(=O)$R^{11a}$, —S(=O)$R^{11a}$, —$SO_2R^{11}$, —$SO_2NR^{11}R^{11a}$, —NHC(=NH)$NHR^{11}$, —C(=NH)$NHR^{11}$, =$NOR^{11}$, —$NR^{11}$—C(=O)$OR^{11a}$, —$NR^{11}$—C(=O)$NR^{11}R^{11a}$, —$NR^{11}SO_2NR^{11}R^{11a}$, —$NR^{11}SO_2R^{11a}$; $C_1$–$C_4$ alkyl substituted with 0–1 $R^{4b}$; $C_2$–$C_4$ alkenyl substituted with 0–1 $R^{4b}$; $C_2$–$C_4$ alkynyl substituted with 0–1 $R^{4b}$; $C_3$–$C_7$ cycloalkyl substituted with 0–2 $R^{4c}$; phenyl substituted with 0–3 $R^{4c}$; naphthyl substituted with 0–3 $R^{4c}$; and 5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 $R^{4c}$;

$R^{4b}$ is, at each occurrence, independently selected from: H, F, Cl, Br, I, —$NO_2$, —CN, —NCS, —$CF_3$, —$OCF_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11a}$, —NHC(=NH)NHR$^{11}$, —C(=NH)NHR$^{11}$, =NOR$^{11}$, —NR$^{11}$—C(=O) OR$^{11a}$, —OC(=O)NR$^{11}$R$^{11a}$, —NR$^{11}$—C(=O) NR$^{11}$R$^{11a}$, —NR$^{11}$SO$_2$NR$^{11}$R$^{11a}$, —NR$^{11}$SO$_2$R$^{11a}$, —OP(O)(OR$^{11}$)$_2$; C$_1$–C$_4$ alkyl substituted with 0–2 R$^{4c}$; C$_2$–C$_4$ alkenyl substituted with 0–2 R$^{4c}$; C$_2$–C$_4$ alkynyl substituted with 0–2 R$^{4c}$; C$_3$–C$_4$ cycloalkyl substituted with 0–2 R$^{4d}$; phenyl substituted with 0–3 R$^{4d}$; naphthyl substituted with 0–3 R$^{4d}$; and 5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 R$^{4d}$;

R$^{4c}$ is, at each occurrence, independently selected from: H, F, Cl, Br, I, —NO$_2$, —CN, —NCS, —CF$_3$, —OCF$_3$, =O, OH, —CO$_2$H, —C(=NH)NH$_2$, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11a}$, C$_1$–C$_4$ haloalkyl, C$_1$–C$_4$ haloalkoxy; C$_1$–C$_4$ alkyl substituted with 0–1 R$^{4d}$; C$_2$–C$_4$ alkenyl substituted with 0–1 R$^{4d}$; C$_2$–C$_4$ alkynyl substituted with 0–1 R$^{4d}$; C$_3$–C$_6$ cycloalkyl substituted with 0–2 R$^{4d}$; phenyl substituted with 0–3 R$^{4d}$; naphthyl substituted with 0–3 R$^{4d}$; and 5–10 membered heterocyclic group selected from the group: pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, pyrazolopyridinyl, 4H-quinolizinyl, benzofuranyl, benzothiophenyl, quinazolinyl, quinolinyl, 4H-quinolizinyl, and quinoxalinyl; and said 5–10 membered heterocyclic group is substituted with 0–3 R$^{4d}$;

R$^{4d}$ is, at each occurrence, independently selected from: H, F, Cl, Br, I, —NO$_2$, —CN, —NCS, —CF$_3$, —OCF$_3$, =O, OH, —CO$_2$H, —CO$_2$R$^{11}$, —C(=O)NR$^{11}$R$^{11a}$, —NHC(=O)R$^{11}$, —NR$^{11}$R$^{11a}$, —OR$^{11a}$, —SR$^{11a}$, —C(=O)R$^{11a}$, —S(=O)R$^{11a}$, —SO$_2$R$^{11}$, —SO$_2$NR$^{11}$R$^{11a}$, C$_1$–C$_4$ alkyl, C$_1$–C$_4$ alkoxy, C$_1$–C$_4$ haloalkyl, C$_1$–C$_4$ haloalkoxy, phenyl, and benzyl;

R$^6$ is H, methyl, ethyl, propyl, or butyl;

R$^8$ is H or methyl;

R$^{9a}$ is selected from the group: H; C$_1$–C$_4$ alkyl substituted with 0–1 R$^{9c}$; C$_2$–C$_4$ alkenyl substituted with 0–1 R$^{9c}$; C$_2$–C$_4$ alkynyl substituted with 0–1 R$^{9c}$; phenyl substituted with 0–3 R$^{9d}$; and 5–6 membered heterocyclic group consisting of carbon atoms and 1–4 heteroatoms selected from the group: O, S, and N; optionally saturated, partially unsaturated or unsaturated; and said 5–6 membered heterocyclic group is substituted with 0–3 R$^{9d}$;

R$^{9b}$ is selected from the group: H, —C(=O)R$^{9c}$, —C(=O)OR$^{9c}$, —(=O)NHR$^{9c}$, C$_1$–C$_4$ alkyl, and phenyl;

R$^{9c}$ is selected from the group: CF$_3$, OCF$_3$, Cl, F, Br, OH, C(O)OR$^{11}$, NH$_2$, NH(CH$_3$), N(CH$_3$)$_2$, —CN, NO$_2$, and phenyl;

R$^{9d}$ is selected at each occurrence from the group: CF$_3$, OCF$_3$, Cl, F, Br, OH, C(O)OR$^{11}$, NH$_2$, NH(CH$_3$), N(CH$_3$)$_2$, —CN, NO$_2$, C$_1$–C$_4$ alkyl, C$_1$–C$_4$ alkoxy, and phenyl;

R$^{11}$ and R$^{11a}$ are, at each occurrence, independently selected from the group: H, methyl, ethyl, propyl, butyl, phenyl and benzyl;

R$^{13}$ is selected from the group: H, C$_1$–C$_4$ alkyl, phenyl and phenyl-C$_1$–C$_4$ alkyl; and A$^4$ is selected from the group: Val, Ile, Leu, cyclohexylglycine, cyclopropylglycine, t-butylglycine, phenyiglycine, and 3,3-diphenylalanine.

4. A compound of claim 3, or a stereoisomer, or pharmaceuticaLly acceptable salt form wherein:

A$^1$ is —CH$_2$—;

A$^3$ is H, —NHCOR$^{9a}$, —NHC(=O)OR$^{9a}$, or —NR$^8$R$^{9a}$;

W is pinanediol boronic ester;

R$^1$ is H, ethyl, allyl, or 2,2-difluoro-ethyl;

R$^2$ is H;

R$^3$ is selected from the group: R$^4$, —(CH$_2$)$_p$—NH—R$^4$, —(CH$_2$)$_p$—NHC(=O)—R$^4$, (CH$_2$)$_p$—C(=O)NH—R$^4$, —(CH$_2$)$_p$—C(=O)O—R$^4$, —(CH$_2$)$_p$—NHC(=O) NH—R$^4$, —(CH$_2$)$_p$—NHC(=O)NHC(=O)—R$^4$, —(CH$_2$)$_p$—C(=O)—R$^4$, —(CH$_2$)$_p$—O—R$^4$, and —(CH$_2$)$_p$—S—R$^4$;

p is 0 or 1;

R$^4$ selected from the group: methyl, isopropyl, t-butyl, phenyl, benzyl, phenethyl, Ph-propyl, phenyl, 2-benzoic acid, 5-isophthalate dimethyl ester, triphenylmethyl, 1-(1-naphthyl)ethyl, 2-methylphenyl, 4-methylphenyl, 4-ethylphenyl, 2-isopropylphenyl, 4-isopropylphenyl, 4-tert-butylphenyl, 2-methoxyphenyl, 3-methoxyphenyl, 4-methoxyphenyl, 2-ethoxyphenyl, 4-ethoxyphenyl, 2-F-phenyl, 3-F-phenyl, 4-F-phenyl, 2-Cl-phenyl, 4-Cl-phenyl, 2-CF$_3$-phenyl, 3-CF$_3$-phenyl, 4-CF$_3$-phenyl, 4-(trifluoromethoxy)phenyl, 2-(hydroxymethyl)phenyl, 4-(hydroxymethyl)phenyl, 3-cyanophenyl, 3-(acetyl)phenyl, 2-phenoxyphenyl, 3-phenoxyphenyl, 4-(acetyl)phenyl, 2-(methoxycarbonyl)-phenyl, 3-(methoxycarbonyl)-phenyl, 4-(methoxycarbonyl)-phenyl, 2-(ethoxycarbonyl)-phenyl, 3-(ethoxycarbonyl)-phenyl, 4-(ethoxycarbonyl)phenyl, 2-(butoxycarbonyl) phenyl, 2-(tert-butoxycarbonyl)phenyl, 4-(dimethylamino)phenyl, 2-((dimethylamino) carbonyl)phenyl, 2-(methylamino)carbonylphenyl, 2-(aminocarbonyl)phenyl, 2-(methylthio)phenyl, 3-(methylthio)phenyl, 4-(methylthio)phenyl, 2-(methylsulfonyl)phenyl, 3-CF$_3$S-phenyl, 2-nitrophenyl, 4-nitrophenyl, 2-aminophenyl, 4-(benzyloxy)phenyl, 2-biphenyl, 4-biphenyl, 2,6-diisopropyiphenyl, 2,4-diF-phenyl, 2,5-diF-phenyl, 2,6-diF-phenyl, 3,4-dichlorophenyl, 2,4-dimethoxyphenyl, 2,5-dimethoxyphenyl, 5-Cl-2-methoxyphenyl, 4-F-2-nitrophenyl, 3,4,5,-trimethoxyphenyl, 5-Cl-2,4-dimethoxyphenyl, 5-F-2,4-dimethoxyphenyl, Trans-2-phenylcyclopropyl, 1-naphthyl, 2-naphthyl, 2-pyridinyl, 3-pyridinyl, 2-quinolinyl, 5-quinolinyl, 1-isoquinolinyl, 2-phenyl-4-quinolinyl, 2-methyl-6-quinolinyl, 2-methyl-4-quinolinyl, 2-3-methylbutyric acid methyl ester, 4-benzyl-1-piperidinyl, 4-(2-oxo-2,3-dihydro-1H-benzimidazol-1-yl)-1-piperidinyl, 3-methyl-3-phenyl-piperidinyl, 4-benzyl-4-hydroxy-1-piperidinyl, 4-benzyl-1-piperazinyl, 4-phenyl-1-piperazinyl, 1-Benzyloxycarbonyl-piperazinyl, 4-(4-acetylphenyl)-1-piperazinyl, and 3,4-dihydro-2(1H)-isoquinolinyl;

$R^6$ is H;

$R^8$ is H;

$R^{9a}$ is selected from the group: H; $C_1$–$C_4$ alkyl substituted with 0–1 $R^{9c}$; phenyl substituted with 0–3 $R^{9d}$; and 5–6 membered heterocyclic group consisting of carbon atoms and 1–3 heteroatoms selected from the group: O, S, and N; optionally saturated, partially unsaturated or unsaturated; and said 5–6 membered heterocyclic group is substituted with 0–2 $R^{9d}$;

$R^{9c}$ is selected from the group: $CF_3$, $OCF_3$, Cl, F, Br, OH, $C(O)OR^{11}$, $NH_2$, $NH(CH_3)$, $N(CH_3)_2$, —CN, $NO_2$, and phenyl;

$R^{9d}$ is selected from the group: $CF_3$, $OCF_3$, Cl, F, Br, OH, $C(O)OR^{11}$, $NH_2$, $NH(CH_3)$, $N(CH_3)_2$, —CN, $NO_2$, $C_1$–$C_4$ alkyl, $C_1$–$C_4$ alkoxy, and phenyl;

$R^{11}$ is selected from the group: H, methyl, ethyl, propyl, butyl and benzyl; and $R^{13}$ is selected from the group: H, methyl and Ph-propyl.

5. A compound of claim 1, or a stereoisomer or pharmaceutically acceptable salt form thereof, selected from the group consisting of:

benzyl (6S)-6-[{(1R)-1-[(3aS,4S,6S,7aR)-hexahydro-3a,5,5-trimethyl-4,6-methano-1,3,2-benzodioxaborol-2-yl]amino}carbonyl]-4-oxo-4,6,7,8-tetrahydropyrrolo[1,2-a]pyrimidin-3-ylcarbamate;

benzyl (6S)-6-[({(1R)-1-[(3aS,4S,6S,7aR)-hexahydro-3a,5,5,-trimethyl-4,6-methano-1,3,2-benzodioxaborol-2-yl}amino)carbonyl]-4-oxo-4,6,7,8-tetrahydropyrrolo[1,2-a]pyrimidin-3-ylcarbamate;

(6S)-N-{(1R)-1-[(3aS,4S,6S,7aR)-hexahydro-3a,5,5,-trimethyl-4,6-methano-1,3,2-benzodioxaborol-2-yl]propyl}-3-amino-4-oxo-4,6,7,8-tetrahydropyrrolo[1,2-a]pyrimidine-6-carboxamide hydrochloride;

(6S)-N-{(1R)-1-[(3aS,4S,6S,7aR)-hexahydro-3a,5,5,-trimethyl-4,6-methano-1,3,2-benzodioxaborol-2-yl]propyl}-3-(benzylamino)-4-oxo-4,6,7,8-tetrahydropyrrolo[1,2-a]pyrimidine-6-carboxamide;

(6S)-N-{(1R)-1-[(3aS,4S,6S,7aR)-hexahydro-3a,5,5,-trimethyl-4,6-methano-1,3,2-benzodioxaborol-2-yl]propyl}-4-oxo-3-{[3-(trifluoromethyl)benzyl]amino}-4,6,7,8-tetrahydropyrrolo[1,2-a]pyrimidine-6-carboxamide;

(6S)-N-{(1R)-1-[(3aS,4S,6S,7aR)-hexahydro-3a,5,5,-trimethyl-4,6-methano-1,3,2-benzodioxaborol-2-yl]propyl}-3-(benzoylamino)-4-oxo-4,6,7,8-tetrahydropyrrolo[1,2-a]pyrimidine-6-carboxamide;

(6S)-N-{(1R)-1-[(3aS,4S,6S,7aR)-hexahydro-3a,5,5,-trimethyl-4,6-methano-1,3,2-benzodioxaborol-2-yl]propyl}-3-(acetylamino)-4-oxo-4,6,7,8-tetrahydropyrrolo[1,2-a]pyrimidine-6-carboxamide;

benzyl (6S,8RS)-6-[({(1R)-1-[(3aS,4S,6S,7aR)-hexahydro-3a,5,5,-trimethyl-4,6-methano-1,3,2-benzodioxaborol-2-yl]propyl}amino)carbonyl]-4-oxo-8-(3-phenylpropyl)-4,6,7,8-tetrahydropyrrolo[1,2-a]pyrimidin-3-ylcarbamate;

benzyl (6S,8S)-6-[({(1R)-1-[(3aS,4S,6S,7aR)-hexahydro-3a,5,5,-trimethyl-4,6-methano-1,3,2-benzodioxaborol-2-yl]propyl}amino)carbonyl]-4-oxo-8-(3-phenylpropyl)-4,6,7,8-tetrahydropyrrolo]1,2-a]pyrimidin-3-ylcarbamate;

(6S,8R)-N-{(1R)-1-[(3aS,4S,6S,7aR)-hexahydro-3a,5,5,-trimethyl-4,6-methano-1,3,2-benzodioxaborol-2-yl]propyl}-4-oxo-8(3-phenylpropyl)-3-{[3-(trifluromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5,-trimethyl-4,6-methano-1,3,2-benzodioxaborol-2-yl]propyl}-4-oxo-8(3-phenylpropyl)-3-{[3-(trifluromethyl)benzyl]amino}-4,6,7,8-tetrahydropyrrolo[1,2-a]pyrimidine-6-carboxamide;

(6,S8R)-N-{(1R)-1-[(3aS,4S,6S,7aR)-hexahydro-3a,5,5,-trimethyl-4,6-methano-1,3,2-benzodioxaborol-2-ylpropyl]}-8-amino-8methyl-4-oxo-8[(phenylacetyl)amino]-3-{[3-(trifluromethyl)benzyl]amino}-4,6,7,8-tetrahydropyrrolo[1,2-a]pyrimidine-6-carboxamide;

phenyl (6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]8-methyl-4-oxo-3-{[-3-(trifluoromethyl)benzyl]amino}-4,6,7,8-tetrahydropyrrolo[1,2-a]pyrimidin-8-ylcarbamate;

N-((6S,8R)-6-[({(1R)-1-[(3aS,4S,6S,7aR)-hexahydro-3a,5,5-trimethyl-4,6-methano-1,3,2-benzodioxaborol-2-yl]propyl)amino)carbonyl]-8-methyl-4-oxo-3-{[3-(trifluoromethyl)benzyl]amino)-4,6,7,8-tetrahydropyrrolo[1,2-a]pyrimidin-8-yl)-2-phenyl-4-quinolinecarboxamide;

(6S,8R)-N-{(1R)-1-[(3aS,4S,6S,7aR)-hexahydro-3a,5,5,-trimethyl-4,6-methano-1,3,2-benzodioxaborol-2-tetrahydropyrrolo[1,2-a]pyrimidine-6-carboxamide;

(6S,8R)-N-{(1R)-1-[(3aS,4S,6S,7aR)-hexahydro-3a,5,5,-trimethyl-4,6-methano-1,3,2-benzodioxaborol-2-yl]propyl}-8-{[(benzoylamino)carbonyl]amino}-8-methyl-4-oxo-3-{[3-(trifluoromethyl)benzyl]amino}-4,6,7,8,-tetrahydropyrrolo[1,2-a]pyrimidine-6-carboxamide;

(6S,8R)-N-{(1R)-1-[(3aS,4S,6S,7aR)-hexahydro-3a,5,5,-trimethyl-4,6-methano-1,3,2-benzodioxaborol-2-yl]propyl}-8-{[(4-methoxyanilino)carbonyl]amino}-8methyl-4oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5,-trimethyl-4,6-methano-1,3,2-benzodioxaborol-2-yl]propyl{-8-([(2-fluoroanilino)carbonyl]amino}-8-methyl-4-oxo-3-{[3-trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5,-trimethyl-4,6-methano-1,3,2-benzodioxaborol-2-yl]propyl}-8-{[(3-methoxyanilino)carbonyl]amino}-8methyl-4oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5,-trimethyl-4,6-methano-1,3,2-benzodioxaborol-2-yl]propyl}-8-methyl-8-{[(1-naphthylamino)carbonyl]amino}-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5,-trimethyl-4,6-methano-1,3,2-benzodioxaborol-2-tetrahydropyrrolo[1,2-a]pyrimidine-6-carboxamide;

(6S,8R)-N-{(1R)-1-[(3aS,4S,6S,7aR)-hexahydro-3a,5,5,-trimethyl-4,6-methano-1,3,2-benzodioxaborol-2-yl]propyl}-8-{[(3-acetylanilino)carbon]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5,-trimethyl-4,6-methano-1,3,2-benzodioxaborol-2-yl]

propyl}-8-methyl-4-oxo-8-{[(4-phenoxyanilino)
carbonyl]amino}3-{[3-(trifluoromethyl)benzyl]amino}-
4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(4-acetylanilino)carbon]amino}-8-methyl-4-
oxo-3-{[3-(trifluoromethyl)benzyl]amino}-4,6,7,8-
tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-8-{[(2-naphthylamino)carbonyl]
amino}-4-oxo-3-{[3-(trifluoromethyl)benzyl]amino}-4,
6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-{[(( trans-2-
phenylcyclopropyl)amino)carbonyl]amino}-3-{[3-
(trifluoromethyl)benzyl]amino}-4,6,7,8-
tetrahydropyrrolo[1,2-a]pyrimidine-6-carboxamide;

(6S,8R)-N-}(1R)-1-[(3aS,4S,6S,7aR)-hexahydro-3a,5,5-
trimethyl-4,6-methano-1,3,2-benzodioxaborol-2yl]
propyl}-8{[(2,4-difluoroanilino)carbonyl]amino}-
8methyl-4-oxo-3-{[3-(trifluoromethyl)benzyl]amino}-4,
6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(2,5difluoroanilino)carbonyl]amino}-8-
methyl-4-oxo-3{[3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(2-methoxyanilino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-{[(2-(trifluoromethyl)anilino)
carbonyl]amino}-3-{[3-(trifluoromethyl)benzyl]amino}-
4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(3-fluoroanilino)carbonyl]amino}-8-methyl-
4-oxo-3-{[3-(trifluoromethyl)benzyl]amino}-4,6,7,8-
tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-{[(3-(trifluoromethyl)anilino)
carbonyl]amino}-3-{[3-(trifluoromethyl)benzyl]amino}-
4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(4-fluoroanilino)carbonyl]amino}-8-methyl-
4-oxo-3-{[3(trifluoromethyl)benzyl]amino}-4,6,7,8-
tetrahydropyrrolo[1,2-a]pyrimidine-6-carboxamide;

(6S,8R)-N-[(1R)-1-[(3aS,4S,6S,7aR)-hexahydro-3a,5,5-
trimethyl-4,6-methano-1,3,2-benzodioxaborol-2-yl]
propyl}-8-methyl-4-oxo-8-{[(4-(trifluorornethyl)anilino)
carbony]amino}-3-{[3-(trifluoromethyl)benzyl]amino}-
4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-8-{[(4-methylanilino)carbonyl]
amino}-4-oxo-3-{[3-(trifluoromethyl)benzyl]amino}-4,
6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(2-diisopropylanilino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

methyl 2-({[(((6S,8R)-6-[({(1R)-1-[(3aS,4S,6S,7aR)-
hexahydro-3a,5,5-trimethyl-4,6-methano-1,3,2-
benzodioxaboro-2-yl]propyl}amino)carbonyl]-8-methyl-
4-oxo-{[3-(trifluoromethyl)benzyl]amino}-4,6,7,8-
tetrahydropyrrolo[1,2-a]pyrimidin-8-yl)amino]
carbonyl}amino)benzoate;

ethyl 2-({[(((6S,8R)-6-[({(1R)-1-[(3aS,4S,6S,7aR)-
hexahydro-3a,5,5-trimethyl-4,6-methano-1,3,2-
benzodioxaboro-2-yl]propyl}amino)carbonyl]-8-methyl-
4-oxo-3-{[3-(trifluoromethyl)benzyl]amino}-4,6,7,8-
tetrahydropyrrolo[1,2-a]pyrimidin-8-yl)amino]
carbonyl}amino)benzoate;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(2-isopropylanilino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-4-oxo-3-{[3-(trifluoromethyl)benzyl]
amino}-8-{[(3,4,5-trimethoxyanilino)carbonyl]amino}-
4,6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-8-{[(3-(methylthio)anilion)carbonyl]
amino}-4-oxo-3-{[3-(trifluoromethyl)benzyl]amino}-4,
6,7,8-tetrahydropyrrolo[1,2-a]pyrimidine-6-
carboxamide;

ethyl 3-({[(((6S,8R)-6-[({(1R)-1-[(3aS,4S,6S,7aR)-
hexahydro-3a,5,5-trimethyl-4,6-methano-1,3,2-
benzodioxaboro-2-yl]propyl}amino)carbonyl]-8-methyl-
4-oxo-{[3-(trifluoromethyl)benzyl]amino}-4,6,7,8-
tetrahydropyrrolo[1,2-a]pyrimidin-8-yl)amino]
carbonyl}amino)benzoate;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(4-ethoxyanilino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-methyl-8-{[(4-(methylthio)anilion)carbonyl]
amino}-4-oxo-3-{[3-(trifluoromethyl)benzyl]amino}-4,
6,7,8-tetrahydropyrrolo[1,2-a]pyrimidine-6-
carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(4-isopropylanilino)carbonyl]amino}-8-
methyl-4-oxo-3-{[3-(trifluoromethyl)benzyl]amino}-4,6,
7,8-tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]
propyl}-8-{[(4-ethylanilino)carbonyl]amino}-8-methyl-
4-oxo-3-{[3-(trifluoromethyl)benzyl]amino}-4,6,7,8-
tetrahydropyrrolo[1,2-a]pyrimidine-6-carboxamide;

(6S,8R)-N-{(1R)-1-[(3aS,4S,6S,7aR)-hexahydro-3a,5,5-
trimethyl-4,6-methano-1,3,2-benzodioxaborol-2-yl]

propyl}-8-methyl-4-oxo-8-{[(4-(trifluoromethoxy)anilino)carbonyl]amino}-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-({[(2-phenylethyl)amino]carbonyl}amino)-3-{[3-(trifluoromethyl)benzyl]amino}-4,6,7,8-tetrahydropyrrolo[1,2-a]pyrimidine-6-carboxamide;

methyl 3-({[(((6S,8R)-6-[({(1R)-1-[(3aS,4S,6S,7aR)-hexahydro-3a,5,5-trimethyl-4,6-methano-1,3,2-benzodioxaboro-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[([1,1'-biphenyl]-2-ylamino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-3-{[3-(trifluoromethyl)benzyl]amino}-8-{[(tritylamino)carbonyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaboro-2-yl]propyl}-8-methyl-8-[({[(1R)-1-(1-naphthyl)ethyl]amino}carbonyl)amino]-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-[({[(1S)-1-(1-phenyl)ethyl]amino}carbonyl)amino]-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(isopropylamino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-{[(2-phenoxyanilino)carbonyl]amino}-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl{-8-{[(2,6-difluoroanilino)carbonyl]amino}-8-methyl-4-oxo-3-{]3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-[({[(1R)-1-(1-phenyl)ethyl]amino}carbonyl)amino]-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(4-isopropylanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-({[(4-dimethylamino)anilino]carbonyl}amino)-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(3,4-dichloroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide (6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(4-tert-butylanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

methyl 2-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-trifluoromethyl)benzyl]amino}-4,6,7,8-tetrahydropyrrolo[1,2-a]pyrimidin-8-yl)amino]carbonyl}amino)-3-methylbutanoate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(benzylamino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-({[(4-chlorobenzoyl)amino]carbonyl}amino)-8-methyl-4-oxo-3-{[3-(trifluoromethyl)benzyl]amino}-4,6,7,8-tetrahydropyrrolo[1,2-a]pyrimidine-6-carboxamide;

tert-butyl 2-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate;

2-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoic acid;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2-chloroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2,5-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-[(2-toluidinocarbonyl)amino]-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(5-chloro-2,4-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2,4-dimethoxyanilino)carbonyl]amino}-8- methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2-ethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(5-chloro-2-methoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

butyl 2-(}[(({(6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidine-8-yl) amino]carbonyl}amino)benzoate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-8-({[(2-methylthio)anilino]carbonyl}amino)-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(4-chloroanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-8-{[(4-fluoro-2-nitroanilino)carbonyl]amino}-4-oxo-3-{[3-(trifluoromethyl)benzyl]amino}-4,6,7,8-tetrahydropyrrolo[1,2-a]pyrimidine-6-carboxamide;

dimethyl 5-(([(((6S,8R)-6-[({(1R)-1-[(3aS,4S,6S,7aR)-hexahydro-3a,5,5-trimethyl-4,6-methano-1,3,2-benzodioxaborol-2-yl]-propyl}amino)carbonyl]-8-methyl-4-oxo-3-{[3-(trifluoromethyl)benzyl]amino)-4,6,7,8-tetrahydropyrrolo[1,2-a]pyrimidin-8-yl)amino]carbonyl}amino)isophthalate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-3-{[3-(trifluoromethyl)benzyl]amino}-8-[({3-[(trifluoromethyl)sulfanyl]anilino}carbonyl)amino]-4,6,7,8-tetrahydropyrrolo[1,2-a]pyrimidine-6-carboxamide;

ethyl 4-({[(((6S,8R)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-8-{[(2-nitroanilino)carbonyl]amino}-4-oxo-3-{[3-(trifluoromethyl)benzyl]amino)-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(2-aminoanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

N-((6S,8R)-6-[({(1RS)-1-[(3aS,4S,6S,7aR)-hexahydro-3a,5,5-trimethyl-4,6-methano-1,3,2-benzodioxaborol-2-yl]-3,3-difluropropyl}amino)carbonyl]-8-methyl-4-oxo-3-{[3-(trifluoromethyl)benzyl]amino}-4,6,7,8-tetrahydropyrrolo[1,2-a]pyrimidin-8-yl)-2-phenyl-4-quinolinecarboxamide;

(6S,8R)-N-{(1RS)-1-[(3aS,4S,6S,7aR)-hexahydro-3a,5,5-trimethyl-4,6-methano-1,3,2-benzodioxaborol-2-yl]-3,3-difluoropropyl}-8-{[(2,5-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1RS)-1-[(3aS,4S,6S,7aR)-hexahydro-3a,5,5-trimethyl-4,6-methano-1,3,2-benzodioxaborol-2-yl]-3,3-difluoropropyl}-8-{[(2,5-dimethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

methyl 2-({[((6S,8R)-6-[({(1RS)-1-[(3aS,4S,6S,7aR)-hexahydro-3a,5,5-trimethyl-4,6-methano-1,3,2-benzodioxaborol-2-yl]-3,3-difluoropropyl}amino)carbonyl]-8-methyl-4-oxo-3-{[3-(trifluoromethyl)benzyl]amino}-4,6,7,8-tetrahydropyrrolo[1,2-a]pyrimidin-8-yl)amino]carbonyl}amino)benzoate;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-8-{(2-(methylthionyl)anilino]carbonyl}amino)-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8{[(2-ethoxyanilino)carbonyl]amino}-8-methyl-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-{[(5-chloro-2-methoxyanilino)carbonyl]}amino)-8-methyl-4-oxo-3-{[3-(trifluoromethyl)benzyl]amino}-4,6,7,8-tetrahydropyrrolo[1,2-a]pyrimidine-6-carboxamide;

ethyl 2-({[(((6S,8R)-6-[({(1RS)-1-[(3aS,4S,6S,7aR)-hexahydro-3a,5,5-trimethyl-4,6-methano-1,3,2-benzodioxaborol-2-yl]-3,3-difluoropropyl}amino)carbonyl]-8-methyl-4-oxo-3-{[3-(trifluoromethyl)benzyl]amino}-4,6,7,8-tetrahydropyrrolo[1,2-a]pyramidin-8-yl)amino]carbonyl}amino)benzoate;

tert-butyl ((6S,8R)-6-]({1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetate;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-(2-anilino-2-oxoethyl)-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(4-nitoanilino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-[2-oxo-2-(2-pyridinylamino)ethyl]-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(1-naphthylamino)-2-oxoethyl]-8-methyl- 4-oxo-3-{[3-(trifluoromothyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(3-methoxyanilino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-oxo-2-(5-quinolinylamino)ethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-{2-[(2-methyl-6-quinolinyl)amino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-oxo-2-(3-pyrinylamino)ethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(1-isoquinolinylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-2-oxoethyl]-8-methyl-4-oxo-8-[2-oxo-2-(2-quinolinylamino)ethyl]-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(2-methoxyanilino)-2-oxoethyl]-8-methyl-4-oxo-3-{[3-(trifluoromethyl)benzyl]amino}-4,6,7,8-tetrahydropyrrolo[1,2-a]pyrimldine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-([1,1'-biphenyl]-4-ylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

methyl 4-{[(((6S,8S)-6-[({(1R)-1-[(3aS,4S,6S,7aR)-Hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetyl]amino}benzoate;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-([benzylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-{2-[4-(hydroxymethyl)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(4-tert-butylanilino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-2-oxoethyl-]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-{2-[4-(benzyloxy)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide;

tert-butyl((6S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-4-oxo-3-{[3-(trifluoromethyl)benzyl]amino}-4,6,7,8-tetrahydropyrrolo[1,2-a]pyrimidin-8-yl)acetate;

(6S)-N-{(1R)-1-[(3aS,4S,6S,7aR)-hexahydro-3a,5,5-trimethyl-4,6-methano-1,3,2-benzodioxaborol-2-yl]propyl}-8-(2-anilino-2-oxoethyl)-4-oxo-3-{[3-(trifluoromethyl)benzyl]amino}-4,6,7,8-tetrahydropyrrolo[1,2-a]pyrimidine-6-carboxamide;

(6S,8R)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-(3-phenylpropyl)-3-{[3-(trifluoromethyl)benzyl]amino}-4,6,7,8-tetrahydropyrrolo[1,2-a]pyrimidine-6-carbaxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-(2-anilino-2-oxoethyl)-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(benzylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(1-isoquinolinylamino)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-Hexahydro-3a,5,5-trimethyl-4,6-methano-1,3,2-benzodioxaborol-2-yl]propyl}-8-[2-(2-methoxyanilino)-2oxoethyl]-8-methyl-4-oxo-3-{[3-(trifluoromethyl)benzyl]amino}-4,6,7,8-tetrahydropyrrolo[1,2-a]pyrimidine-6-carboxamide;

methyl 2-{[((6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetyl]amino}benzoate;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-[2-oxo-2-(3-pyrindinylamino)ethyl]-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-{2-[2-(hydroxymethyl)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(4-benzyl-1-piperidinyl)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-{2-oxo-2-[4-(2-oxo-2,3- dihydro-1H-benzimidazol-1-yl)-1-piperidinyl]ethyl}-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-8-[2-(3-methyl-3-phenyl-1-piperidinyl)-2-oxoethyl]-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(4-benzyl-4-hydroxy-1-piperidinyl)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(4-benzyl-1-piperazinyl)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-[2-oxo-2-(4-phenyl-1-piperazinyl)ethyl]-3-{[3-(trifluoromethyl)benzyl]amino}-4,6,7,8-tetrahydropyrrolo[1,2-a]pyrimidine-6-carboxamide benzyl 4-[((6S,8S)-6-[({(1R)-1-[(3aS,4S,6S,7aR)-hexahydro-3a,5,5-trimethyl-4,6-methano-1,3,2-benzodioxaborol-2-yl]propyl}amino)carbonyl]-8-methyl-4-oxo-3-{[3-(trifluoromethyl)benzyl]amino}-4,6,7,8-tetrahydropyrrolo[1,2-a]pyrimidin-8-yl)acetyl]-1-piperazinecarboxylate;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-[2-(3,4-dihydro-2(1H)-isoquinolinyl)-2-oxoethyl]-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-{2-[4-(4-acetylphenyl)-1-piperazinyl]-2-oxoethyl}-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl{2-[3-(methylsulfanyl)anilino]-2-oxoethyl}-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-8-{2-[(2-methyl-4-quinolinyl)amino]-2-oxoethyl}-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-8-[2-(1-naphthylamino)-2-oxoethyl]-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodiioxaborol-2-yl]propyl}8-methyl-8-[2-(2-nitroanilino)-2-oxoethyl]-4-oxo-3-{[3-(trifluromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-methyl-4-oxo-8-{2-oxo-2-[(2-phenyl-4-quinolinyl)amino]ethyl}-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-(2-{2-[(dimethyamino)carbonyl]anilino}-2-oxoethyl)-8-methyl-4-oxo-3-{[3-(trifluoromethyl)benzyl]amino}-4,6,7,8-tetrahydropyrrolo[1,2-a]pyrimidine-6-carboxamide;

(6S,8S)-N-{(1R)-1-[(3aS,4S,6S,7aR)-hexahydro-3a,5,5-trimethyl-4,6-methano-1,3,2-benzodioxaborol-2-yl]propyl}-8-(2-{2-[(methylamino)carbonyl]anilino}-2-oxoethyl)-8-methyl-4-oxo-3-{[3-(trifluoromethyl)benzyl]amino}-4,6,7,8-tetrahydropyrrolo[1,2-a]pyrimidine-6-carboxamide; and (6S,8S)-N-{(1R)-1-[(3aS,4S,6S,7aR)-hexahydro-3a,5,5-trimethyl-4,6-methano-1,3,2-benzodioxaborol-2-yl]propyl}-8-{2-[2-(aminocarbonyl)anilino]-2-oxoethyl}-8-methyl-4-oxo-3-{[3-(trifluoromethyl)benzyl]amino}-4,6,7,8-tetrahydropyrrolo[1,2-a]pyrimidine-6-carboxamide.

6. A pharmaceutical composition comprising a pharmaceutically acceptable carrier and a therapeutically effective amount of a compound of claim 1, or a pharmaceutically acceptable salt form thereof.

7. A method of treating HCV infection which comprises administering to a host in need of such treatment a therapeutically effective amount of a compound of claim 1, or a pharmaceutically acceptable salt thereof.

\* \* \* \* \*